US011857631B2

(12) United States Patent
Jeffries et al.

(10) Patent No.: US 11,857,631 B2
(45) Date of Patent: Jan. 2, 2024

(54) PROTECTION AND DELIVERY OF MULTIPLE THERAPEUTIC PROTEINS

(71) Applicant: University of Pittsburgh—Of the Commonwealth System of Higher Education, Pittsburgh, PA (US)

(72) Inventors: Eric M. Jeffries, West New York, NJ (US); Yadong Wang, Bradford Woods, PA (US); Daniel Long, Pittsburgh, PA (US); Noah R. Johnson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/533,958

(22) Filed: Nov. 23, 2021

(65) Prior Publication Data
US 2022/0249672 A1 Aug. 11, 2022

Related U.S. Application Data

(63) Continuation of application No. 16/080,812, filed as application No. PCT/US2017/020642 on Mar. 3, 2017, now Pat. No. 11,298,423.

(60) Provisional application No. 62/460,449, filed on Feb. 17, 2017, provisional application No. 62/303,591, filed on Mar. 4, 2016.

(51) Int. Cl.
| | |
|---|---|
| *A61K 9/10* | (2006.01) |
| *A61K 9/06* | (2006.01) |
| *A61K 47/30* | (2006.01) |
| *A61K 35/19* | (2015.01) |
| *A61L 15/22* | (2006.01) |
| *A61L 15/44* | (2006.01) |
| *A61K 47/36* | (2006.01) |
| *A61K 9/00* | (2006.01) |
| *A61L 27/26* | (2006.01) |
| *A61K 38/18* | (2006.01) |
| *A61L 27/54* | (2006.01) |
| *A61P 9/10* | (2006.01) |
| *A61K 35/16* | (2015.01) |
| *A61K 38/17* | (2006.01) |
| *A61K 38/19* | (2006.01) |
| *A61K 47/34* | (2017.01) |
| *A61K 47/42* | (2017.01) |
| *A61L 15/40* | (2006.01) |
| *A61L 27/18* | (2006.01) |
| *A61L 27/20* | (2006.01) |
| *A61L 27/22* | (2006.01) |
| *A61L 27/36* | (2006.01) |
| *A61L 27/52* | (2006.01) |
| *A61L 27/56* | (2006.01) |
| *A61L 31/04* | (2006.01) |

(Continued)

(52) U.S. Cl.
CPC ............ *A61K 47/36* (2013.01); *A61K 9/0019* (2013.01); *A61K 9/06* (2013.01); *A61K 35/16* (2013.01); *A61K 35/19* (2013.01); *A61K 38/177* (2013.01); *A61K 38/18* (2013.01); *A61K 38/1825* (2013.01); *A61K 38/195* (2013.01); *A61K 47/34* (2013.01); *A61K 47/42* (2013.01); *A61L 15/225* (2013.01); *A61L 15/40* (2013.01); *A61L 15/44* (2013.01); *A61L 27/18* (2013.01); *A61L 27/20* (2013.01); *A61L 27/225* (2013.01); *A61L 27/26* (2013.01); *A61L 27/3616* (2013.01); *A61L 27/52* (2013.01); *A61L 27/54* (2013.01); *A61L 27/56* (2013.01); *A61L 31/041* (2013.01); *A61L 31/042* (2013.01); *A61L 31/046* (2013.01); *A61L 31/145* (2013.01); *A61L 31/16* (2013.01); *A61P 9/10* (2018.01); *A61L 2300/25* (2013.01); *A61L 2300/252* (2013.01); *A61L 2300/414* (2013.01); *A61L 2300/418* (2013.01); *A61L 2400/04* (2013.01); *A61L 2430/20* (2013.01)

(58) Field of Classification Search
CPC ........ A61K 9/0019; A61K 9/06; A61K 35/16; A61K 35/19; A61K 38/177; A61K 38/1825; A61K 38/195; A61K 47/34; A61K 47/42; A61L 15/225; A61L 15/40; A61L 15/44; A61L 27/18; A61L 27/20
See application file for complete search history.

(56) References Cited

U.S. PATENT DOCUMENTS

| 9,023,972 B2 | 5/2015 | Chu et al. |
| 9,095,619 B2 | 8/2015 | Kleiner et al. |

(Continued)

FOREIGN PATENT DOCUMENTS

WO 2011091411 A2 7/2011

OTHER PUBLICATIONS

Purcell et al., "Injectable and bioresponsive hydrogels for on-demand matrix metalloproteinase inhibition," Nature Materials 13:653-661 (2014) (Year: 2014).*

(Continued)

*Primary Examiner* — Julie Ha
*Assistant Examiner* — Kristina M Hellman
(74) *Attorney, Agent, or Firm* — The Webb Law Firm

(57) ABSTRACT

Compositions are provided herein comprising a coacervate of a polycationic polymer, a polyanionic polymer, and platelet-rich plasma and/or serum, or a fraction or concentrate thereof. The composition is useful in wound healing. Compositions also are provided that comprise a hydrogel comprising TIMP-3; and a complex of a polycationic polymer, a polyanionic polymer, FGF-2 and SDF-1α embedded in the hydrogel, which is useful in treating a myocardial infarction.

20 Claims, 19 Drawing Sheets
Specification includes a Sequence Listing.

(51) Int. Cl.
A61L 31/14 (2006.01)
A61L 31/16 (2006.01)

(56) References Cited

U.S. PATENT DOCUMENTS

2007/0110813 A1 5/2007 Ingenito et al.
2013/0071930 A1 3/2013 Chu et al.
2014/0148395 A1 5/2014 Burdick et al.
2014/0287061 A1 9/2014 Landolina

OTHER PUBLICATIONS

Abbott et al., "Stromal Cell Derived Factor-1alpha Plays a Critical Role in Stem Cell Recruitment to the Heart After Myocardial Infarction but Is Not Sufficient to Induce Homing in the Absence of Injury", Circulation; 2004, pp. 3300-3305, vol. 110.
Aplin et al., "The Aortic Ring Model of Angiogenesis", Methods in Enzymology, 2008, pp. 119-136, vol. 443.
Ashikari-Hada et al., "Characterization of Growth Factor-binding Structures in Heparin/Heparan Sulfate Using an Octasaccharide Library", The Journal of Biological Chemistry, 2004, pp. 12346-12354, vol. 279(13).
Awada et al., "Dual Delivery of Vascular Endothelial Growth Factor and Hepatocyte Growth Factor Coacervate Displays Strong Angiogenic Effects", Macromolecular Bioscience, 2014, pp. 679-686, vol. 14.
Awada et al., "Sequential delivery of angiogenic growth factors improves revascularization and heart function after myocardial infarction", Journal of Controlled Release, 2015, pp. 7-17, vol. 207.
Awada et al., "Factorial Design of Experiments to Optimize Multiple Protein Delivery for Cardiac Repair", ACS Biomaterials Science & Engineering, 2016, pp. 879-886, vol. 2.
Awada et al., "A single injection of protein-loaded coacervate-gel significantly improves cardiac function post Infarction", Biomaterials, 2017, pp. 65-80, vol. 125.
Balasubramanian et al., "b3 Integrin in Cardiac Fibroblast Is Critical for Extracellular Matrix Accumulation during Pressure Overload Hypertrophy in Mouse", PLoS One, 2012, p. e45076, vol. 7(9).
Banquet et al., "Arteriogenic Therapy by Intramyocardial Sustained Delivery of a Novel Growth Factor Combination Prevents Chronic Heart Failure", Circulation, 2011, pp. 1059-1069, vol. 124(9).
Bergmann et al., "Evidence for Cardiomyocyte Renewal in Humans", Science, 2009, pp. 98-102, vol. 324.
Bersell et al., "Neuregulin 1/ErbB4 Signaling Induces Cardiomyocyte Proliferation and Repair of Heart Injury", Cell, 2009, pp. 257-270, vol. 138.
Betsholtz, "Insight into the physiological functions of PDGF through genetic studies in mice", Cytokine & Growth Factor Reviews, 2004, pp. 215-228, vol. 15.
Bhan et al., "High-frequency speckle tracking echocardiography in the assessment of left ventricular function and remodeling after murine myocardial infarction", Am J Physiol Heart Circ Physiol., 2014, pp. H1371-H1383, vol. 306.
Black et al., "Protein Encapsulation via Polypeptide Complex Coacervation", ACS Macro Letters, 2014, pp. 1088-1091, vol. 3.
Braun et al., "Breaking the Silence: Stimulating Proliferation of Adult Cardiomyocytes", Developmental Cell, 2009, pp. 151-153, vol. 17.
Brett, "A Review of Collagen and Collagen-based Wound Dressings", Wounds, 2008, pp. 347-356, vol. 20.
Brudno et al., "Enhancing microvascular formation and vessel maturation through temporal control over multiple pro-angiogenic and pro-maturation factors", Biomaterials, 2013, pp. 9201-9209, vol. 34.
Capila et al., "Heparin-Protein Interactions", Angewandte Chemie International Edition English, 2002, pp. 390-412, vol. 41.
Carmeliet et al., "Molecular mechanisms and clinical applications of angiogenesis", Nature, 2011, pp. 298-307, vol. 473(7347).

Chen et al., "Release characteristics and bioactivity of gelatin-tricalcium phosphate membranes covalently Immobilized with nerve growth factors", Biomaterials, 2005, pp. 6579-6587, vol. 26.
Chen et al., "Spatio-temporal VEGF and PDGF Delivery Patterns Blood Vessel Formation and Maturation", Pharmaceutical Research, 2007, pp. 258-264, vol. 24(2).
Chen et al., "Toward delivery of multiple growth factors in tissue engineering", Biomaterials, 2010, pp. 6279-6308, vol. 31.
Chen et al., "Human pericytes for ischemic heart repair", Stem Cells, 2013, pp. 305-316, vol. 31(2).
Chen et al., "Controlled Dual Delivery of Fibroblast Growth Factor-2 and Interleukin-10 by Heparin-based Coacervate Synergistically Enhances Ischemic Heart Repair", Biomaterials, 2015, pp. 138-151, vol. 72.
Chen et al., "Human Myocardial Pericytes: Multipotent Mesodermal Precursors Exhibiting Cardiac Specificity", Stem Cells, 2015, pp. 557-573, vol. 33(2).
Choi et al., "Dual Growth Factor Delivery Using Biocompatible Core-Shell Microcapsules for Angiogenesis", Small, 2013, pp. 1-9, vol. 9(20).
Chu et al., "A [polycation heparin] complex releases growth factors with enhanced bioactivity", Journal of Controlled Release, 2011, pp. 157-163, vol. 150 (2011).
Chu et al., "Injectable fibroblast growth factor-2 coacervate for persistent angiogenesis", PNAS, 2011, pp. 13444-13449, vol. 108(33).
Chu et al., "Design, synthesis, and biocompatibility of an arginine-based polyester", Biotechnology Progress, 2012, pp. 257-264, vol. 28.
Chu et al., "Therapeutic angiogenesis: controlled delivery of angiogenic factors", Therapeutic Delivery, 2012, pp. 693-714, vol. 3(6).
Chu et al., "The effect of a heparin-based coacervate of fibroblast growth factor-2 on scarring in the infarcted myocardium", Biomaterials, 2013, pp. 1747-1756, vol. 34(6).
Cochain et al., "Angiogenesis in the Infarcted Myocardium", Antioxidants and Redox Signaling, 2013, pp. 1100-1113, vol. 18(9).
Cooke et al., "Nitric Oxide and Angiogenesis", Circulation, 2002, pp. 2133-2135, vol. 105.
Crawley, "The Coagulation Cascade and Its Regulation," 2011, Textbook of Pulmonary Vascular Disease, eds. Yuan et al., Chap. 23, pp. 357-370.
Czarkowska-Paczek et al., "The serum levels of growth factors: PDGF, TGF-beta and VEGF are increased after strenuous physical exercise," Journal of Physiology and Pharmacology, 2006, pp. 189-197, vol. 57(2).
Davies et al., "Sustaining Neovascularization of a Scaffold Through Staged Release of Vascular Endothelial Growth Factor-A and Platelet-Derived Growth Factor-BB", Tissue Engineering Part A, 2012, pp. 26-34, vol. 18(1)(2).
De Jong et al., "Dimethylmethylene Blue-Based Spectrophotometry of Glycosaminoglycans in Untreated Urine: a Rapid Screening Procedure for Mucopolysaccharidoses", Clinical Chemistry, 1989, pp. 1472-1477, vol. 35(7).
Deblois et al., "Heparin-fibroblast growth factorfibrin complex: in vitro and in vivo applications to collagen-based materials", Biomaterials, 1994, pp. 665-672, vol. 15(9).
Deveza et al., "Therapeutic Angiogenesis for Treating Cardiovascular Diseases", Theranostics, 2012, pp. 801-814, vol. 2(8).
Dhingra et al., "IL-10 attenuates TNF-induced NF B pathway activation and cardiomyocyte apoptosis", Cardiovascular Research, 2009, pp. 59-66, vol. 82.
Dhurat et al., "Principles and Methods of Preparation of Platelet-Rich Plasma: A Review and Author's Perspective", Journal of Cutaneous and Aesthetic Surgery, 2014, pp. 189-197, vol. 7(4).
Dobner et al., "A Synthetic Non-degradable Polyethylene Glycol Hydrogel Retards Adverse Post-infarct Left Ventricular Remodeling", Journal of Cardiac Failure, 2009, pp. 629-636, vol. 15(7).
Drinnan et al., "Multimodal release of transforming growth factor-beta1 and the BB isoform of platelet derived growth factor from PEGylated fibrin gels", Journal of Controlled Release, 2010, pp. 180-186, vol. 147.

(56) References Cited

OTHER PUBLICATIONS

Driver et al., "A Prospective, Randomized, Controlled Trial of Autologous Platelet-Rich Plasma Gel for the Treatment of Diabetic Foot Ulcers," Ostomy Wound Management, 2006, pp. 68-87, vol. 52(6).
Eckhouse et al., "Local Hydrogel Release of Recombinant TIMP-3 Attenuates Adverse Left Ventricular Remodeling After Experimental Myocardial Infarction", Science Translational Medicine, 2014, p. 223ra221, vol. 6(223).
Eklund et al., "Tie receptors and their angiopoietin ligands are context-dependent regulators of vascular remodeling", Experimental Cell Research, 2006, pp. 630-641, vol. 312.
Eming et al., "Wound repair and regeneration: Mechanisms, signaling, and translation", Science Translational Medicine, 2014, p. 265sr266, vol. 6(265).
Ensembl: ENSG00000102265, Zerbino, D. R., et al. Ensembl 2018, Nucleic Acids Research, vol. 46, Issue D1, Jan. 4, 2018, pp. D754-D761.
Ensembl: ENSG00000107562, Zerbino, D. R., et al. Ensembl 2018, Nucleic Acids Research, vol. 46, Issue D1, Jan. 4, 2018, pp. D754-D761.
Ensembl: ENSG00000138685, Zerbino, D. R., et al. Ensembl 2018, Nucleic Acids Research, vol. 46, Issue D1, Jan. 4, 2018, pp. D754-D761.
Lee et al., "Human progenitor cell recruitment via SDF-1alpha coacervate-laden PGS vascular grafts", Biomaterials, 2013, pp. 9877-9885, vol. 34.
Li et al., "The Role of Therapeutic Angiogenesis in Tissue Repair and Regeneration", Advances in Skin and Wound Care, 2005, pp. 491-500, vol. 18(9).
Li et al., "Sustained Release of Bone Morphogenetic Protein 2 via Coacervate Improves the Osteogenic Potential of Muscle-Derived Stem Cells", Stem Cells Translational Medicine, 2013, pp. 667-677, vol. 2(9).
Long et al., "Complex Coacervate as a Protein Delivery Vehicle", Poster Presentation, McGowan Retreat, Mar. 16, 2016.
Lubinski et al., "Speckle Tracking Methods for Ultrasonic Elasticity Imaging Using Short-Time Correlation", IEEE Transactions on Ultrasonics, Ferroelectrics, and Frequency Control, 1999, pp. 82-96, vol. 46(1).
Lui et al., "Cardiovascular regenerative therapeutics via synthetic paracrine factor modified mRNA", Stem Cell Research, 2014, pp. 693-704, vol. 13.
Madduri et al., "Effect of controlled co-delivery of synergistic neurotrophic factors on early nerve regeneration in rats", Biomaterials, 2010, pp. 8402-8409, vol. 31.
Malliaras et al., "Cardiomyocyte proliferation vs progenitor cells in myocardial regeneration: The debate continues", Global Cardiology Science & Practice, 2013, pp. 303-315, vol. 37.
Manning et al., "In vivo assessment of LV mass in mice using high-frequency cardiac ultrasound: necropsy validation", American Journal of Physiology, 1994, pp. H1672-H1675, vol. 266(4).
MARTINEZ-ZAPATA., "Autologous platelet-rich plasma for treating chronic wounds", The Cochrane Database of Systematic Reviews, 2016, p. CD006899, Issue 5.
Maulik et al., "Growth factor/s and cell therapy in myocardial regeneration", Journal of Molecular and Cellular Cardiology, 2008, pp. 219-227, vol. 44.
Middleton et al., "Evaluation of the effects of platelet-rich plasma (PRP) therapy involved in the healing of sports- related soft tissue injuries", The Iowa Orthopaedic Journal, 2012, pp. 150-163, vol. 32.
Mohtaram et al., "Biomaterial-based drug delivery systems for the controlled release of neurotrophic factors", Biomedical Materials, 2013, p. 022001, vol. 8.
Moore et al., "Interleukin-10 and the interleukin-10 receptor", Annual Review of Immunology, 2001, 683-765, vol. 19.
Morbidelli et al., "Nitric oxide mediates mitogenic effect of VEGF on coronary venular endothelium", American Journal of Physiology, 1996, pp. H411-H415, vol. 270.

Mulloy et al., "Conformation and dynamics of heparin and heparan sulfate", Glycobiology, 2000, pp. 1147-1156, vol. 10(11).
Mussano et al., "Cytokine, chemokine, and growth factor profile of platelet-rich plasma", Platelets, 2016, pp. 467-471, vol. 27(5).
Nagai et al., "Gene and cytokine therapy for heart failure: molecular mechanisms in the improvement of cardiac function", Am J Physiol Heart Circ Physiol, 2012, pp. H501-H512, vol. 303.
O'Donnell et al., "Internal displacement and strain imaging using ultrasonic speckle tracking", IEEE Transactions on Ultrasonics, Ferroelectrics, and Frequency Control, 1994, pp. 314-325, vol. 41(3).
Ogle et al., "Distilling complexity to advance cardiac tissue engineering", Science Translational Medicine, 2016, p. 342ps313, vol. 8(342).
Online Mendelian Inheritance in Man, OMIM (TM). Johns Hopkins University, Baltimore, MD. MIM No. 134920: Oct. 7, 2016: Retrieved from http://www.ncbi.nlm.nih.gov/omim/.
Online Mendelian Inheritance in Man, OMIM (TM). Johns Hopkins University, Baltimore, MD. MIM No. 305370: Oct. 14, 2010: Retrieved from http://www.ncbi.nlm.nih.gov/omim/.
Online Mendelian Inheritance in Man, OMIM (TM). Johns Hopkins University, Baltimore, MD. MIM No. 600835: Jan. 19, 2016: Retrieved from http://www.ncbi.nlm.nih.gov/omim/.
Papanas et al., "Becaplermin gel in the treatment of diabetic neuropathic foot ulcers", Clinical Interventions in Aging, 2008, pp. 233-240, vol. 3(2).
Pellegrini, "Role of heparan sulfate in fibroblast growth factor signalling: a structural view", Current Opinion in Structural Biology, 2001, pp. 629-634, vol. 11.
Pinto et al., "Macrophages in cardiac homeostasis, injury responses and progenitor cell mobilisation", Stem Cell Research, 2014, pp. 705-714, vol. 13.
Pollick et al., "Echocardiographic and Cardiac Doppler Assessment of Mice", Journal of the American Society of Echocardiography, 1995, pp. 602-610, vol. 8.
Porter et al., "Simvastatin reduces human atrial myofibroblast proliferation independently of cholesterol lowering via Inhibition of RhoA", Cardiovascular Research, 2004, pp. 745-755, vol. 61.
Qian et al., "In vivo reprogramming of murine cardiac fibroblasts into induced cardiomyocytes", Nature, 2012, pp. 593-598, vol. 485.
Rajangam et al., "Heparin binding nanostructures to promote growth of blood vessels", Nano Letters, 2006, pp. 2086-2090, vol. 6(9).
Rauck et al., "Biocompatibility of a Coacervate-Based Controlled Release System for Protein Delivery to the Injured Spinal Cord", Acta Biomater., 2015, pp. 204-211, vol. 11.
Richardson et al., "Polymeric system for dual growth factor delivery", Nature Biotechnology, 2001, pp. 1029-1034, vol. 19.
Ruvinov et al., "The promotion of myocardial repair by the sequential delivery of IGF-1 and HGF from an injectable alginate biomaterial in a model of acute myocardial infarction", Biomaterials, 2011, pp. 565-578, vol. 32.
Sager et al., "RNAi targeting multiple cell adhesion molecules reduces immune cell recruitment and vascular Inflammation after myocardial infarction", Science Translational Medicine, 2016, 342ra380, vol. 8(342).
Sakiyama-Elbert, "Incorporation of heparin into biomaterials", Acta Biomaterialia, 2014, pp. 1581-1587, vol. 10.
Salek-Ardakani et al., "Heparin and heparan sulfate bind interleukin-10 and modulate its activity", Blood, 2000, pp. 1879-1888, vol. 96.
Schoen et al., "The Heart", Robbins & Cotran Pathologic Basis of Disease, 2010, pp. 555-618.
Schultz et al., "Interactions between extracellular matrix and growth factors in wound healing", Wound Repair and Regeneration, 2009, pp. 153-162, vol. 17.
Segers et al., "Protein Therapeutics for Cardiac Regeneration after Myocardial Infarction", Journal of Cardiovasc. Trans. Res., 2010, pp. 469-477, vol. 3.
Senyo et al., "Cardiac regeneration based on mechanisms of cardiomyocyte proliferation and differentiation", Stem Cell Research, 2014, pp. 532-541, vol. 13.

(56) References Cited

OTHER PUBLICATIONS

Shin et al., "Co-delivery of Vascular Endothelial Growth Factor and Angiopoietin-1 Using Injectable Microsphere/ Hydrogel Hybrid Systems for Therapeutic Angiogenesis", Pharmaceutical Research, 2013, pp. 2157-2165, vol. 30.
Shin et al., "Sequential delivery of TAT-HSP27 and VEGF using microsphere/hydrogel hybrid systems for therapeutic angiogenesis", Journal of Controlled Release, 2013, pp. 38-45, vol. 166.
Silva et al., "Growth Factor Delivery Approaches in Hydrogels", Biomacromolecules, 2009, pp. 9-18;, vol. 10.
Slawson et al., "Cardiac MRI of the Normal and Hypertrophied Mouse Heart", Magnetic Resonance in Medicine, 1998, pp. 980-987, vol. 39.
Sternlicht et al., "How Matrix Metalloproteinases Regulate Cell Behavior", Annual Review of Cell and Developmental Biology, 2001, pp. 463-516, vol. 17.
Stumpf et al., "Interleukin-10 improves left ventricular function in rats with heart failure subsequent to myocardial Infarction", European Journal of Heart Failure, 2008, pp. 733-739, vol. 10.
Sun et al., "Angiotensin II, Transforming Growth Factor-beta1 and Repair in the Infarcted Heart", J Mol Cell Cardiol., 1998, pp. 1559-1569, vol. 30.
Sun et al., "Sustained Release of Multiple Growth Factors from Injectable Polymeric System as a Novel Therapeutic Approach Towards Angiogenesis", Pharmaceutical Research, 2010, pp. 264-271, vol. 27(2).
Sutton et al., "Left Ventricular Remodeling After Myocardial Infarction: Pathophysiology and Therapy", Circulation, 2000, pp. 2981-2988, vol. 101.
Svystonyuk et al., "Fibroblast growth factor-2 regulates human cardiac myofibroblast-mediated extracellular matrix remodeling", Journal of Translational Medicine, 2015, pp. 1-11, vol. 13(147).
Entrez Gene: 2247, National Center for Biotechnology Information (NCBI)[Internet]. Bethesda (MD): National Library of Medicine (US), National Center for Biotechnology Information; [1988]—[Oct. 5, 2018]. Available from: https://www.ncbi.nlm.nih.gov/.
Entrez Gene: 6387, National Center for Biotechnology Information (NCBI)[Internet]. Bethesda (MD): National Library of Medicine (US), National Center for Biotechnology Information; [1988]—[Oct. 5, 2018]. Available from: https://www.ncbi.nlm.nih.gov/.
Entrez Gene: 7076, National Center for Biotechnology Information (NCBI)[Internet]. Bethesda (MD): National Library of Medicine (US), National Center for Biotechnology Information; [1988]—[Oct. 5, 1988]. Available from: https://www.ncbi.nlm.nih.gov/.
Epstein et al., "Angiogenesis Therapy: Amidst the Hype, the Neglected Potential for Serious Side Effects", Circulation, 2001, pp. 115-119, vol. 104.
Eton et al., "Myocardial and interstitial matrix metalloproteinase activity after acute myocardial infarction in pigs," American Journal of Physiology-Heart and Circulatory Physiology, 2001, pp. H987-H994, vol. 281(3).
Ferguson et al., "Prophylactic administration of avotermin for improvement of skin scarring: three double-blind, placebo-controlled, phase I/II studies," Lancet, 2009, pp. 1264-1274, vol. 373.
Ferrara et al., "The biology of VEGF and its receptors", Nature Medicine, 2003, pp. 669-676, vol. 9(6).
Forbes et al, "Preparing the ground for tissue regeneration: from mechanism to therapy", Nature Medicine, 2014, pp. 857-869, vol. 20(8).
Formiga et al., "Angiogenic therapy for cardiac repair based on protein delivery systems", Heart Fail Rev., 2012, pp. 449-473, vol. 17.
Frangogiannis, "Regulation of the inflammatory response in cardiac repair", Circulation Research, 2012, pp. 159-173, vol. 110(1).
Freeman et al., "The effect of sulfation of alginate hydrogels on the specific binding and controlled release of heparin-binding proteins", Biomaterials, 2008, pp. 3260-3268, vol. 29.
Go et al., "The Rat Aortic Ring Assay for In Vitro Study of Angiogenesis", Methods in Molecular Medicine, 2003, pp. 59-64, vol. 85.
Go et al., "Heart Disease and Stroke Statistics—2014 Update: A Report From the American Heart Association", Circulation, 2014, pp. e28-e292, vol. 129(3).
Go et al., "Executive Summary: Heart Disease and Stroke Statistics—2014 Update: A Report From the American Heart Association", Circulation, 2014, pp. 399-410, vol. 129(3).
Greenberg et al., "A role for VEGF as a negative regulator of pericyte function and vessel maturation", Nature, 2008, pp. 809-813, vol. 456.
Grey et al., "Wound assessment," BMJ, 2006, pp. 285-288, vol. 332.
Gullestad et al., "Immunomodulating Therapy With Intravenous Immunoglobulin in Patients With Chronic Heart Failure", Circulation, 2001, pp. 220-225, vol. 103(2).
Hanft et al., "Phase I trial on the safety of topical rhVEGF on chronic neuropathic diabetic foot ulcers," Journal of Wound Care, 2008, pp. 30-37, vol. 17(1).
Iao et al., "Angiogenic and cardiac functional effects of dual gene transfer of VEGF-A(sub)165 and PDGF-BB after myocardial infarction", Biochemical and Biophysical Research Communications, 2004, pp. 292-296, vol. 322.
Hao et al., "Angiogenic effects of sequential release of VEGF-A165 and PDGF-BB with alginate hydrogels after myocardial infarction", Cardiovascular Research, 2007, pp. 178-185, vol. 75.
Hastings et al., "Drug and cell delivery for cardiac regeneration", Advanced Drug Delivery Reviews, 2015, pp. 85-106, vol. 84.
Henry et al., "Intracoronary administration of recombinant human vascular endothelial growth factor to patients with coronary artery disease", American Heart Journal, 2001, pp. 872-880, vol. 142(5).
HGNC: 10672, HGNC Database, HUGO Gene Nomenclature Committee (HGNC), European Molecular Biology Laboratory, European Bioinformatics Institute, Wellcome Genome Campus, Hinxton, Cambridgeshire, CB10 1SD, UK; www.genenames.org, retrieved Oct. 2018.
HGNC: 11820, HGNC Database, HUGO Gene Nomenclature Committee (HGNC), European Molecular Biology aboratory, European Bioinformatics Institute, Wellcome Genome Campus, Hinxton, Cambridgeshire, CB10 1SD, UK; www.genenames.org, retrieved Oct. 2018.
HGNC: 3676, HGNC Database, HUGO Gene Nomenclature Committee (HGNC), European Molecular Biology Laboratory, European Bioinformatics Institute, Wellcome Genome Campus, Hinxton, Cambridgeshire, CB10 1SD, UK; www.genenames.org, retrieved Oct. 2018.
Hsieh et al., "Controlled delivery of PDGF-BB for myocardial protection using injectable self-assembling peptide hanofibers", The Journal of Clinical Investigation, 2006, pp. 237-248, vol. 116(1).
Huhn et al., "Pharmacodynamics of subcutaneous recombinant human interleukin-10 in healthy volunteers", Clin Pharmacol Ther., 1997, pp. 171-180, vol. 62(2).
Hwang et al., "Improving regenerating potential of the heart after myocardial infarction: Factor-based approach", Life Sciences, 2010, pp. 461-472, vol. 86.
Hwang et al., "The Combined Administration of Multiple Soluble Factors in the Repair of Chronically Infarcted Rat Myocardium," Journal of Cardiovascular Pharmacology, 2011, pp. 282-286, vol. 57(3).
Iyer et al., "Role of Interleukin 10 Transcriptional Regulation in Inflammation and Autoimmune Disease", Crit Rev Immunol., 2012, pp. 23-63, vol. 32(1).
Jiang et al., "Design of a composite biomaterial system for tissue engineering applications," 2014, Acta Biomaterialia, pp. 1177-1186, vol. 10.
Jiao et al., "Chemical Structures and Bioactivities of Sulfated Polysaccharides from Marine Algae," Mar. Drugs, 2011, pp. 196-223, vol. 9.
Johnson et al., "Controlled Delivery of Sonic Hedgehog Morphogen and Its Potential for Cardiac Repair", PLOS One, 2013, pp. e63075, vol. 8(5).

(56) References Cited

OTHER PUBLICATIONS

Johnson et al., "Controlled delivery of heparin-binding EGF-like growth factor yields fast and comprehensive wound healing", Journal of Controlled Release, 2013, pp. 124-129, vol. 166.
Johnson et al., "Lysine-based polycation heparin coacervate for controlled protein delivery", Acta Biomaterialia, 2014, pp. 40-46, vol. 10.
Johnson et al., "Coacervate delivery systems for proteins and small molecule drugs", Expert Opinion on Drug Delivery, 2014, pp. 1829-1832, vol. 11(12).
Johnson et al., "Coacervate delivery of HB-EGF accelerates healing of type 2 diabetic wounds," Wound Repair and Regeneration, 2015, pp. 591-600, vol. 23.
Kim et al., "The enhancement of mature vessel formation and cardiac function in infarcted hearts using dual growth factor delivery with self-assembling peptides", Biomaterials, 2011, pp. 6080-6088, vol. 32(26).
Kim et al., "Co-delivery of platelet-derived growth factor (PDGF-BB) and bone morphogenic protein (BMP-2) coated onto heparinized titanium for improving osteoblast function and osteointegration", Journal of Tissue Engineering and Regenerative Medicine, 2015, pp. E219-E228, vol. 9.
Kinsella et al., "Interactions of putative heparin-binding domains of basic fibroblast growth factor and its receptor, FGFR-1, with heparin using synthetic peptides", Glycoconjugate Journal, 1998, pp. 419-422, vol. 15(4).
Kis et al., "Second window of protection following myocardial preconditioning: an essential role for PI3 kinase and 570S6 kinase," Journal of Molecular and Cellular Cardiology, 2003, pp. 1063-1071, vol. 35.
Kishimoto et al., "Novel Experimental and Clinical Therapeutic Uses of Low-Molecular-Weight Heparin/Protamine Microparticles", Pharmaceutics, 2012, pp. 42-57, vol. 4.
Krishnamurthy et al., "IL-10 inhibits inflammation and attenuates left ventricular remodeling after myocardial infarction via activation of STAT-3 and suppression of HuR", Circ Res., 2009, pp. e9-18, vol. 104(2).
Kuhn et al., "Periostin induces proliferation of differentiated cardiomyocytes and promotes cardiac repair", Nature Medicine, 2007, pp. 962-969, vol. 13(8).
Kurrelmeyer et al., "Cardiac Remodeling as a Consequence and Cause of Progressive Heart Failure", Clinical Cardiology, 1998, pp. 14-19, vol. 21(Suppl. I).
Lambert et al., "Macrophage roles following myocardial infarction", International Journal of Cardiology, 2008, pp. 147-158, vol. 130.
Latet et al., "The cellular immune system in the post-myocardial infarction repair process", International Journal of Cardiology, 2015, pp. 240-247, vol. 179.
Lee et al., "VEGF Gene Delivery to Myocardium: Deleterious Effects of Unregulated Expression", Circulation, 2000, pp. 898-901, vol. 102.
Lee et al., "Growth factor delivery-based tissue engineering: general approaches and a review of recent developments", Journal of The Royal Society Interface, 2011, pp. 153-170, vol. 8.
Lee et al., "Bone regeneration with low dose BMP-2 amplified by biomimetic supramolecular nanofibers within collagen scaffolds," Biomaterials, 2013, pp. 452-459, vol. 34.
Takabayashi et al., "Platelet-rich plasma-containing fragmin-protamine micro-nanoparticles promote epithelialization and angiogenesis in split-thickness skin graft donor sites," Journal of Surgical Research, 2015, pp. 483-491, vol. 193.
Takehara et al., "Controlled Delivery of Basic Fibroblast Growth Factor Promotes Human Cardiosphere-Derived Cell Engraftment to Enhance Cardiac Repair for Chronic Myocardial Infarction", Journal of the American College of Cardiology, 2008, pp. 1858-1865; vol. 52(23).
Takikawa et al., "PRP&F/P MPs Improved Survival of Dorsal Paired Pedicle Skin Flaps in Rats," Journal of Surgical Research, 2011, pp. 189-196, vol. 170.
Tang et al., "The enhancement of endothelial cell therapy for angiogenesis in hindlimb ischemia using hyaluronan", 2011, Biomaterials, pp. 75-86, vol. 32.
Tang et al., "VEGF/SDF-1 promotes cardiac stem cell mobilization and myocardial repair in the infarcted heart", Cardiovascular Research, 2011, pp. 402-411, vol. 91.
Tayalia et al., "Controlled Growth Factor Delivery for Tissue Engineering", Advanced Materials, 2009, pp. 3269-3285, vol. 21.
Tengood et al., "Sequential delivery of vascular endothelial growth factor and sphingosine 1-phosphate for angiogenesis", Biomaterials, 2010, pp. 7805-7812, vol. 31.
Tengood et al., "Sequential Delivery of Basic Fibroblast Growth Factor and Platelet-Derived Growth Factor for Angiogenesis", Tissue Engineering: Part A, 2011, pp. 1181-1189, vol. 17(9)(10).
Tian et al., "Inhibiting Matrix Metalloproteinase by Cell-Based Timp-3 Gene Transfer Effectively Treats Acute and Chronic Ischemic Cardiomyopathy", Cell Transplantation, 2012, pp. 1039-1053, vol. 21.
Tsai, "von Willebrand Factor, Shear Stress, and ADAMTS13 in Hemostasis and Thrombosis", ASAIO Journal, 2012, pp. 163-169, vol. 58.
Tsang et al., "Postconditioning: A Form of "Modified Reperfusion" Protects the Myocardium by Activating the Phosphatidylinositol 3-Kinase-Akt Pathway", Circulation Research, 2004, pp. 230-232, vol. 95.
Turner et al., "Chronic beta2-adrenergic receptor stimulation increases proliferation of human cardiac fibroblasts via an autocrine mechanism", Cardiovascular Research, 2003, pp. 784-792, vol. 57.
Uchinaka et al., "Tissue Inhibitor of Metalloproteinase-1 and -3 Improves Cardiac Function in an Ischemic Cardiomyopathy Model Rat", Tissue Engineering:Part A, 2014, pp. 3073-3084, vol. 20(21)(22).
UniProtKB: P01033, UniProt: the universal protein knowledgebase Nucleic Acids Res. 45: D158-D169 (2017), Accession No.
UniProtKB: P09038, UniProt: the universal protein knowledgebase Nucleic Acids Res. 45: D158-D169 (2017), Accession No.
UniProtKB: P48061, UniProt: the universal protein knowledgebase Nucleic Acids Res. 45: D158-D169 (2017), Accession No.
Van Der Zee et al., "Vascular Endothelial Growth Factor/Vascular Permeability Factor Augments Nitric Oxide Release From Quiescent Rabbit and Human Vascular Endothelium", Circulation, 1997, pp. 1030-1037, vol. 95.
Van Rugge et al., "Magnetic Resonance Imaging During Dobutamine Stress for Detection and Localization of Coronary Artery Disease: Quantitative Wall Motion Analysis Using a Modification of the Centerline Method", Circulation, 1994, pp. 127-138, vol. 90.
Vasita et al., "Growth factor-delivery systems for tissue engineering: a materials perspective", Expert Rev. Med. Devices, 2006, pp. 29-47, vol. 3(1).
Visse et al., "Matrix Metalloproteinases and Tissue Inhibitors of Metalloproteinases: Structure, Function, and Biochemistry", Circulation Research, 2003, pp. 827-839, vol. 92.
Vu et al., "Matrix metalloproteinases: effectors of development and normal physiology", Genes & Development, 2000, pp. 2123-2133, vol. 14.
Vu et al., "An autologous platelet-rich plasma hydrogel compound restores left ventricular structure, function and ameliorates adverse remodeling in a minimally invasive large animal myocardial restoration model: A translational approach", Biomaterials, 2015, pp. 27-35, vol. 45.
Wandt et al., "Echocardiographic assessment of ejection fraction in left ventricular hypertrophy", Heart, 1999, pp. 192-198, vol. 82.
Wang et al., "Mitogen-Activated Protein Kinases in Heart Development and Diseases", Circulation, 2007, 1413-1423, vol. 116(12).
Wright et al., "Early healing events in a porcine model of contaminated wounds: effects of nanocrystalline silver on matrix metalloproteinases, cell apoptosis, and healing", Wound Repair Regen., 2002, pp. 141-151, vol. 10.
Yan et al., "Acceleration of Full-thickness Wound Healing in Porcine Model by Autologous Platelet Gel", Wounds, 2007, pp. 79-86, vol. 19(4).
Yang et al., "Enhanced skin wound healing by a sustained release of growth factors contained in platelet-rich plasma", Experimental and Molecular Medicine, 2011, pp. 622-629, vol. 43(11).

(56) References Cited

OTHER PUBLICATIONS

Yu et al., "TIMP-3 Binds to Sulfated Glycosaminoglycans of the Extracellular Matrix", The Journal of Biological Chemistry, 2000, pp. 31226-31232, vol. 275(40).

Yu et al., "Effects of Combination of Angiotensin-Converting Enzyme Inhibitor and Angiotensin Receptor Antagonist on Inflammatory Cellular Infiltration and Myocardial Interstitial Fibrosis After Acute Myocardial Infarction", Journal of the American College of Cardiology, 2001, pp. 1207-1215, vol. 38(4).

Zachary et al., "Therapeutic angiogenesis for cardiovascular disease: biological context, challenges, prospects", Heart, 2010, pp. 181-189, vol. 97.

Zangi et al., "Modified mRNA directs the fate of heart progenitor cells and induces vascular regeneration after myocardial infarction", Nat Biotechnol., 2013, pp. 898-907, vol. 31(10).

Zern et al., "Control Growth Factor Release Using a Self-Assembled [polycation: heparin] Complex", PLoS One, 2010, p. e11017, vol. 5(6).

Zhang et al., "Sequential, timely and controlled expression of hVEGF165 and Ang-1 effectively improves functional angiogenesis and cardiac function in vivo", Gene Therapy, 2013, pp. 893-900, vol. 20.

Zhang et al., "The Potential Use of Allogeneic Platelet-Rich Plasma for Large Bone Defect Treatment: Immunogenicity and Defect Healing Efficacy", Cell Transplant, 2013, pp. 175-187, vol. 22.

Zhao et al., "Efficacy of topical recombinant human platelet-derived growth factor for treatment of diabetic lower-extremity ulcers: Systematic review and meta-analysis", Metabolism: Clinical and Experimental, 2014, pp. 1304-1313, vol. 63.

\* cited by examiner

Saline

Delivery Vehicle

Bolus PRP

HB-PRP Coacervate

Full PRP Coacervate

* p<0.05 vs Saline, ψ p<0.05 vs Sham

A DAPI/F4/80/CD163

\* p<0.05 vs Saline, ψ p<0.05 vs Sham

* p<0.05 vs Saline,  ≠ p<0.05 vs Free

\* $p<0.05$ vs Saline, ≠ $p<0.05$ vs Free, ψ $p<0.05$ vs Sham

PROTECTION AND DELIVERY OF MULTIPLE THERAPEUTIC PROTEINS

CROSS REFERENCE TO RELATED APPLICATIONS

This application is a continuation of U.S. patent application Ser. No. 16/080,812, filed Aug. 29, 2018, which is the United States national phase of International Application No. PCT/US2017/020642 filed Mar. 3, 2017, and claims the benefit of United States Provisional Patent Application Nos. 62/303,591, filed Mar. 4, 2016, and 62/460,449, filed Feb. 17, 2017, each of which is incorporated herein by reference in its entirety.

STATEMENT REGARDING FEDERAL FUNDING

This invention was made with government support under Grant No. IIP1444774, awarded by the National Science Foundation and Grant No. and 1R01NR016436-01, awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 2106851_ST25.txt. The size of the text file is 7,659 bytes, and the text file was created on Feb. 11, 2022.

BACKGROUND

Wound healing (and tissue repair) within the human body is governed by the expression of many cytokines, growth factors, and therapeutic proteins. Many researchers in the past have attempted to improve upon this healing response by administering protein therapies such as Vascular Endothelial Growth Factor (VEGF) and Keratinocyte Growth Factor (KGF). However, these proteins are expensive and have half-lives in the range of minutes, requiring multiple large doses of proteins to show any improvements. This is expensive and has been linked to several adverse side effects. Therefore patients need access to more affordable therapeutic proteins that will not lead to damaging side effects.

Protein therapies have high potential to improve clinical outcomes in the field of tissue regeneration. These proteins, particularly growth factors and cytokines, relay signals between cells and their extracellular environment, providing cues for cells to proliferate, differentiate, migrate or secrete extracellular matrix (ECM) proteins. Supplying exogenous growth factors to injured tissues has the potential to accelerate healing and regeneration of tissues; however, they must be applied in a sustained fashion to show efficacy. Due to very short half-lives, this is not possible with free growth factors, while large doses are cost-prohibitive and often result in undesirable off-target effects. The ideal regenerative therapy would involve a delivery system to extend the bioactive half-lives of naturally-derived exogenous proteins rather than expensive recombinant proteins. Several approaches have been proposed to meet this clinical need, but few have demonstrated success in a clinical setting.

Cutaneous wound healing requires the coordination of many complex processes such as cell proliferation, migration, angiogenesis, and ECM deposition (S. A. Eming, et al., Wound repair and regeneration: mechanisms, signaling, and translation, *Sci Transl Med*, 6 (2014) 265sr266). Each of these processes relies on a specific set of signaling cytokines and growth factors. Wounds are typically able to resolve themselves and close over time, however comorbidities such as diabetes and obesity can impair the healing response and result in a chronic non-healing wound. Chronic wounds are often the result of deficient growth factor signaling or reduced sensitivity to growth factors and require the use of advanced therapies. This contributes to the expanding $15 billion market for wound care products in the United States. Even the most advanced wound care options currently available require many treatments, are often unsuccessful and result in 185,000 limb amputations performed in the United States each year as a result of non-healing wounds. New approaches addressing the deficient growth factor regulation of chronic wounds are urgently needed.

Growth factors have been assessed for therapeutic benefit in wound applications for more than forty years. Despite thorough evaluation of more than a dozen different growth factors, only human platelet-derived growth factor (PDGF) has received approval for clinical treatment of diabetic ulcers. Under the trade name REGRANEX®, the PDGF gel promotes epithelial cell and fibroblast migration and a meta-analysis of 6 clinical trials reveals that overall the treatment is efficacious (X. H. Zhao, et al., Efficacy of topical recombinant human platelet-derived growth factor for treatment of diabetic lower-extremity ulcers: Systematic review and meta-analysis, *Metabolism: clinical and experimental*, 63 (2014) 1304-1313). However, this has not necessarily translated to significant clinical usage, in part due to its high cost and poor reputation among clinicians (N. Papanas, et al., Becaplermin gel in the treatment of diabetic neuropathic foot ulcers, *Clinical interventions in aging*, 3 (2008) 233-240). Other notable candidates that have shown moderately positive results in clinical trials include vascular endothelial growth factor (VEGF) for neuropathic foot ulcers (J. R. Hanft, et al., Phase I trial on the safety of topical rhVEGF on chronic neuropathic diabetic foot ulcers, *Journal of wound care*, 17 (2008) 30-32, 34-37), fibroblast growth factor (FGF-1) for deep burns (B. Ma, et al., Randomized, multicenter, double-blind, and placebo-controlled trial using topical recombinant human acidic fibroblast growth factor for deep partial-thickness burns and skin graft donor site, *Wound Repair Regen*, 15 (2007) 795-799), and transforming growth factor-beta 3 (TGF-β3) for scar prevention (M. W. Ferguson, et al., Prophylactic administration of avotermin for improvement of skin scarring: three double-blind, placebo-controlled, phase I/II studies, *Lancet*, 373 (2009) 1264-1274), among others, though none have progressed further, presumably over concerns of a similar fate to REGRANEX®. The multi-faceted etiology of chronic wounds suggests that exogenous application of a single factor may not have a dramatic comprehensive effect on healing outcomes.

Thus, there is a need for improved compositions and methods for use in wound healing, and, more generally for use in regenerative medicine. There also is a need for compositions and methods for repairing myocardial infarcts.

SUMMARY

A coacervate protein delivery system is used to extend the half-lives of proteins and deliver them to the site of injury. Described herein is the delivery of multiple growth factors and proteins, such as growth factors and proteins obtained in one aspect from a very inexpensive and accessible source, platelet-rich plasma, or other protein-rich solutions, such as solutions obtained from or prepared from products of cells, tissues, organs, organ systems, or organisms, e.g., blood serum. The solution can be from cells, tissues, organs, organ systems, or organisms (natural or genetically altered, e.g. recombinant or transgenic). This advancement allows delivery of a complex cocktail of therapeutic proteins that cannot be made synthetically. Platelet-Rich Plasma is already FDA-approved for clinical use; however, studies show that it is ineffective without a protein delivery system. Therefore this innovation improves upon an approved therapy for wound healing by requiring less doses, reducing cost, and healing wounds more quickly. Other uses include treatment of myocardial infarction, cartilage regeneration, treatment of burns, and treatment of surgical trauma.

The compositions described herein use both synthetic and natural polymers to protect and deliver proteins over several weeks, extending their half-lives from just minutes, and reducing the quantity of protein needed by at least an order of magnitude. This is due to the natural interaction present between an annionic polymer, such as a natural polymer, e.g., heparin or heparan sulfate, and the proteins to be delivered. This forms an affinity-based protein delivery system. In addition, the ability to encapsulate and deliver many proteins simultaneously provides a less-expensive protein source, requiring less processing before implantation. The complex array of proteins this coacervate system is capable of delivering cannot be replicated using recombinant protein sources, and certain described natural protein sources (e.g., platelet-rich plasma, "PRP") are already FDA-approved.

BRIEF DESCRIPTION OF THE DRAWINGS

The drawings provided herein are for illustrative purposes. Certain photomicrographs are color in their original, and are presented herein in grayscale unless otherwise noted. Original colors are indicated in the following descriptions.

(FIG. 2A) PDGF and VEGF exhibit loading efficiencies over 8 times greater than total protein loading due to their affinity to heparin. (FIG. 2B) In vitro release of VEGF and PDGF as representative PRP proteins show a sustained release over 3 weeks. Reported as mean±SD.

(FIG. 5A) Representative wound images show overall wound health at 10 days. All treatment groups other than full PRP coacervate exhibit incomplete filling of the wound bed at this time point. Wounds receiving full PRP coacervate were consistently a healthy pink color (in original) and smaller in area than other treatment groups. Tick marks are mm. (FIG. 5B) full PRP coacervate shows significantly smaller wound size compared to all other treatment 10 days after wounding.

(FIG. 10A) Strain of an infarcted sample was estimated by normalizing the estimated peak radial strain in the infarcted area to that of the average of four non-infarct areas in LV walls during a cardiac cycle. (FIG. 10B) Saline and free proteins groups show decreasing radial strain at eight weeks, which was significantly higher in CR group. Data are presented as means±SD (n=5 per group). *p<0.05 vs saline, ψp<0.05 vs sham.

(FIG. 19A) Representative images of the different groups showing staining of c-Kit$^+$ stem cells (green in original) at eight weeks. (FIG. 19B) Quantitative analysis shows significantly greater number of c-Kit$^+$ stem cells in CR compared to saline and free proteins groups. Data are presented as means±SD (n=5/group at eight wks). *p<0.05 vs saline, ≠p<0.05 vs free proteins, ψp<0.05 vs sham.

DETAILED DESCRIPTION

Figure 1:
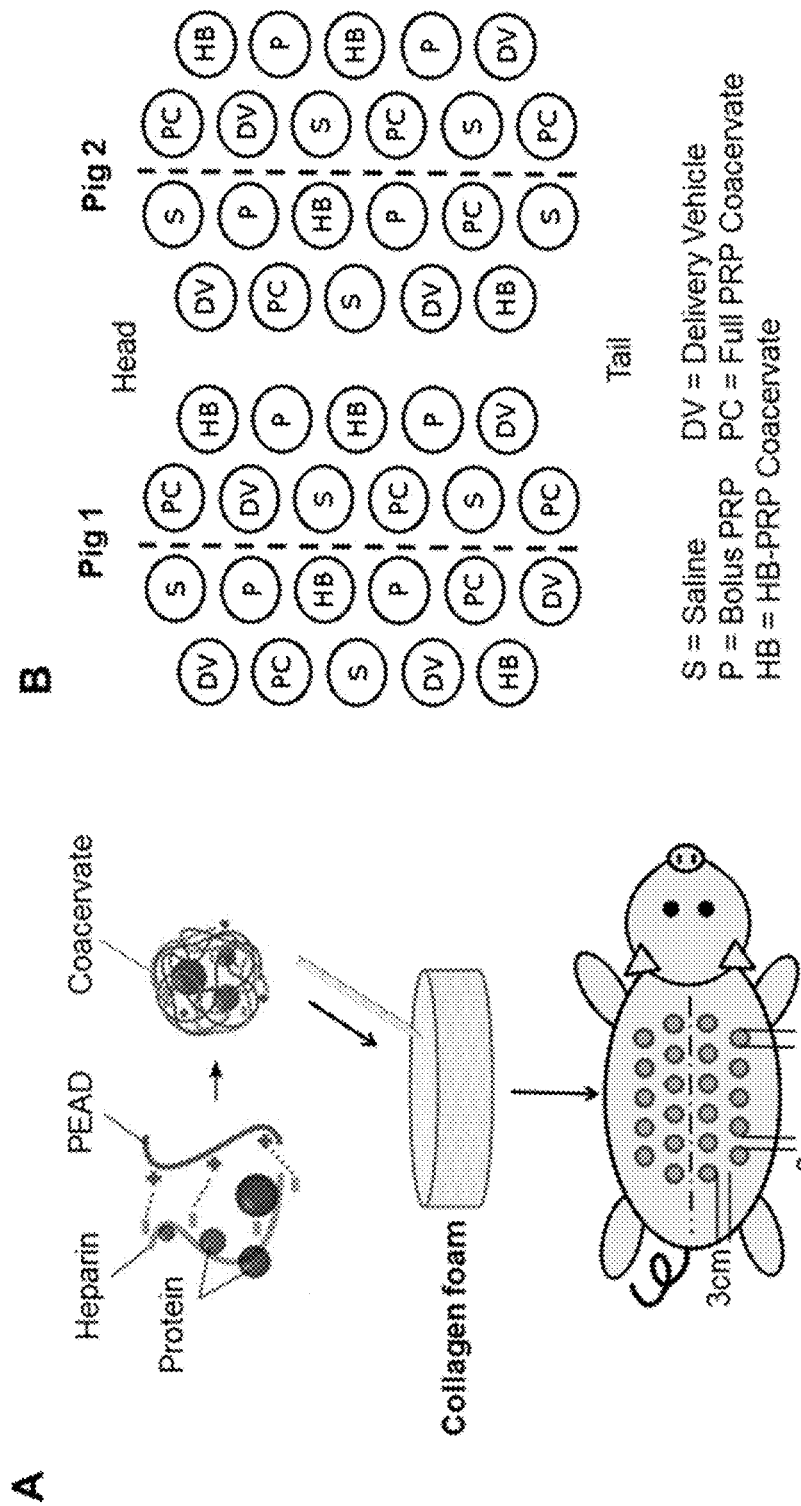
FIG. 1. Outline of the wounding procedure. (A) Combining PEAD with PRP-loaded heparin neutralizes the charged molecules, forming a complex coacervate. Treatments are applied via sterile pipet to a collagen foam before being applied directly to a wound. (B) Forced randomization of treatments accounts for differences in the healing response based on location.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the term "polymer composition" is a composition comprising one or more polymers. As a class, "polymers" includes homopolymers, heteropolymers, co-polymers, block polymers, block co-polymers and can be both natural and synthetic. Homopolymers contain one type of building block, or monomer, whereas co-polymers contain more than one type of monomer.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings.

A "coacervate" refers to herein as a reversible aggregation of compositions in a liquid, for example, as described herein, for example, resulting from the aggregation of oppositely-charged polyionic compositions. Exemplary coacervates are illustrated in the examples below with the aggregation of the polycation, polyanion, and active agent(s), as described herein, for example with the aggregation of PEAD, heparin, and PRP, or a combination of FGF-2 and SDF-1α. A "complex" is a non-covalent aggregation of two or more compositions.

The term "alkyl" refers to both branched and straight-chain saturated aliphatic hydrocarbon groups. These groups can have a stated number of carbon atoms, expressed as $C_{x-y}$, where x and y typically are integers. For example, $C_{5-10}$, includes $C_5$, $C_6$, $C_7$, $C_8$, $C_9$, and $C_{10}$. Alkyl groups include, without limitation: methyl, ethyl, propyl, isopropyl, n-, s- and t-butyl, n- and s-pentyl, hexyl, heptyl, octyl, etc. Alkenes comprise one or more double bonds and alkynes comprise one or more triple bonds. These groups include groups that have two or more points of attachment (e.g., alkylene). Cycloalkyl groups are saturated ring groups, such as cyclopropyl, cyclobutyl, or cyclopentyl. As used herein, "halo" or "halogen" refers to fluoro, chloro, bromo, and iodo.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups or atoms are incorporated into the polymer backbone or are excised. A polymer is said to comprise a specific type of linkage, such as an ester, or urethane linkage, if that linkage is present in the polymer.

According to one aspect of the invention, a composition is provided comprising a complex, e.g. a coacervate of a polyanionic polymer, a polycationic polymer, and platelet-rich plasma or serum, including concentrations thereof, according to any aspect described herein. The platelet-rich plasma or serum, including concentrations thereof, is mixed with the polyanionic polymer composition to form a complex, and the resulting complex is then mixed with a polycationic polymer composition to form a composition, e.g., a coacervate. The charges of the polycation and polyanion are generally approximately equal to form a charge-neutral complex, e.g., coacervate.

Suitable polyanionic polymers include as a class sulfated and/or sulfamated polymer or oligomers, such as sulfated polysaccharides or sulfated glycosoaminoglycans. Sulfated and/or sulfamated polymer or oligomers include sulfated and/or sulfamated polysaccharides. Synthetic and natural sulfated and/or sulfamated polysaccharides or oligosaccharides include, for example and without limitation, sulfated glycosaminoglycans or sulfated galactans, ulvans and fucans (Jiao, G., et al. Chemical Structures and Bioactivities of Sulfated Polysaccharides from Marine Algae (2011) Mar. Drugs 9:196-223). Non-limiting examples of sulfated and/or sulfamated polysaccharides include, pentosan polysulfates, dermatan sulfates, keratan sulfates, chondroitin sulfates, sulfated agarans (e.g., porphyrans), and carageenans. In another aspect, the sulfated and/or sulfamated polymer or oligomer is a sulfated and/or sulfamated synthetic polymer, such as a polyurethane, polyester, polyurea, polyamide-ester, polyether, polycarbonate, polyamide, or polyolefin, or copolymers thereof, as are broadly-known in the polymer arts. By "sulfated", it is meant that the polymer comprises a plurality of pendant sulfate ($-OSO_3$) groups, though many such compositions also are "sulfamated"—comprising a plurality of pendant sulfamate ($-NSO_3$) groups. Examples of suitable polysaccharides include, without limitation: a sulfated polysaccharide, a sulfamated polysaccharides, a sulfated and/or sulfamated polydisaccharide, a sulfated glycosaminoglycan, heparin, and heparan sulfate.

"Platelet-rich plasma" or "PRP" in its broadest sense is blood plasma with an enriched platelet content, where "enriched" is in reference to normal blood of a patient. Typically platelet content is enriched at least two-fold, and often at least five-fold or ten-fold. Platelet-rich plasma is typically prepared by centrifugation of anti-coagulase-treated blood obtained from one or more patients, and can be autologous. Four forms of PRP are commonly-available: Pure Platelet-Rich Plasma (P-PRP) or leucocyte-poor PRP products are preparations without leucocytes and with a low-density fibrin network after activation; Leucocyte-PRP (L-PRP) products are preparations with leucocytes and with a low-density fibrin network after activation. This is the most common commercial PRP product; Pure platelet-rich fibrin (P-PRF) or leucocyte-poor platelet-rich fibrin preparations are without leucocytes and with a high-density fibrin network; and Leucocyte- and platelet-rich fibrin (L-PRF) or second-generation PRP products are preparations with leucocytes and with a high-density fibrin network (Dhurat et al. Principles and Methods of Preparation of Platelet-Rich Plasma: A Review and Author's Perspective. *Journal of Cutaneous and Aesthetic Surgery.* 2014; 7(4):189-197).

A number of methods are broadly-known for preparation of PRP. In one instance, blood is collected in tubes containing anticoagulants. A platelet layer, a buffy coat layer, and a red blood cell (RBC) layer are produced. For production of P-PRP, the platelet layer ad only the superficial buffy coat layer are transferred to a clean tube. For preparation of L-PRP, the platelet layer and buffy coat layer are transferred to a clean tube. The second tube is spun in a centrifuge resulting in a soft platelet pellet at the bottom of the tube. A portion, e.g. ⅔, of the platelet-poor top volume is removed, and the platelet pellet is then dispersed, e.g. homogenized, in the remaining plasma. An alternative method is known as the "buffy coat" method in which whole blood is centrifuged at a high speed to form a tighter buffy coat as compared to the PRP method above. PRP, and in general platelets, can be activated by addition of calcium and thrombin as is broadly-known, or by any other useful means.

"Serum" is blood that is allowed to coagulate, and the clot and cellular constituents are then removed. Fractions of serum or platelet-rich plasma may be employed. By "fractions", it is meant a portion of the serum or platelet-rich plasma prepared by any suitable method, including by precipitation, solvent extraction, filtration, centrifugation, or any other suitable method—so long as the fractionated product is not reduced to a single purified compound, such as a single protein, glycoprotein, polysaccharide, or other composition found in the platelet-rich plasma or serum. Concentrates are solutions in which a portion of the solvent, e.g. water in the case of a blood product, is removed thereby increasing the concentration of compounds present in the solution, such as proteins, glycoproteins, polysaccharides, or other desirable compositions found in the platelet-rich plasma or serum.

FGF-2 is Fibroblast growth factor 2 (HGNC: 3676, Entrez Gene: 2247, Ensembl: ENSG00000138685, OMIM: 134920, UniProtKB: P09038), having the sequence, for example:

```
                                              (SEQ ID NO: 1)
MVGVGGGDVEDVTPRPGGCQISGRGARGCNGIPGAAAWEAALPRRRPRR

HPSVNPRSRAAGSPRTRGRRTEERPSGSRLGDRGRGRALPGGRLGGRGR

GRAPERVGGRGRGRGTAAPRAAPAARGSRPGPAGTMAAGSITTLPALPE

DGGSGAFPPGHFKDPKRLYCKNGGFFLRIHPDGRVDGVREKSDPHIKLQ

LQAEERGVVSIKGVCANRYLAMKEDGRLLASKCVTDECFFFERLESNNY

NTYRSRKYTSWYVALKRTGQYKLGSKTGPGQKAILFLPMSAKS
```

SDF-1α, Stromal Cell-Derived Factor 1, is the geane product of CXCL12 gene in humans (HGNC: 10672, Entrez Gene: 6387, Ensembl: ENSG00000107562, OMIM: 600835, UniProtKB: P48061), and having an exemplary sequence:

```
                                              (SEQ ID NO: 2)
    MNAKVVVVLV LVLTALCLSD GKPVSLSYRC PCRFFESHVA

RANVKHLKIL NTPNCALQIV ARLKNNNRQV CIDPKLKWIQ

EYLEKALNKR FKM.
```

TIMP-3 is TIMP is Tissue Inhibitor of Metalloproteinase 3 (HGNC: 10672, Entrez Gene: 6387, Ensembl: ENSG00000107562, OMIM: 600835, UniProtKB: P48061), having an exemplary amino acid sequence:

```
                                              (SEQ ID NO: 3)
MTPWLGLIVLLGSWSLGDWGAEACTCSPSHPQDAFCNSDIVIRAKVVGKK

LVKEGPFGTLVYTIKQMKMYRGFTKMPHVQYIHTEASESLCGLKLEVNKY

QYLLTGRVYDGKMYTGLCNFVERWDQLTLSQRKGLNYRYHLGCNCKIKSC

YYLPCFVTSKNECLWTDMLSNFGYPGYQSKHYACIRQKGGYCSWYRGWAP

PDKSIINATDP.
```

Certain polymers described herein, such as heparin and PEAD, are said to be bioerodible or biodegradable. By that, it is meant that the polymer, once implanted and placed in contact with bodily fluids and tissues, or subjected to other environmental conditions, such as composting, will degrade either partially or completely through chemical reactions, typically and often preferably over a time period of hours, days, weeks or months. Non-limiting examples of such chemical reactions include acid/base reactions, hydrolysis reactions, and enzyme catalyzed bond scission. Certain polymers described herein contain labile ester linkages. The polymer or polymers may be selected so that it degrades over a time period. Non-limiting examples of useful in situ degradation rates include between 12 hours and 5 years, and increments of hours, days, weeks, months or years therebetween.

A drug delivery composition is provided, comprising, a coacervate of a polycationic polymer, a polyanionic polymer, and an active agent. In certain aspects, the polycationic polymer described herein comprises the structure (that is, comprises the moiety: [—OC(O)-B'—CH(OR1)-B-]$_n$ or —[OC(O)—B—C(O)O—CH$_2$—CH(O—R1)-CH$_2$—B'-CH$_2$—CH(O—R2)-CH$_2$-]$_n$, in which B and B' are the same or different and are organic groups, or B' is not present, including, but not limited to: alkyl, ether, tertiary amine, ester, amide, or alcohol, and can be linear, branched or cyclic, saturated or unsaturated, aliphatic or aromatic, and optionally comprise one or more protected active groups, such as, without limitation, protected amines and acids, and R1 and R2 are the same or different and are hydrogen or a functional group (e.g., as described herein). As seen below, the composition exhibits low polydispersity, with a polydispersity index of less than 3.0, and in many cases less than 2.0. These compositions are described in U.S. Pat. No. 9,023,972, which is incorporated by reference in its entirety.

In one aspect, the polycationic polymer is a polymer composition comprising at least one moiety selected from the following in which B and B' are residues of aspartic acid or glutamic acid, which are optionally further derivatized with an amine-containing group, for example, the amines of the aspartic acid or glutamic acid are further derivatized with lysine or arginine:

(a) [—OC(O)—CH(NHY)—CH$_2$—C(O)O—CH$_2$—CH(O—R1)-CH$_2$—O—CH$_2$—CH$_2$—O—CH$_2$—CH(O—R2)-CH$_2$-]$_n$, (b) [—OC(O)—CH$_2$—CH(NHY)-C(O)O—CH$_2$—CH(O—R1)-CH$_2$—O—CH$_2$—CH$_2$—O—CH$_2$—CH(O—R2)-CH$_2$-]$_n$, (c) [—OC(O)—CH(NHY)—CH$_2$—CH$_2$—C(O)O—CH2-CH(O—R1)-CH$_2$—O—CH$_2$—CH$_2$—O—CH$_2$—CH(O—R2)-CH$_2$-]$_n$, and/or (d) [—OC(O)—CH$_2$—CH$_2$—CH(NHY)-C(O)O—CH2-CH(O—R1)-CH$_2$—O—CH$_2$—CH$_2$—O—CH$_2$—CH(O—R2)-CH$_2$-]$_n$, wherein Y is —C(O)—CH(NH$_3^+$)—(CH$_2$)$_3$—NH—C(NH$_2$)$_2^+$ or —C(O)—CH(NH$_3^+$)-(CH$_2$)$_4$-(NH$_3$)$^+$, and R1 and R2 are the same or different and are independently selected from the group consisting of hydrogen, a carboxy-containing group, a C$_{1-6}$ alkyl group, an amine-containing group, a quaternary ammonium containing group, and a peptide.

The polymers described herein can be functionalized, e.g., at B, B', R1 and R2, meaning they comprise one or more groups with an activity, such as a biological activity. For example and without limitation, as shown herein, the polymer may be functionalized with an acetylcholine-like group or moiety, a cross-linking agent (cross-linking agents contain at least two reactive groups that are reactive towards numerous groups, including sulfhydryls and amines, and create chemical covalent bonds between two or more molecules, functional groups that can be targeted with cross-linking agents include primary amines, carboxyls, sulfhydryls, carbohydrates and carboxylic acids. A large number of such agents are available commercially from, e.g., Thermo fisher Scientific (Pierce) and Sigma).

Other functions that can be provided by or enhanced by addition of functional groups include: increased hydrophobicity, for instance by functionalizing with a superhydrophobic moiety, such as a perfluoroalkane, a perfluoro(alkylsilane), and/or a siloxane; increased hydrophilicity, for instance by functionalizing with polyethylene glycol (PEG);

or antimicrobial, for instance, by functionalizing with a quaternary amine. The polymer can be functionalized with a tag, such as a fluorescent tag (e.g., FITC, a cyanine dye, etc.). The polymer can be functionalized by linking to additional synthetic or natural polymers, including, without limitation: synthetic polymers, such as a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, a polymer comprising carbonate linkages, a polycarbonate, a polyglyconate, a poly(glycolide-co-trimethylene carbonate), a poly(glycolide-co-trimethylene carbonate-co-dioxanone), a polymer comprising urethane linkages, a polyurethane, a poly(ester urethane) urea, a poly (ester urethane) urea elastomer, a polymer comprising ester linkages, a polyalkanoate, a polyhydroxybutyrate, a polyhydroxyvalerate, a polydioxanone, a polygalactin, or natural polymers, such as chitosan, collagen, gelatin, elastin, alginate, cellulose, hyaluronic acid and other glycosaminoglycans.

The compositions may be functionalized with organic or inorganic moieties to achieve desired physical attributes (e.g., hardness, elasticity, color, additional chemical reactivity, etc.), or desired functionality. For example, the polymer composition may be derivatized with maleic acid or phosphate.

Further to the above, functional groups may vary as indicated above. For example, in certain aspects, R1 and R2 are the same or different and are independently selected from the group consisting of hydrogen, a carboxy-containing group, a $C_{1-6}$ alkyl group, an amine-containing group, a quaternary ammonium containing group, and a peptide. In one aspect, one or more of B, B', R1 and R2 are charged such that it is possible to bind various water insoluble organic or inorganic compounds to the polymer, such as magnetic inorganic compounds. As above, in one aspect, one or more of B, B', R1 and R2 are positively charged. In one aspect, one or both of R1 and R2 are functionalized with a phosphate group. In another aspect, the composition is attached non-covalently to a calcium phosphate (including as a group, for example and without limitation: hydroxyapatite, apatite, tricalcium phosphate, octacalcium phosphate, calcium hydrogen phosphate, and calcium dihydrogen phosphate). In yet another embodiment, R1 and R2 are independently one of Ile-Lys-Val-Ala-Val (IKVAV) (SEQ ID NO: 4), Arg-Gly-Asp (RGD), Arg-Gly-Asp-Ser (RGDS) (SEQ ID NO: 5), Ala-Gly-Asp (AGD), Lys-Gln-Ala-Gly-Asp-Val (KQAGDV) (SEQ ID NO: 6), Val-Ala-Pro-Gly-Val-Gly (VAPGVG) (SEQ ID NO: 7), APGVGV (SEQ ID NO: 8), PGVGVA (SEQ ID NO: 9), VAP, GVGVA (SEQ ID NO: 10), VAPG (SEQ ID NO: 11), VGVAPG (SEQ ID NO: 12), VGVA (SEQ ID NO: 13), VAPGV (SEQ ID NO: 14) and GVAPGV (SEQ ID NO: 15).

The composition is formed into a coacervate with active agents or polyanionic or polycationic groups for sequestering active agents for controlled delivery in vivo. Drug products comprising the coacervate described herein may be delivered to a patient by any suitable route of delivery (e.g. oral or parenteral), or as an implantable device for slow release of the active agent.

In forming the composition (e.g., coacervate), the cationic polycationic polymer is complexed with a polyanionic polymer, such as heparin or heparan sulfate, which is complexed with an active agent, such as a growth factor, small molecule, cytokine, drug, a biologic, a protein or polypeptide, a chemoattractant, a binding reagent, an antibody or antibody fragment, a receptor or a receptor fragment, a ligand, an antigen and/or an epitope, PRP, or a composition obtained from an organism or cultured cells, tissues or organs and containing a native, complex mixture of proteins and/or growth factors. Specific examples of active agents include interleukins (IL), such as IL-2 and IL-12 (e.g., IL-12 p70), and interferons (IFN), such as IFN-γ. In one aspect, the composition comprises a coacervate of a polycationic polymer comprising one or more of moieties (a), (b), (c), and/or (d), as described above, and further comprising heparin or heparin sulfate complexed (that is non-covalently bound) with FGF-2 and SDF-1α. The composition is formed, for example, by mixing in a suitable solvent, such as an aqueous solution, such as water, saline (e.g. normal saline), or PBS, the polyanionic, polycationic, and active agent constituents of the composition.

Additional active agents that may be incorporated into the coacervate include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, anti-inflammatory cytokines, and anti-inflammatory proteins or steroidal anti-inflammatory agents); antibiotics; anticlotting factors such as heparin, Pebac, enoxaparin, aspirin, hirudin, plavix, bivalirudin, prasugrel, idraparinux, warfarin, coumadin, clopidogrel, PPACK, GGACK, tissue plasminogen activator, urokinase, and streptokinase; growth factors. Other active agents include, without limitation: (1) immunosuppressants; glucocorticoids such as hydrocortisone, betamethasone, dexamethasone, flumethasone, isoflupredone, methylprednisolone, prednisone, prednisolone, and triamcinolone acetonide; (2) antiangiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, bevacizumab, neovastat; (3) antiproliferatives such as sirolimus, paclitaxel, perillyl alcohol, farnesyl transferase inhibitors, FPTIII, L744, anti-proliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; (4) antibodies; drugs acting on immunophilins, such as cyclosporine, zotarolimus, everolimus, tacrolimus and sirolimus (rapamycin), interferons, TNF binding proteins; (5) taxanes, such as paclitaxel and docetaxel; statins, such as atorvastatin, lovastatin, simvastatin, pravastatin, fluvastatin and rosuvastatin; (6) nitric oxide donors or precursors, such as, without limitation, Angeli's Salt, L-Arginine, Free Base, nitrates, nitrites, Diethylamine NONOate, Diethylamine NONOate/AM, Glyco-SNAP-1, Glyco-SNAP-2, (.+−.)-S-Nitroso-N-acetyl-penicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin; and (7) antibiotics, such as, without limitation: acyclovir, ofloxacin, ampicillin, amphotericin B, atovaquone, azithromycin, ciprofloxacin, clarithromycin, clindamycin, clofazimine, dapsone, diclazuril, doxycycline, erythromycin, ethambutol, fluconazole, fluoroquinolones, foscarnet, ganciclovir, gentamicin, itraconazole, isoniazid, ketoconazole, levofloxacin, lincomycin, miconazole, neomycin, norfloxacin, ofloxacin, paromomycin, penicillin, pentamidine, polymyxin B, pyrazinamide, pyrimethamine, rifabutin, rifampin, sparfloxacin, streptomycin, sulfadiazine, tetracycline, tobramycin, trifluorouridine, trimethoprim sulfate, Zn-pyrithione, and silver salts such as chloride, bromide, iodide and periodate.

Further examples of additional active agents include: basic fibroblast growth factor (bFGF or FGF-2), acidic fibroblast growth factor (aFGF), nerve growth factor (NGF), vascular endothelial growth factor (VEGF), hepatocyte growth factor (HGF), transforming growth factor-beta pleiotrophin protein, midkine protein, platelet-derived growth factor (PDGF) and angiopoietin-1 (Ang-1). Active agents are included in the delivery system described herein, and are administered in amounts effective to achieve a desired end-point, such as angiogenesis, tissue growth, inhibition of tissue growth, repair of tissue (e.g. an infarct) or any other desirable end-point.

According to one aspect, complex structures are provided that comprise the coacervate described herein mixed with, distributed within, or otherwise combined with another composition, such as a hydrogel, a polymer, and/or an inorganic substrate, and can be combined with a medical implant or device such as a prosthetic, a dosage form, a woven or non-woven mesh, etc. According to one aspect, the coacervate is combined with a hydrogel, for example by embedding the coacervate in a hydrogel, such as fibrin. Such a structure is useful for providing complex release profiles for active agents, for instance for promoting specific tissue growth or as a timed-release dosage form. In such an aspect, one or more active agents are distributed by any method in the coacervate and in the hydrogel so as to cause a defined degradation and release pattern. One useful aspect would be to embed the coacervate having a first active agent into a hydrogel, having a second active agent, to provide a complex release profile. In any aspect, the active agent(s) can be any effective active agent(s), for example as described above. As an example, factor A is embedded into a hydrogel, e.g. a fibrin gel, for early release and factor B is contained within the coacervate, for delayed release. For each indicated purpose it is noted that appropriate relative amounts of the coacervate and hydrogel may be used, as well as including effective amounts of the active agents for the intended purpose, respectively in the coacervate and hydrogel. Appropriate and effective amounts of each component can be determined in the ordinary course by a person of skill in the art.

Therefore, according to one aspect of the invention, a composition is provided comprising a complex, e.g. a coacervate of a polyanionic polymer, a polycationic polymer, and one or more active agents, that is embedded in a hydrogel, such as a fibrin hydrogel, which contains an active agent for faster release than active agent(s) complexed in the coacervate. In one aspect, the active agent is PRP, serum, or a complex mixture of proteins and/or growth factors produced by cells, tissue, or an organism. In one aspect, the active agents complexed in the coacervate are FGF-2 and SDF-1α by first mixing with the polyanionic polymer, followed by mixing with the polycationic polymer to form the coacervate. The charges of the polycation and polyanion are generally approximately equal to form a charge-neutral complex, e.g., coacervate. TIMP-3 and the coacervate are then mixed into a hydrogel composition, e.g. prior to or during formation of the hydrogel. In one aspect, each active agent is present in amounts effective to treat a myocardial infarct, by application of the composition at or near a myocardial infarct, e.g., by injection.

Examples of useful active agents and combinations of agents for incorporation into the described coacervate for treatment of a myocardial infarct include: TIMP-3, FGF-2, and SDF-1α. Also described herein is a method of treatment of myocardial infarction, using the combination of TIMP-3 in a hydrogel, and a coacervate as described comprising FGF-2 and SDF-1α.

The coacervate composition according to any aspect described herein is delivered in any manner useful and appropriate for treatment of a condition in a patient, such as for treatment of a wound, cardiovascular disease, or an infarct, such as by enteral, parenteral, or topical routes, for example and without limitation by: intravenous (IV), local injection, intramuscular, intracerebral, subcutaneous, oral, inhalation, topical, enema, intravaginal, intrauterine, ocular, or otic routes. Typically, due to the nature of wounds and myocardial infarcts, the composition is typically applied either topically or by injection at or near the site of the wound or infarct, as opposed to systemically.

Suitable excipients or carriers are employed for delivery of the coacervate composition, though the excipients are consistent with maintenance of the coacervate complex. Suitable excipients are broadly-known in the pharmaceutical arts, and include: solvents, such as water, phosphate-buffered saline (PBS), saline; buffers; salts; acids; bases; rheology modifiers; chelating agents; colorants; flavorings; penetration enhancers; and preservatives. The coacervate composition is provided in a suitable vessel for storage, distribution and/or use of the composition. In one aspect, the coacervate composition is provided in a tube, a medical syringe, an IV bag. In another aspect, the coacervate composition is delivered to a patient in an amount effective to treat a myocardial infarction, for example by direct injection of the coacervate composition comprising TIMP-3, FGF-2, and SDF-1α into the heart, e.g., the myocardium at or adjacent to an infarct.

An "amount effective" for treatment of a condition is an amount of an active agent or dosage form, such as the coacervate composition described herein, effective to achieve a determinable end-point. The "amount effective" is preferably safe—at least to the extent the benefits of treatment outweighs the detriments and/or the detriments are acceptable to one of ordinary skill and/or to an appropriate regulatory agency, such as the U.S. Food and Drug Administration. In the context of wound healing, the end point may be decreased wound size, in a myocardial infarction, the end point may be improved cardiac output or improvement in the infarcted tissue, or in both instances any other objectively-determinable indicator of improvement in a patient's condition or symptoms. Using the teachings of the present disclosure, a person of ordinary skill in the arts can prepare the coacervate composition described herein, and titrate the effect on any objectively-determinable end-point, for instance first in an animal model and later in humans. As shown in the Examples below, an example of an "amount effective" is indicated.

The coacervate composition may be administered continually for a period of time, or at intervals, ranging from hourly, weekly, monthly, or yearly, including increments therebetween, such as from one to six times per day, daily, every other day, weekly, bi-weekly, monthly, bi-monthly, quarterly, etc. An appropriate dosing schedule can be determined by a person of ordinary skill, such as a physician, and can also be tailored to wound or infarct severity in a patient, or improvement in wound healing, cardiac output or infarct repair.

In use, according to one aspect, the coacervate composition is delivered to a patient in an amount effective to treat a wound in a patient. For treating a wound, the coacervate is formed in the presence of platelet-rich plasma or serum according to any aspect described herein. The composition is delivered, for example by injection, at or adjacent to a wound, or application as a solution, gel, or as applied to any medical device or wound dressing. In one aspect, the composition is delivered to a patient at or adjacent to a wound by injection, topical application, spraying (spay or aerosol), swabbing, or any effective means of transferring the composition to the wound location. In another aspect, the composition is applied to a wound dressing, such as a bandage, a suture, a surgical mesh, or a non-woven material as are broadly-known in the medical arts. In yet another aspect, the composition is applied to an implanted medical device, such as a prostheses, so that the composition facilitates integration of the device into the local tissue and/or healing of wound surrounding the device as a result of trauma, disease, or the process of inserting the device, such as a heart valve.

In another aspect, the coacervate composition is delivered to a patient in an amount effective to treat a cardiovascular disease, such as coronary heart disease, including treatment of ischemic conditions, such as myocardial infarction. In one aspect, the composition is delivered to a patient's myocardium at or adjacent to an infarct, the composition comprising a hydrogel, such as a fibrin hydrogel, comprising TIMP-3, and a complex or coacervate of a polycationic polymer, a polyanionic polymer, FGF-2 and SDF-1α embedded in the hydrogel. The composition and respective amounts of TIMP-3, FGF-2, and SDF-1α are administered in amounts effective to treat the infarct, that is to improve one or more clinically-relevant markers, such as to improve cardiac function parameters such as myocardial elasticity, to reduce infarct size, to increase revascularization of the infarct, to reduce scarring of the myocardium, and/or stimulate repair of the myocardium. Other conditions, such as myocardial reperfusion injury and peripheral artery disease may be treated in the same manner.

In another aspect, a composition is provided comprising a coacervate of a polycationic polymer, a polyanionic polymer, and a composition obtained from an organism or cultured cells, tissues or organs and containing a native, complex mixture of proteins and/or growth factors. A "native, complex mixture of proteins and/or growth factors" refers to a composition produced by a living source, and though it may proceed through one or more purification steps, as in the case of PRP as described herein to remove blood cells, activate platelets, and optionally to remove fibrin and to concentrate the proteins, it is not an isolated or purified single constituent, but includes a plurality of compounds and proteins, such as growth factors, essentially in amounts and proportions found in, or produced by the cells or organism. Examples of suitable sources of the native, complex mixture of proteins and/or growth factors include: a bodily fluid such as blood—including plasma or serum, or processed plasma or serum, conditioned medium from a cell, tissue or organ culture, or a cell or tissue lysate or homogenate.

As used herein "conditioned media" is media prepared by the culture of cells or other living tissue therein, wherein the cells or living tissue are natural or genetically-modified. The conditioned media includes proteins and other compositions representative of the secretome of the living material grown therein. The cell secretome refers not only to the collection of proteins that contain a signal peptide and are processed via the endoplasmic reticulum and Golgi apparatus through the classical secretion pathway, but encompasses proteins shed from the cell surface and intracellular proteins released through non-classical secretion pathway or exosomes. These secreted proteins may be enzymes, growth factors, cytokines, hormones, and/or other soluble mediators. The medium used to produce the conditioned media by growth of living cells or tissue therein may be any medium suitable for growth of the living cells or tissue. A large variety of media is available commercially, and one of ordinary skill in the art could determine a useful or optimal medium for use in this context. In one aspect, the media is serum-free. Various other fractionation processes, such as precipitation, centrifugation, affinity separation, or filtration may be applied to clean up, to remove harmful compounds, or to otherwise fractionate the conditioned media.

The coacervate compositions according to any aspect described herein are formulated into medically- and pharmaceutically-acceptable dosage forms or devices, such as a liquid, a gel, a spray, an aerosol, or a wound dressing or medical device, such as a non-woven, a bandage, a suture, a mesh, a prosthetic, or an implantable/implanted medical device. The composition may comprise any useful excipient, or inactive ingredient, such as water, saline, phosphate-buffered saline, and effective amounts of any non-interfering active agent, such as, without limitation: an antibiotic, an anti-inflammatory, or an analgesic, or any other useful active agent, as are broadly-known in the pharmaceutical arts. A person of ordinary skill in the medical and pharmaceutical arts can readily fashion any of these products.

Example 1—Synthesis and Testing of PEAD

Synthesis and testing of PEAD, PEAD-heparin, and PEAD FGF2 are described in U.S. Pat. No. 9,023,972, which is incorporated by reference in its entirety. Briefly, for synthesis of PEAD—t-BOC protected aspartic acid (t-BOC Asp), t-BOC protected arginine (t-BOC-Arg) (EMD Chemicals, NJ), ethylene glycol diglycidyl ether (EGDE), trifluoroacetic acid (TFA) (TCI America, OR), anhydrous 1,4-dioxane and tetra-n-butylammonium bromide (TBAB) (Acros organics, Geel, Belgium), dicyclohexylcarbodiimide (DCC), N-hydroxysuccinimide (NHS) (Alfa Aesar, MA) and 4-dimethylaminopyridine (DMAP) (Avocado Research Chemicals Ltd, Lancaster, UK) were used for PEAD synthesis without purification. The synthesis of PEAD is performed as follows. EGDE and t-BOC Asp were polymerized in 1,4-dioxane under the catalysis of TBAB. t-BOC protection was later removed by TFA to generate primary amine. t-BOC-Arg was conjugated by DCC/NHS/DMAP coupling followed by the second de-protection to yield PEAD. The chemical structure was confirmed using NMR and FT-IR. The molecular weight of PEAD was measured by PL-GPC 50 Plus-RI equipped with a PD 2020 light scattering detector (Varian, MA). Two MesoPore 300×7.5 mm columns and 0.1% of LiBr in DMF were used as solid phase and mobile phase, respectively. In one example, the weight-average molecular weight (Mw) is 30,337 Da with polydispersity index (PDI) 2.28.

Since PEAD is a positively-charged molecule, addition of PEAD into heparin solution should neutralize the negative charge of heparin and forms PEAD/heparin complex. To test the binding ability of PEAD to heparin, zeta potential measurement was performed and the zeta potential of the complex shifted from negatively-charged (−45 mV) at ratio 1 to positively-charged (+23.2 mV) at ratio 10. Continuing adding more PEAD did not change the zeta potential and +23.2 mV is close to the zeta potential of PEAD itself. Data suggested that for the described PEAD preparation after ratio 10 the complex was all covered by PEAD. Besides it also shows at ratio 5 PEAD almost neutralized all negative charges of heparin. From the macroscopic observation, below ratio 5 the addition of PEAD let the heparin solution became more turbid and precipitate was seen after a few minutes. Whereas the ratio was over 5, the addition of PEAD would let the solution become clear again.

Further confirming the binding ability, different amounts of PEAD to heparin solutions were mixed and then precipitated by centrifugation. Because the neutralization of the negative-charged heparin favors the formation of precipitate, we measured the amount of heparin left in the supernatant was measured to determine the binding affinity between PEAD and heparin. For this assay, a heparin binding dye, dimethylmethylene blue (DMB) was applied to detect free heparin by measuring the absorption of DMB at 520 nm. The result shows the amount of heparin in the supernatant was gradually lowered with the addition of PEAD. When the ratio of PEAD to heparin is over 3, >90% of heparin was precipitated through centrifugation. At the ratio 5, that would be >99% of heparin. This result has a good correlation with that of zeta potential measurement because both experiments suggest at ratio 5 PEAD and heparin has the maximum interaction.

It is understood that a variety of growth factors can bind to heparin with the dissociation constant (Kd) from μM to nM. The loading efficiency of growth factors to PEAD/heparin complex was studied. 100 ng or 500 ng of fibroblast growth factor-2 (FGF-2) plus $^{125}$I-labeled FGF-2 used as a tracer were mixed with heparin then added into PEAD solution. After staying at room temperature for 2 hr, centrifugation was used to precipitate PEAD/heparin/FGF-2. The amount of unloaded FGF-2 remaining in the supernatant can be determined by a gamma counter. The result showed PEAD/heparin loaded ~68% of FGF-2 for both high and low amounts of FGF-2. The other growth factor, NGF, the release is faster. The initial burst reached almost 20%. The release sustained till day 20 and reached a plateau corresponding to ~30% of the loaded NGF.

PRP is a blood product containing many therapeutic growth factors. It is used clinically although its true efficacy for wound healing is debated throughout the field due to a lack of systematic studies concerning its use. PRP is theoretically advantageous due to the complex mixture of therapeutic proteins present, but the short half-life of these proteins could render them useless within minutes.

Example 2—Full-Thickness Excisional Wound Pig Model

Platelet-rich plasma (PRP) is widely used for many clinical indications including wound healing due to the high concentrations of growth factors. However, the short half-life of these therapeutic proteins requires multiple large doses, and their efficacy is highly debated among clinicians. Here we report a method of protecting these proteins and releasing them in a controlled manner via a heparin-based coacervate delivery vehicle to improve wound healing in a porcine model. Platelet-derived proteins incorporated into the coacervate were protected and slowly released over 3 weeks in vitro. In a porcine model, PRP coacervate significantly accelerated the healing response over 10 days, in part by increasing the rate of wound reepithelialization by 35% compared to control. Additionally, PRP coacervate doubled the rate of wound contraction compared to all other treatments, including that of naked PRP proteins. Wounds treated with PRP coacervate exhibited increased collagen alignment and an advanced state of vascularity compared to control treatments. These results suggest that this preparation of PRP accelerates healing of cutaneous wounds only as a controlled release formulation. The coacervate delivery vehicle is a simple and effective tool to improve the therapeutic efficacy of platelet-derived proteins for wound healing.

One alternative to mono-therapy is to harness the mixture of growth factors produced by the patient themself (autologous) or from a healthy allogenic donor in the form of platelet-rich plasma (PRP). PRP is a fraction of blood plasma containing many therapeutic growth factors released from alpha-granules upon platelet activation (F. Mussano, et al., Cytokine, chemokine, and growth factor profile of platelet-rich plasma, Platelets, (2016) 1-5). This protein cocktail has high potential to stimulate an accelerated healing response since it contains numerous factors known to play different vital roles in the natural healing progression. Autologous PRP avoids the risk of an immune response during treatment, although allogenic PRP has also been used safely in a clinical setting without serious adverse effects as long as the platelets were removed (Z. Y. Zhang, et al., The potential use of allogeneic platelet-rich plasma for large bone defect treatment: immunogenicity and defect healing efficacy, *Cell Transplant,* 22 (2013) 175-187). PRP is currently approved for use in orthopedic applications and is under investigation for several others including wound healing (Z. Y. Zhang, et al., The potential use of allogeneic platelet-rich plasma for large bone defect treatment: immunogenicity and defect healing efficacy, *Cell Transplant,* 22 (2013) 175-187; V. R. Driver, et al., G. Autologel Diabetic Foot Ulcer Study, A prospective, randomized, controlled trial of autologous platelet-rich plasma gel for the treatment of diabetic foot ulcers, *Ostomy/wound management,* 52 (2006) 68-70, 72, 74 passim; K. K. Middleton, et al., Evaluation of the effects of platelet-rich plasma (PRP) therapy involved in the healing of sports-related soft tissue injuries, *Iowa Orthop J,* 32 (2012); T. D. Vu, et al., An autologous platelet-rich plasma hydrogel compound restores left ventricular structure, function and ameliorates adverse remodeling in a minimally invasive large animal myocardial restoration model: a translational approach: Vu and Pal "Myocardial Repair: PRP, Hydrogel and Supplements", *Biomaterials,* 45 (2015) 27-35 150-163; and H. S. Yang, et al., Enhanced skin wound healing by a sustained release of growth factors contained in platelet-rich plasma, *Exp Mol Med,* 43 (2011) 622-629). There are many ways to prepare PRP though very few studies have utilized consistent methodology, wound types, or patient demographics, which has led to conflicting data regarding its efficacy. Numerous studies report that PRP improves the wound healing response (V. R. Driver, et al., *Ostomy/wound management,* 52 (2006) 68-70, 72, 74 passim; H. S. Yang, et al., *Exp Mol Med,* 43 (2011) 622-629; and M. J. Martinez-Zapata, et al., Autologous platelet-rich plasma for treating chronic wounds, *The Cochrane database of systematic reviews,* 10 (2012) Cd006899), while numerous others found it to have no significant effect on healing outcomes (M. J. Martinez-Zapata, et al., *The Cochrane database of systematic reviews,* 10 (2012) Cd006899). Since each study involves a different formulation, it is difficult to determine the true potential of PRP as a wound healing therapy. As with individual growth factor therapies, the proteins found in PRP also have short half-lives, limiting their efficacy without repeated administrations (K. Lee, et al., Growth factor delivery-based tissue engineering: general approaches and a review of recent developments, *Journal of the Royal Society, Interface/the Royal Society,* 8 (2011) 153-170 and H. S. Yang, et al., *Exp Mol Med,* 43 (2011) 622-629).

Complex coacervates form when a cationic polymer solution is mixed with an anionic polymer solution that leads to charge neutralization and phase separation of a polymer-rich phase from the bulk water. Here, we use heparin as the anionic polymer. Many therapeutic growth factors such as VEGF, heparin-binding EGF-like growth factor (HB-EGF), and hepatocyte growth factor (HGF) have a natural affinity for heparan sulfate, a glycosaminoglycan (GAG) found in the ECM. Heparin has similar structure and functionality as heparan sulfate, with the ability to protect growth factors from proteolytic degradation and present them to cell receptors in biomimetic fashion. A synthetic polycation, poly (ethylene argininylaspartate diglyceride) (PEAD), interacts with the anionic heparin via polyvalent charge attraction, forming a complex coacervate containing high concentrations of the polymers while the bulk water phase has little polymer left. Thus this system loads heparin-binding growth factors with high efficiency. The final delivery system consists coacervate droplets suspended within the aqueous phase. The droplets range from 10 to 500 nm in diameter and remain stable for at least one month in vivo. Previous studies have shown that this system delivers growth factors for weeks and significantly extends their half-lives. Coacervate delivery of growth factors can improve cardiac function after myocardial infarction and accelerate wound healing, see Example 3. Here we utilize our coacervate system with PRP in a pig model of wound healing. Pig skin is very similar to human skin and thus provides an appropriate pre-clinical indication for potential success in human patients. Since PRP is widely available and inexpensive, its validation as a growth factor source for therapeutic application in a large animal model takes this technology one step closer to clinical translation.

Materials and Methods

PRP Preparation and Protein Quantification: Patient samples were obtained from the Central Blood Bank of Pittsburgh. Fresh plasma was obtained within four hours of collection from the patient to maintain high bioactivity of growth factors and cytokines. To isolate PRP, the plasma was then centrifuged at 2,000×g for 15 minutes, and the bottom half of the solution was taken as PRP. Thrombin (Sigma-Aldrich, St. Louis, MO) was added at 1,000 U/mL and $CaCl_2$ added at 10% (w/v) with gentle agitation to activate the platelets for one hour. Platelets released their therapeutic proteins into the surrounding plasma upon activation, and the fibrin clot was removed by centrifugation. A 3 kDa MWCO centrifugal filter unit (EMD Millipore, Billerica, MA) was used to further concentrate the proteins in solution. Total protein content was measured by Pierce 660 nm protein assay (Thermo Fisher Scientific, Waltham, MA), and individual growth factor concentrations were quantified using sandwich ELISA kits per manufacturer instructions (PeproTech, Rocky Hill, NJ). Concentrated PRP was stored at −80° C. until later use.

Platelet-Derived Protein Loading and Release: The loading and release of platelet-derived proteins from the coacervate delivery system over 4 weeks in vitro was measured. Poly(ethylene argininylaspartate diglyceride) (PEAD) was synthesized as previously described (H. Chu, et al., A [polycation:heparin] complex releases growth factors with enhanced bioactivity, *Journal of controlled release: official journal of the Controlled Release Society*, 150 (2011) 157-163), e.g., as described in Example 1. To form the coacervate, 200 uL PRP was combined with 1.6 mg heparin (porcine intestine, Scientific Protein Labs, Waunakee, WI), allowing heparin-binding proteins to bind. The coacervate then self-assembled upon the addition of 8 mg PEAD in a total volume of 800 µL.

The coacervate was pelleted by centrifugation at 12,100×g for 10 minutes and initial growth factor loading was determined by measuring the concentration in the supernatant and comparing to the concentration prior to coacervate formation. Fresh 0.9% saline was added to resuspend the coacervate and samples were incubated at 37° C. At predefined time points extending to 21 days, the pelleting procedure was repeated and the supernatant collected for analysis. Fresh saline was then added to resuspend the coacervate.

Animals: Two 3-month old female Yorkshire pigs were used in this study. The pigs were fed standard lab diet twice per day with unrestricted access to water and their health was monitored at least twice daily for any signs of pain or distress. Following surgeries, pigs were housed individually to avoid perturbation of the wound sites.

Wounding Procedure: All surgical procedures were conducted under supervision of the Division of Laboratory Animal Resources (DLAR) at the University of Pittsburgh. Sedation was induced using an IM injection of ketamine (20 mg/kg) and xylazine (2 mg/kg) and anesthesia was maintained following intubation with 1-3% isofluorane. Twenty-two full-thickness excisional wounds were created on the back of each pig using 2 cm diameter biopsy punches to ensure consistent wound size (Shoney Scientific Inc, Waukesha, WI). The punch was driven into the fat layer underlying the dermis, and scissors were used to cut along the underlying fat and remove the skin section. Constant pressure was applied with sterile gauze to stop bleeding, using hemostatic collagen (Davol Inc, Warwick, RI) or epinephrine as needed.

Once the bleeding was stopped, Avitene Ultrafoam (Davol Inc, Warwick, RI) cut to fit the wound was applied, and group-specific treatment solution was added via sterile pipet. Upon addition of these solutions the collagen foam swelled to form a gel and retained the treatments within the wound site. Collagen foams have previously been used in these healing models and are used clinically to facilitate healing (D. Brett, A Review of Collagen and Collagen-based Wound Dressings, *Wounds: a compendium of clinical research and practice*, 20 (2008) 347-356). One of five treatments was applied to each wound: (1) saline, (2) unloaded coacervate, (3) bolus PRP, (4) full PRP coacervate, or (5) the heparin-binding fraction of PRP coacervate (HB-PRP) (n=8-10). Full PRP coacervate was formed by combining 400 µl PRP with 3.2 mg filter-sterilized heparin and 16 mg filter-sterilized PEAD. To isolate the HB-PRP coacervate, the full PRP coacervate was pelleted by centrifugation, the supernatant was aspirated and discarded, and the pellet was resuspended in fresh DI water. Wound treatments were assigned by forced randomization to account for any differences in the skin based on location, and each wound was assumed to be independent of other wounds and treatments (FIG. 1). All wounds received 5 mg ciprofloxacin administered topically to prevent infection.

Large Tegaderm bandages (3M, St. Paul, MN) were used to cover wound sites followed by Opsite transparent films (Smith & Nephew, London, UK) around the perimeter, forming a watertight dressing. A surgical pad sprayed with silicone-based medical adhesive (Hollister Inc, Libertyville, IL) was then applied on top of the entire wound area to protect the wounds and bandages, followed by a custom-fit jacket (Lomir Biomedical Inc, Malone, NY). Baytril (2.5 mg/kg) was administered IM once per day for seven days following surgery and amoxicillin (7 mg/kg) was administered orally twice per day for the remainder of the study to prevent infection. Carprofen (2 mg/kg) was administered for pain twice daily for five days following surgery. At days 3 and 7, the bandages were changed under brief sedation with ketamine (20 mg/kg) and xylazine (2 mg/kg).

Tissue Harvesting and Processing: Ten days after wounding the animals were sacrificed with an overdose of sodium pentobarbital (100 mg/kg) administered intravenously. Wounds were photographed for analysis before explant. No signs of infection were present in any wound. The wounds were harvested along with at least 1 cm of surrounding healthy tissue at the depth of the muscle fascia. Each wound was then cut in half sagittally prior to processing. For histology measurements and immunostaining of cytokeratin, tissues were fixed in 2% (w/v) paraformaldehyde for 2 hours and then transferred to a 30% (w/v) sucrose solution for cryoprotection for 24 hours. Tissues used for immunostaining of von Willebrand Factor (vWF) remained unfixed. All tissue samples were then embedded in optimal cutting temperature (OCT) media and frozen in liquid nitrogen-cooled 2-methylbutane. Tissues were then cryosectioned at 6 um for further analysis.

Measuring Overall Wound Contraction: Overall wound size was measured using images taken of the wound during the wounding procedure and after sacrifice. Wound area was measured using an automated filter and measurement macro in ImageJ and compared to the original wound area.

Histology: Tissue sections were stained with hematoxylin and eosin (H&E) for gross morphology and qualitative wound healing parameters such as thickness of granulation tissue and the formation of healthy skin structures. Masson's trichrome stain (MTS) was used to determine qualitative collagen deposition and alignment within the granulation tissue.

Immunostaining Tissue Sections: Immunofluorescent staining of tissue sections was used to determine the effect of each treatment on angiogenesis and reepithelialization. A rabbit polyclonal von Willebrand Factor (vWF) antibody (1:400 dilution, US Abcam, Cambridge, MA) followed by an Alexa Fluor 594 goat anti-rabbit antibody (Invitrogen, Carlsbad, CA) was used to detect endothelial cells within the tissue. Since healing is delayed in the center of the wound, images were taken at both the wound edge and the center for quantification. The number of $vWF^+$ cells was counted automatically using NIS Elements software (Nikon, Tokyo, Japan) and is reported as blood vessels per $mm^2$ area.

Reepithelialization of a wound reestablishes a functional barrier between the wound and its environment and is essential in preventing infection of the underlying tissue. Reepethelialization was quantified using a rabbit polyclonal cytokeratin antibody (1:100 dilution, US Abcam, Cambridge, MA) followed by an Alexa Fluor 594 goat anti-rabbit antibody. The length of the epidermal tongue was measured and reported as a percentage of the total wound length. All images were taken using a Nikon Eclipse Ti inverted microscope.

Statistics: All parameters were tested for significant differences between treatment groups using one-way independent analysis of variance (ANOVA) followed by Gabriel's post hoc testing with a significance value $p<0.05$. Analysis was performed using SPSS 22.0 software.

Results

Figure 2A:
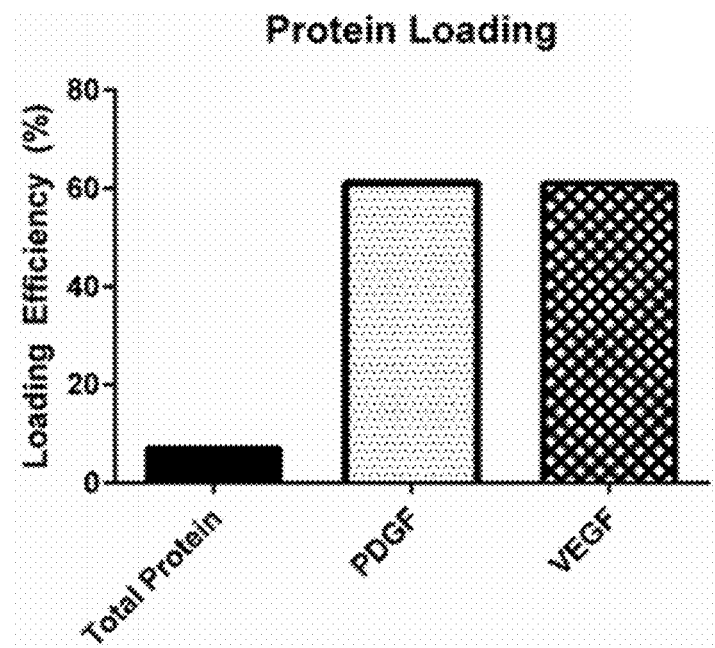
FIGS. 2A and 2B. Heparin-binding proteins preferentially load into the coacervate.
Figure 2B:
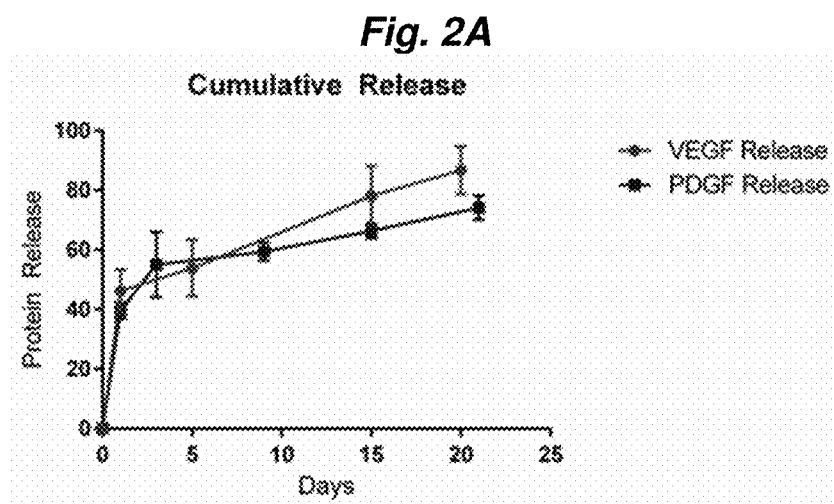

Coacervate system preferentially loads and releases heparin-binding growth factors: PEAD carries two positive charges per repeat unit. The polycation forms a complex coacervate when mixed with anionic heparin, visible as a turbid solution. The natural affinity between many therapeutic growth factors and heparin allows these proteins to preferentially load into the coacervate system. Although only 7% of total PRP proteins were loaded, heparin-binding VEGF and PDGF each exhibit a loading efficiency exceeding 60% (FIG. 2A). These proteins exhibited a burst release in the first day, followed by a nearly linear release over the following three weeks (FIG. 2B).

Figure 3:
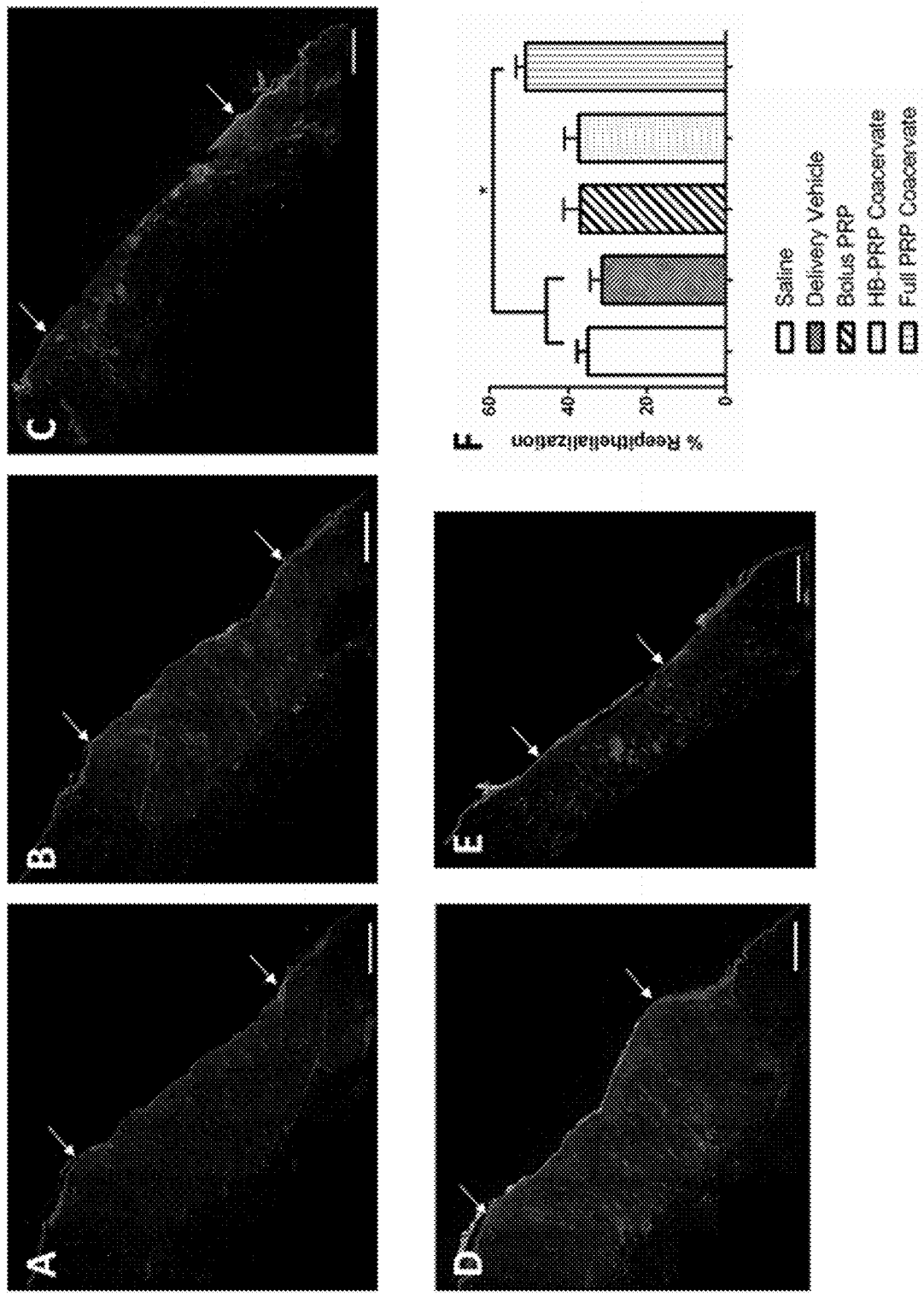
FIG. 3. Full PRP coacervate accelerates reepithelialization of wounds. Wound sections showing coverage by keratinocytes 10 days after treatment with (A) saline, (B) delivery vehicle, (C) free PRP, (D) HB-PRP Coacervate, or (E) PRP Coacervate. (F) Wound coverage at ten days is shown relative to the 10-day wound length. Wounds treated with PRP exhibit a 35% increase in reepithelialization compared to saline. Error bars indicate mean±SEM. Scale bars are 2 mm.

Full PRP coacervate accelerates pig wound closure: Porcine skin, like that of humans, heals primarily by reepethelialization. Immunofluorescent detection of cytokeratin for dermal epithelial cells showed a significantly increased reepithelialization rate (35% relative to saline) 10 days after wounding compared to saline and delivery vehicle alone (FIG. 3). No significant differences existed between other treatment groups. Wounds treated with full PRP coacervate also exhibited a thicker epidermis adjacent to the wound margin compared to other groups. Positive cytokeratin staining was also observed in sebaceous glands and hair follicles of healthy tissue as expected.

Figure 4:
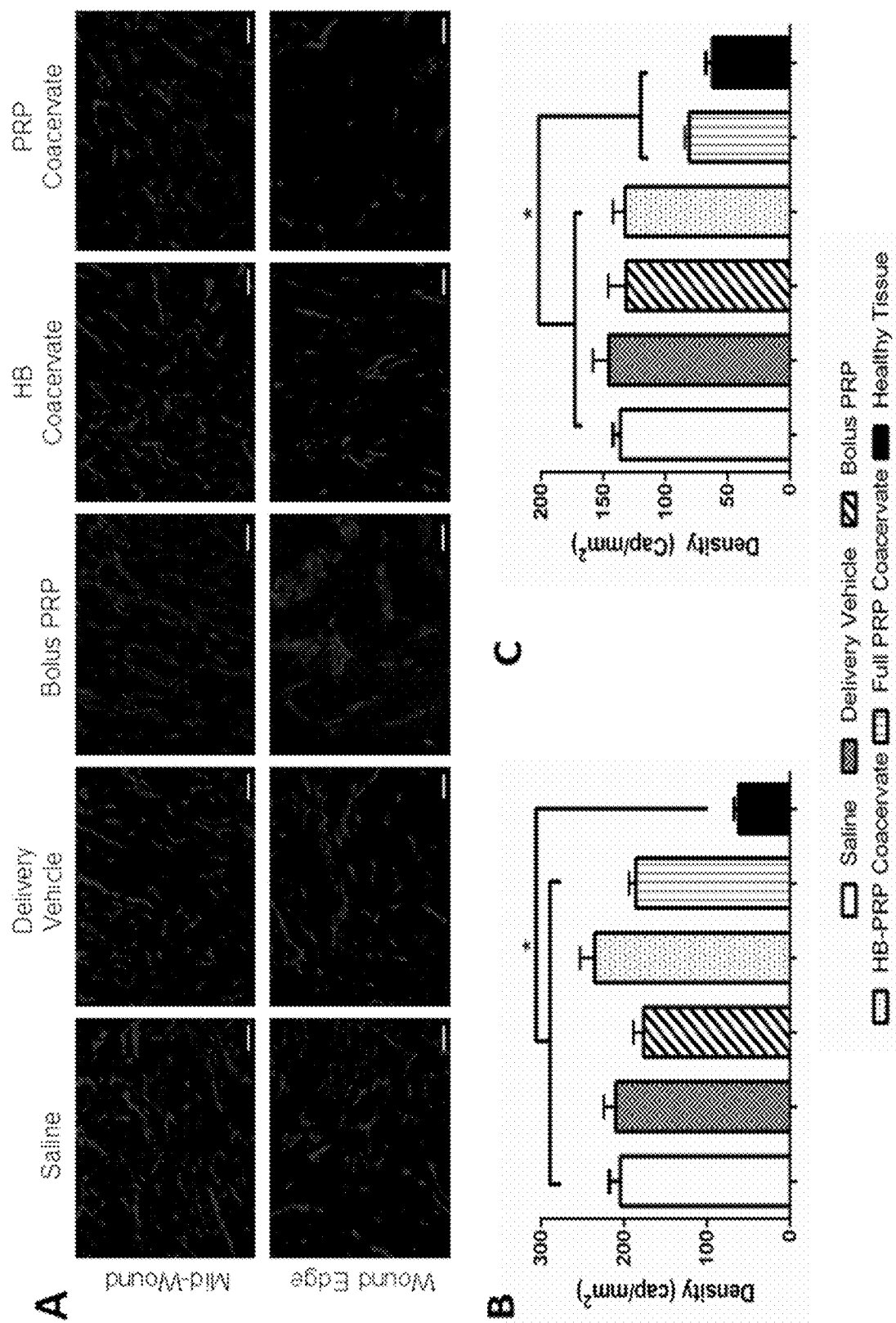
FIG. 4. Full PRP coacervate improves vascular maturity at the wound margin. (A) Staining with vWF for endothelial cells shows a high vascularity within all wounds with the exception of full PRP coacervate when imaged at the wound margin. (B) All wounds exhibit higher vascularity than healthy tissue mid-wound at 10 days. (C) When imaged at the wound margin, wound receiving full PRP coacervate have similar vascular density to healthy tissue while all other wounds exhibit a significant increase in vascularity. Scale bars=100 µm.

Full PRP coacervate modulates vascular density: The vascular density of the wounds was measured at day 10 using vWF immunofluorescence to identify endothelial cells. In the wound center, vascular density was significantly higher than in healthy tissue indicating an influx of blood vessels into the wound bed, and no significant differences between treatment groups were observed (FIG. 4 (A,B)). However, at the wound edges, blood vessel density of wounds treated with full PRP coacervate resembled that of uninjured tissue (FIG. 4(A)). Furthermore, the blood vessel density in full PRP coacervate treated wounds was significantly lower than all other treatment groups (FIG. 4 (A,C)). Since wounds heal more quickly at the edges, these data suggest that wounds treated with full PRP coacervate were at an advanced stage of healing compared to other treatments.

Figure 5A:
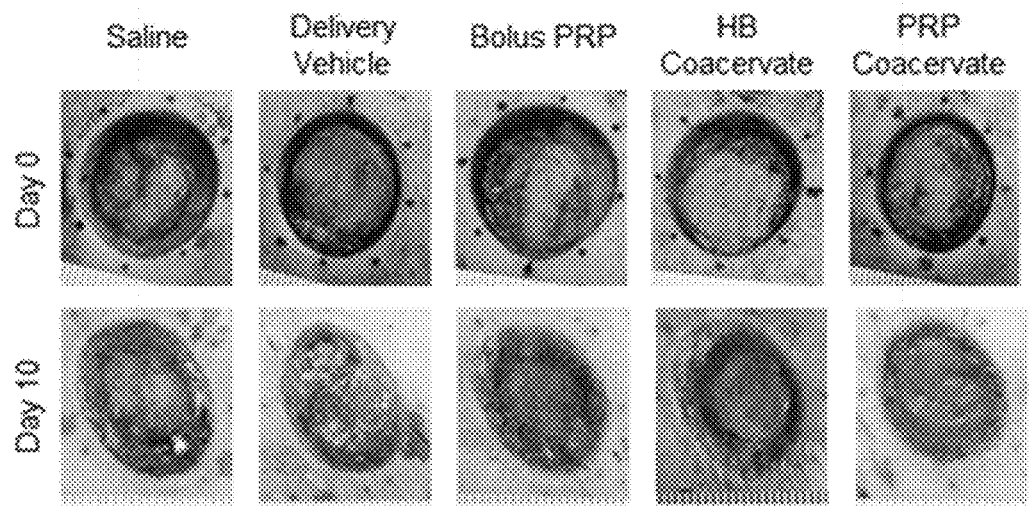
FIGS. 5A and 5B. Controlled release reduces overall wound size.
Figure 5B:
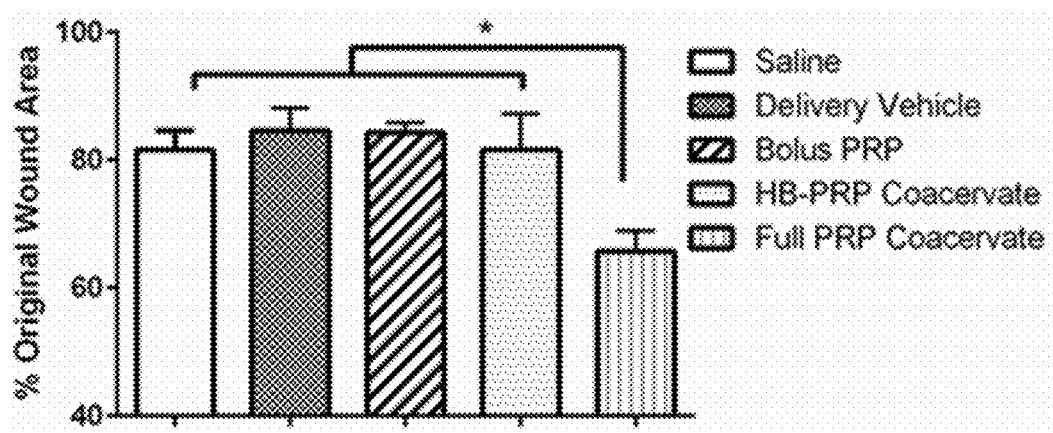

PRP coacervate decreases wound size: Wound closure was also analyzed macroscopically to confirm measurements made histologically. Automated measurements of wound area showed a significant decrease in wound size after ten days compared to all other treatments (65% original wound size for full PRP coacervate treated wounds compared to 83% when treated with saline). The remaining treatments did not cause a significant reduction in wound size (FIG. 5b). Further, wounds that did not receive full PRP coacervate treatment were visibly deeper and dark red in color, indicating unhealthy granulation tissue formation (FIG. 5a)(J. E. Grey, et al., Wound assessment, *BMJ,* 332 (2006) 285-288). The light pink color and raised appearance of granulation tissue seen in the full PRP coacervate wounds indicate healthy granulation. No signs of infection were present in any wound.

Figure 6:
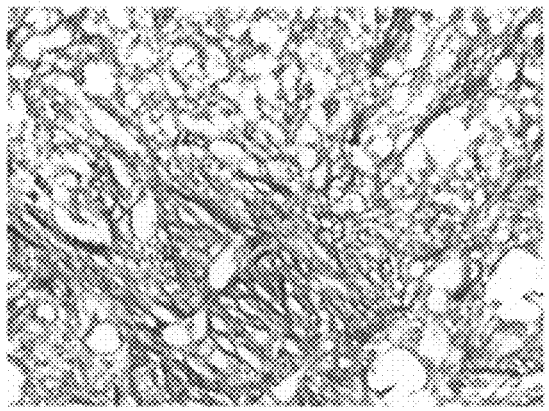
FIG. 6. Full PRP coacervate aligns collagen deposition. MTS images of tissues taken mid-wound show increased collagen alignment when treated with full PRP coacervate. Less gaps are also present as a result of this treatment. Scale bars are 50 µm.
Figure 6:
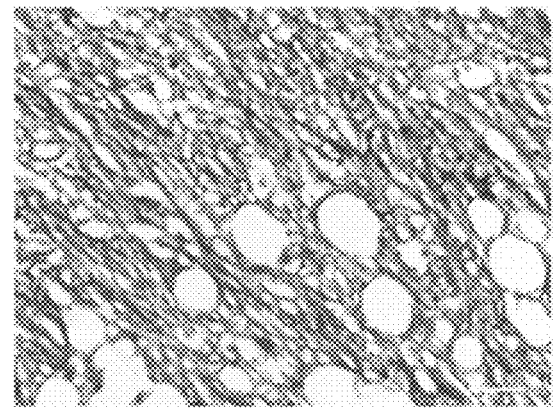
Figure 6:
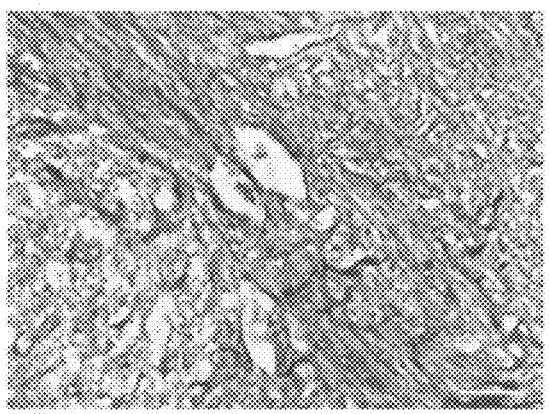
Figure 6:
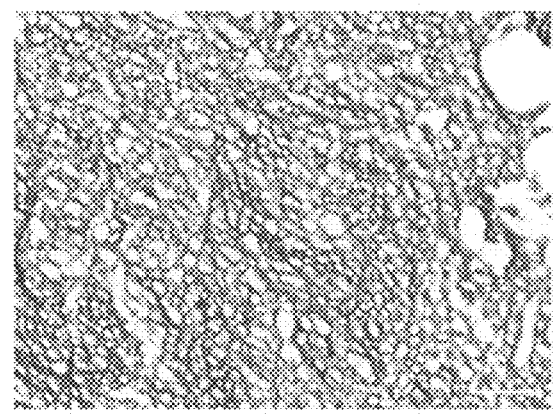
Figure 6:
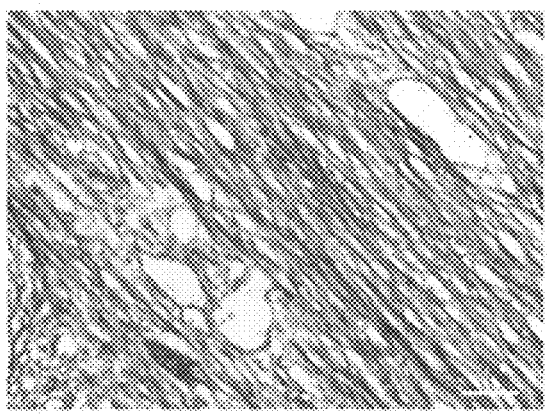

PRP Coacervate accelerates granulation tissue maturation: Granulation tissue provides a temporary matrix for cells to infiltrate and repair the wound bed after injury. As expected, H&E staining showed high cellularity and vascularity in the granulation tissue of all wounds relative to surrounding healthy tissue (not shown). Collagen deposition by fibroblasts had begun within 10 days in all wounds as seen by MTS (not shown). Upon careful evaluation it was evident that full PRP coacervate resulted in increased deposition of aligned collagen compared to other treatment groups where the collagen fibers were more randomly oriented (FIG. 6). The granulation tissue was thin in saline-treated control wounds, extending only partially to the normal skin surface.

DISCUSSION

The widespread use of PRP as a therapy remains highly debated in medicine. Autologous PRP is typically highly variable because of inherent differences between patients, methods of preparation, and whether it is used as a liquid or a thrombin-induced hydrogel. This leads to inconsistent results between patients and studies when used clinically as an autologous therapy. PRP activated by thrombin can be applied as a gel and has been described as a controlled release system to improve the efficacy of PRP. However, these studies have been restricted to small animal models or large animals models without sufficient characterization of protein release, and most have not been injectable (Y. Yan, et al., Acceleration of Full-thickness Wound Healing in Porcine Model by Autologous Platelet Gel, Wounds: a compendium of clinical research and practice, 19 (2007) 79-86). Provided herein is a systematic study of the effects of PRP in a porcine model and the benefits of controlled release for wound healing.

Appropriate controlled delivery systems are crucial to achieve high therapeutic efficacy of growth factors. Short half-lives, adverse off-target effects, and poor spatio-temporal control are common issues of bolus application which can be solved using controlled release systems. One approach is to harness the native properties of ECM molecules which sequester growth factors, prevent their degradation and promote their bioactivity (G. S. Schultz, et al., Interactions between extracellular matrix and growth factors in wound healing, *Wound Repair Regen*, 17 (2009) 153-162). Several different types of delivery platforms have been developed along this theme, utilizing ECM molecules vitronectin, fibronectin, and heparin. In one such platform, vitronectin complexes with insulin-like growth factor (IGF) and epidermal growth factor (EGF) demonstrated wound healing efficacy in large animals and safety in humans. In another approach, synthetic fibronectin-like peptides were developed to deliver several different heparin-binding growth factors and cytokines and evaluated in small animal studies. Our lab has characterized a heparin-based platform which takes the form of liquid coacervate droplets that load and release heparin-binding proteins (H. Chu, et al., A [polycation:heparin] complex releases growth factors with enhanced bioactivity, *Journal of controlled release: official journal of the Controlled Release Society*, 150 (2011) 157-163 and N. R. Johnson, et al., Lysine-based polycation: heparin coacervate for controlled protein delivery, Acta biomaterialia, 10 (2014) 40-46). HB-EGF delivered by the coacervate system accelerated healing in both diabetic and non-diabetic rodent wound models (N. R. Johnson, et al., Controlled delivery of heparin-binding EGF-like growth factor yields fast and comprehensive wound healing, *Journal of controlled release: official journal of the Controlled Release Society*, 166 (2013) 124-129 and N. R. Johnson, et al., Coacervate delivery of HB-EGF accelerates healing of type 2 diabetic wounds, *Wound Repair Regen*, 23 (2015) 591-600).

The use of multiple growth factors with the coacervate system has been explored previously to stimulate angiogenesis with VEGF and hepatocyte growth factor (HGF) (H. K. Awada, et al., Dual delivery of vascular endothelial growth factor and hepatocyte growth factor coacervate displays strong angiogenic effects, Macromolecular bioscience, 14 (2014) 679-686). The use of two growth factors exhibited a near-linear release profile over three weeks with no initial burst release. In comparison, both PDGF and VEGF from the PRP coacervate exhibit a 50% burst release within a day of coacervate formation (FIG. 2b) followed by a nearly linear release profile over 3 weeks. Interactions between heparin and growth factors are primarily charge-driven. When using small doses of proteins as was done previously, this interaction has negligible effects on the PEAD:heparin charge-based interaction. However, this study utilizes high protein concentrations; as more proteins bind to a heparin molecule, fewer sulfate groups are available to bind the PEAD polycation. Thus the coacervate formed is less stable than those formed with small protein doses. This allows the coacervate to dissociate at a faster rate, which likely explains the high initial release of proteins shown here.

Heparin has been used in many growth factor therapies since the heparin:growth factor complex is stable and resistant to proteolysis. Additionally, heparin potentiates the bioactivity of the proteins by facilitating their reactions with cell surface receptors. Its use in our delivery system provides the advantage of preferentially loading heparin-binding growth factors for sustained release. Although less than 10% of the total protein content of PRP was incorporated into the coacervate, heparin-binding proteins such as PDGF and VEGF exhibited a loading efficiency exceeding 60%. To our knowledge this is the first report of a PRP delivery system that is able to load and release heparin-binding growth factors in a sustained manner. We suspect that the non-heparin binding fraction of the platelet released factors provide important acute signaling for healing the tissue. Therefore, we tested the "full PRP coacervate" along with the heparin-binding fraction only, namely the "HB-PRP coacervate".

Prior studies utilizing heparin have largely involved its covalent immobilization to the surface of a polymeric scaffold or within a hydrogel, thereby endowing the biomaterial with growth factor affinity (S. E. Sakiyama-Elbert, Incorporation of heparin into biomaterials, *Acta Biomater*, 10 (2014) 1581-1587). However, covalent linkage may partially or fully inhibit the activity of heparin, reducing growth factor loading efficiency or creating a steric selectivity for heparin-binding protein of certain sizes or conformations. The coacervate platform employs heparin in free-form which maintains its native functionality and consistently provides high loading capacity. Furthermore, the heparin-binding complexes are mobile and able to interact with cell surface receptors and thereby potentiate growth factor bioactivity. In comparison, immobilized heparin may hold growth factors to a surface or deep within a scaffold that cells must infiltrate to access. A system using free heparin amphiphiles has also been reported, but their growth factor release has not been reported beyond 10 days (S. S. Lee, et al., Bone regeneration with low dose BMP-2 amplified by biomimetic supramolecular nanofibers within collagen scaffolds, *Biomaterials*, 34 (2013) 452-459 and K. Rajangam, et al., Heparin binding nanostructures to promote growth of blood vessels, Nano Lett, 6 (2006) 2086-2090). The advantages of the coacervate system are owed to the unique liquid-liquid phase separated structure held together by electrostatic interactions of heparin and the novel cationic polymer PEAD.

A porcine model of full-thickness excisional wounds is one of the best pre-clinical wound healing models as pig skin heals by similar mechanisms to human patients. Here we demonstrate that PRP itself is unable to improve wound healing; however the controlled release of its therapeutic proteins can accelerate the wound healing process. Wound vascularization and collagen fiber deposition and alignment in the granulation tissue indicated improved wound maturation in full PRP coacervate-treated wounds. Additionally, smaller gross wound size and enhanced reepithelialization shows that wound closure was also accelerated. Furthermore, we found that removal of non-heparin-binding proteins from PRP after coacervate formation reduced its efficacy. Interestingly, these data suggest that the non-heparin-binding PRP fraction plays a vital role in the healing response. The use of full PRP coacervate essentially creates two stages of release: an initial diffusion of all unincorporated PRP proteins followed by a sustained release of the heparin-binding growth factors. Sequential release of individual growth factors by the coacervate has been demonstrated to improve the therapeutic efficacy (H. K. Awada, et al., Sequential delivery of angiogenic growth factors improves revascularization and heart function after myocardial infarction, *Journal of controlled release: official journal of the Controlled Release Society*, 207 (2015) 7-17 and H. K. Awada, et al. Factorial Design of Experiments to Optimize Multiple Protein Delivery for Cardiac Repair, *ACS Biomaterials Science & Engineering*, 2 (2016) 879-886). The coacervate creates an analogous situation in the present study where high initial concentrations of unincorporated proteins induce a strong acute response followed by the sustained release of heparin-binding proteins which enact long-term effects. The removal of unincorporated proteins (as in the HB-PRP coacerate) reduces efficacy which could be due to a weaker acute response.

Angiogenesis is a vital component of the wound healing process. The formation of leaky capillaries allows cells and proteins to infiltrate the damaged tissue and begin healing. A high capillary density was observed in the center of all wounds assessed in this study, indicating the normal angiogenic process was not significantly disturbed. Since wounds heal from the edge, granulation tissue near the wound edge matures faster than the center of the wound where granulation tissue forms last. Therefore we are able to see a progression of the angiogenic process moving from the edge to the interior of the wound. The vessel density of all treatment groups was lower at the wound perimeter compared to the center, indicating that the wounds had progressed through the peak of angiogenesis and were returning to the levels of native skin. The difference arises in wounds treated with full PRP coacervate, where vessel density is similar to other wounds at the center but is significantly lower at the wound margin. This suggests that controlled PRP release accelerates the angiogenic phase of healing, returning vessel density to near-normal levels at a faster rate and exhibiting a more advanced stage of healing. This has significant relevance when comorbidities are present such as peripheral arterial disease or diabetes.

This study demonstrates the therapeutic benefits of controlled PRP release for wound healing applications. A quick and simple assembly method allows adaptability for either rapid autologous preparation at the bedside or an allogenic sourced off-the-shelf product. The liquid nature of our coacervate system allows it to be injected directly into the wound bed or incorporated into a substrate for application. The controlled release mechanism allows treatment to be applied once every few weeks rather than daily as seen in traditional protein therapies. Given the ability of this therapy to capture many proteins, this study suggests that the coacervate vehicle can be adapted to other therapeutic applications in large animal models.

In conclusion, this Example evaluated the efficacy of traditional PRP treatment and the advantage of a controlled release PRP formulation on cutaneous wound healing. It is shown that the sustained release of PRP proteins is able to significantly improve wound closure within 10 days of wounding, while the clinical standard of naked PRP proteins demonstrate no significant benefit. This is accompanied by a significant alteration in vascularity of the wound edge, returning vessel density to near-healthy levels. These results suggest that the controlled delivery of PRP proteins using the coacervate vehicle encourages accelerated healing of cutaneous wounds in a porcine model. The widespread use of PRP in humans combined with the clinical relevance of the porcine wound healing model emphasize the impact of this study on the translational potential to enhance autologous procedures with an easy-to-use protein delivery platform.

Example 3—Functional Recovery of the Infarcted Myocardium by a Single Injection of Three Proteins After a heart attack, the infarcted myocardium undergoes pathological remodeling instead of repair and regeneration. Protein signaling plays a pivotal role in tissue regeneration. With multiple pathologies developing after myocardial infarction (MI), treatment using several complementary proteins is expected to address these range of pathologies more effectively than a single-agent therapy. Three complementary factors are combined in one injection: tissue inhibitor of metalloproteinases 3 (TIMP-3) was embedded in a fibrin gel for signaling in the initial phase of the treatment, while basic fibroblast growth factor (FGF-2) and stromal cell-derived factor 1 alpha (SDF-1α) were embedded in a heparin-based coacervate and distributed within the same fibrin gel to exert their effects over a longer period of time. The spatiotemporally controlled release of these proteins counters excessive inflammation, extracellular matrix (ECM) degradation, and cell death post MI in rats. The contractility of the treated hearts stabilizes and slightly improves after a drop in the first two weeks whereas all the controls kept deteriorating. Accompanying the functional restoration are reductions in dilation, inflammation, fibrosis, and ECM degradation. Revascularization, cardiomyocyte survival, stem cell homing, and preservation of myocardial strain levels likely all contribute to the repair. This study demonstrates the potential of this multifactorial therapeutic approach in MI.

Myocardial infarction (MI) affects 7.6 million Americans with approximately 720,000 experiencing a heart attack each year. MI leads to defects in the contractile function of cardiomyocytes and alterations in the extracellular matrix (ECM) and ventricle geometry. As a consequence of the maladaptation, a non-contracting scar tissue forms, a significant portion of which results in congestive heart failure. Current treatments such as reperfusion, β-blockers, and angiotensin converting enzyme (ACE) inhibitors, reduce damage but do not restore function. Therefore, therapies that can prevent or reverse the multiple pathologies caused by MI, regenerate the myocardium, and restore cardiac function are urgently needed.

To treat multiple pathologies resulted from MI, we set out to explore the use of multiple therapeutic proteins. Our recent study using a statistical fractional factorial design of experiment focused our effort into the controlled and timed release of a combination of complementary proteins that are relatively distinct in their roles in cardiac function: tissue inhibitor of metalloproteinases 3 (TIMP-3), basic fibroblast growth factor (FGF-2), and stromal cell-derived factor 1 alpha (SDF-1α) (H. K. Awada, et al., Factorial Design of Experiments to Optimize Multiple Protein Delivery for Cardiac Repair. *ACS Biomaterials Science & Engineering* 2, 879-886 (2016). TIMP-3 inhibits the activity of matrix metalloproteinases (MMPs) which cleave ECM components. FGF-2 plays a chief role in formation of neovasculature. SDF-1α is a potent chemotactic factor that can recruit stem cells to the infarct region.

TIMP-3 reduces ECM degradation soon after MI. FGF-2 and SDF-1α promote angiogenesis and recruit progenitor cells to the infarct region, which are events that require prolonged signaling. We designed a composite hydrogel comprised of fibrin gel and heparin-based coacervates to achieve the sequential release of TIMP-3 followed by FGF-2 and SDF-1α. To achieve this controlled release, TIMP-3 was encapsulated in fibrin gel to offer early release, while FGF-2 and SDF-1α were encapsulated in heparin-based coacervates and distributed in the same fibrin gel to offer sustained release (FIG. 1A). Complex coacervates form spontaneously by electrostatic interactions between the aqueous solutions of a polycation and a polyanion. A synthetic polycation poly(ethylene argininylaspartate diglyceride) (PEAD), heparin, and heparin-binding proteins were used to form protein-loaded coacervates that have been shown to encapsulate proteins with high efficiency and sustain their release in vivo and in vitro.

In this study, the efficacy of the spatiotemporal delivery of TIMP-3, FGF-2, and SDF-1α on cardiac function, ventricular dilation and wall thinning, myocardial strain levels, MMP activity, fibrosis, inflammation, cardiomyocyte survival, angiogenesis, stem cell homing, protein signaling, and cell apoptosis. The first report of controlled delivery of complementary proteins mitigates the MI injury and initiates a robust cardiac repair process, giving hope of a higher level of functional and structural recovery of the infarcted heart.

Results

Figure 7:
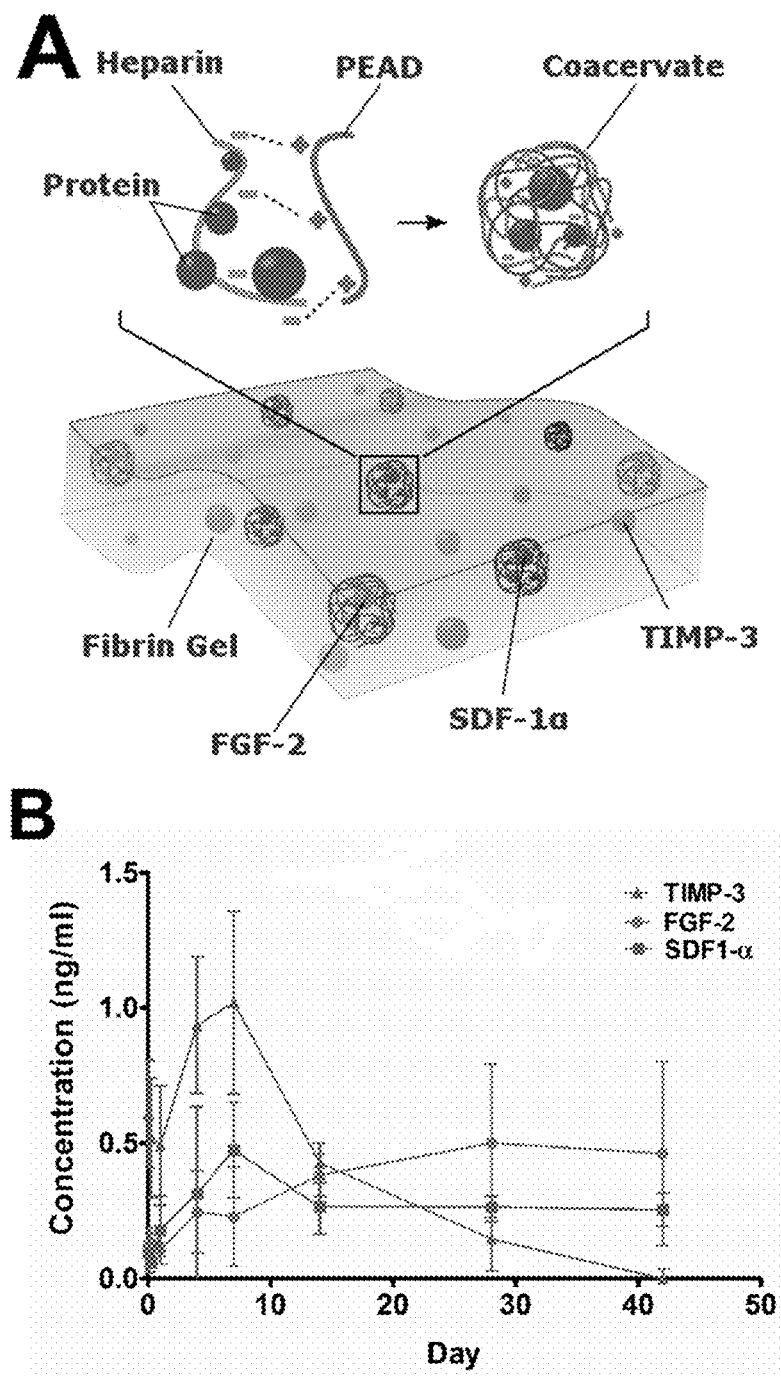
FIG. 7. Design and protein release kinetics of fibrin gel-coacervate composite. (A) The release system was comprised of a fibrin gel embedding TIMP-3 aimed for early release; and FGF-2/SDF-1α-loaded coacervates distributed within the same gel aimed for late release. The coacervate was formed through electrostatic interactions by combining FGF-2 and SDF-1α with heparin then with PEAD polycation. (B) The release system described achieved sequential quick release of TIMP-3 by one week followed by a sustained release of FGF-2 and SDF-1α up to six weeks. Data are presented as means±SD (n=3).
Figure 8:
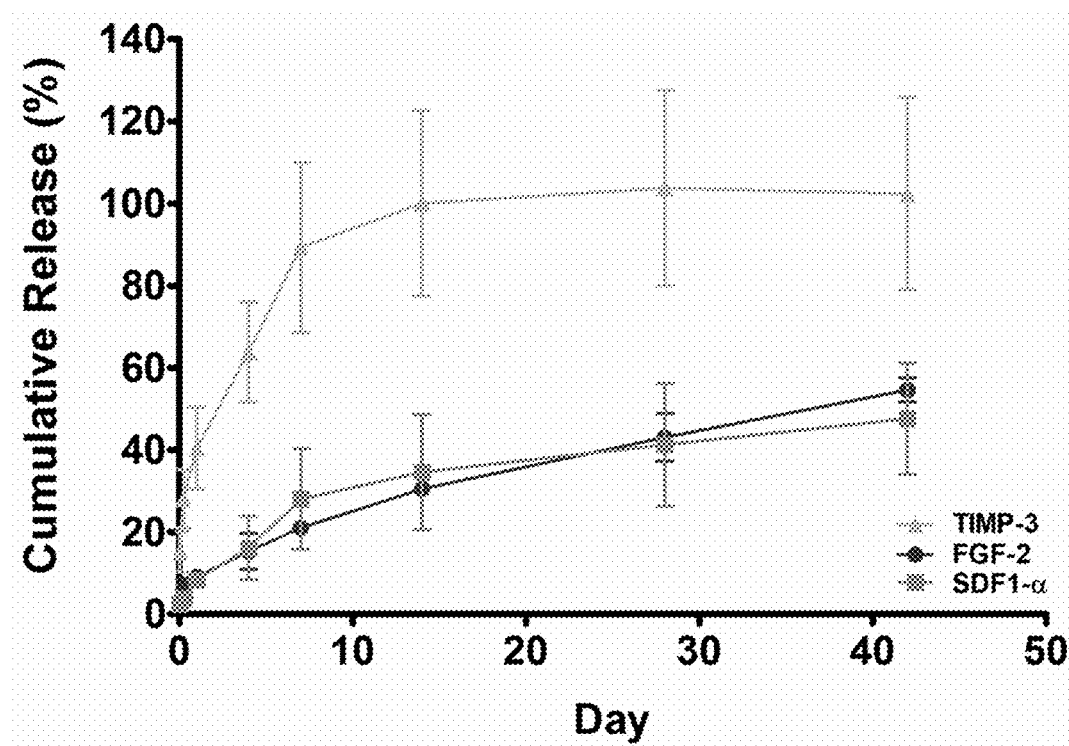
FIG. 8. Cumulative release profile of complementary proteins. The cumulative release plot of the complementary proteins shows the total percentage amount of each protein released with time. The plot shows quick release of TIMP-3 by one week followed by a sustained release of FGF-2 and SDF-1α up to six weeks. Data are presented as means±SD (n=3).

Sequential protein release: ability of a fibrin gel-coacervate composite to release TIMP-3 early followed by a sustained release of FGF-2 and SDF-1α by an in vitro release assay was tested (FIG. 7(A)). The loading efficiencies were 85% for TIMP-3, 97% for FGF-2, and 98% for SDF-1α (FIG. 8). By day one, approximately 40% of loaded TIMP-3 was released, reaching 90% total release by one week (FIG. 8) translating into relatively higher concentrations of TIMP-3 reaching a maximum of 1 ng/ml during the first week and decreasing thereafter (FIG. 7(B)). We observed a longer sustained release for FGF-2 and SDF-1α with concentrations between 0.25-0.5 ng/ml that lasted for >six weeks due to their encapsulation within the coacervates inside the gel (FIG. 7(B)). By one week, only 21% of FGF-2 and 28% of SDF-1α were released, reaching 55% and 48% total release respectively by six weeks (FIG. 8). Thus the composite coacervate gel achieved quick release of TIMP-3 after MI to reduce ECM degradation and inflammation, while providing FGF-2 and SDF-1α in a sustained manner for triggering a robust neovasculature formation process and stem cell recruitment.

Figure 9:
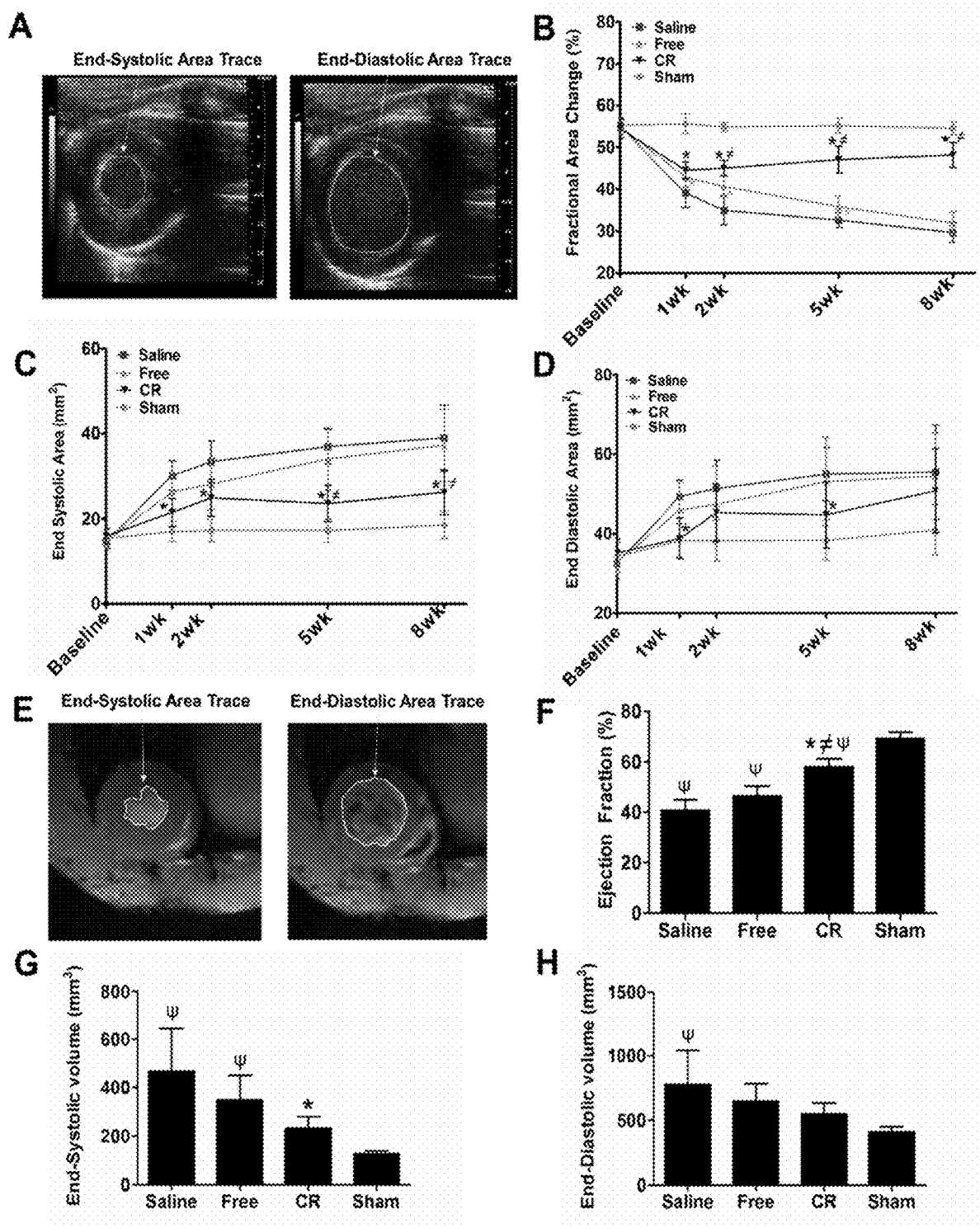
FIG. 9. Effect of controlled protein release on cardiac function and LV dilation. (A) Traces of ESA and EDA areas from short-axis B-mode images of the left ventricle using echocardiography. (B) FAC values show differences between groups after MI at multiple time points, with significantly higher FAC value of controlled release (CR) compared to saline and free proteins from two weeks onward. (C) Saline and free proteins groups show increasing ESA values, which were reduced in CR group. (D) Saline and free proteins groups show increasing EDA values, which were reduced in CR group. Data are presented as means±SD (n=9-10 per group). (E) Traces of ESA and EDA areas from short-axis view images of the LV using cardiac MRI. (F) EF values show differences between groups after MI at eight weeks, with significantly higher EF % of the CR group compared to saline and free proteins. (G) Saline and free proteins groups show increasing ESV value at eight weeks, which was significantly reduced in CR. (H) Saline and free proteins groups show increasing EDV value at eight weeks, which was reduced in CR. Data are presented as means±SD (n=5-8 per group). *$p<0.05$ vs saline, ≠$p<0.05$ vs free proteins, ψ$p<0.05$ vs sham.

Improved cardiac function and reduced ventricular dilation: The effect of spatiotemporal delivery of TIMP-3, FGF-2, and SDF-1α was evaluated in a rat MI model using sham, saline, and free proteins as controls. We evaluated changes in left ventricle (LV) contractility as a measure of heart function was evaluated. Using echocardiography, fractional area change (FAC) was computed from end-systolic area (ESA) and end diastolic area (EDA) values (FIG. 9(A)). Sham group maintained an FAC value of approximately 55% at all time points post-MI, significantly higher than all infarct groups (FIG. 9(B)). 1-week post-infarction, FAC values of saline, free protein, and controlled release (CR) groups dropped significantly, however, both CR and free proteins had significantly higher FAC than saline (p<0.01). This suggests that the three-proteins significantly improved cardiac function within one week after MI. At two weeks, CR group diverged from the negative controls and improved function significantly (p<0.001). Although free proteins was significantly better than saline (p<0.001) up to five weeks, function in both groups kept dropping. In contrast, functional improvement of CR group continued and displayed increasingly larger differences relative to the controls. At eight weeks, the last time point of the study, CR led to a 48% FAC, which was 87% that of the normal FAC value and represented a 74% improvement over saline. The two control groups, saline and free proteins, no longer showed any statistical difference at eight weeks (p>0.05) (FIG. 9(B)).

To evaluate the therapy's effect on ventricular dilation, changes in EDA and ESA values were assessed. The CR group showed significant reduction or trend towards lower EDA and ESA after MI compared to saline (FIG. 9(C,D)). On the other hand, saline and free protein groups showed progressively higher ESA and EDA at all time points after MI, with no statistical differences between them (p>0.05) (FIG. 9(C,D)).

The echocardiography results were consistent with MRI measurement at eight weeks. End-systolic volume (ESV) and end-diastolic volume (EDV) were computed and ejection fraction (EF) was calculated (FIG. 9(E)). EF in CR group was 58%, which was at 84% of the sham group (69%) and significantly higher (p<0.001) than saline (41%) and free proteins (46%). The two negative controls showed no difference between each other (p>0.05) (FIG. 9 (F)). Correspondingly, the left ventricle of the CR group was less dilated with a significantly smaller ESV than saline (p<0.01) and not significantly different from sham (FIG. 9(G)). CR also showed a trend towards lower EDV compared with saline and free protein groups (FIG. 9 (H)).

Figure 10A:
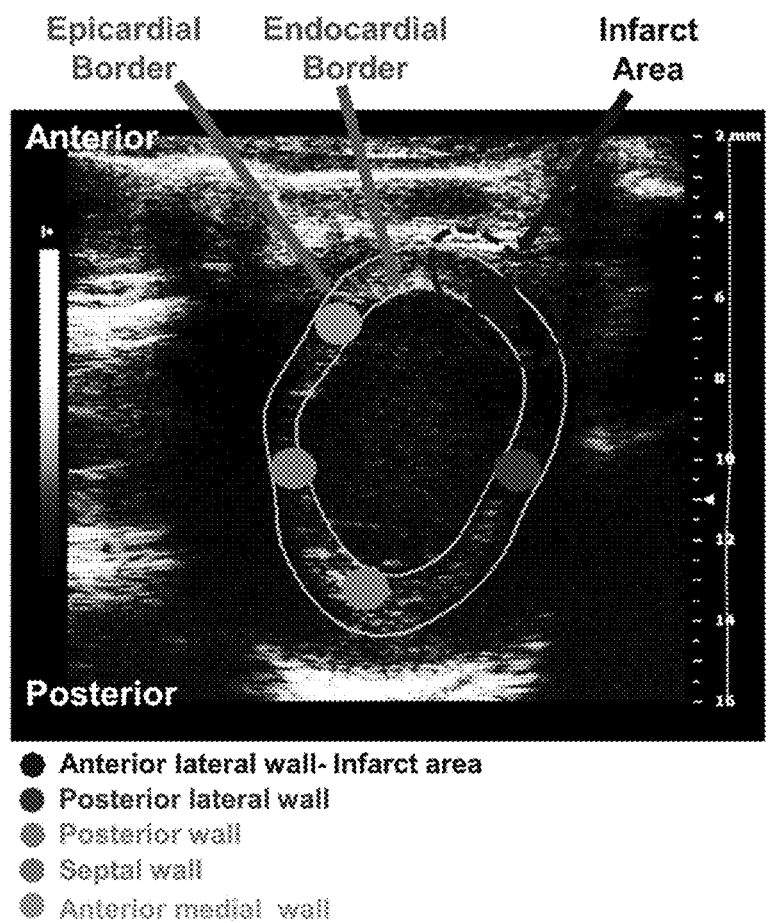
FIGS. 10A and 10B. Effect of controlled protein release on myocardial strain levels.
Figure 10B:
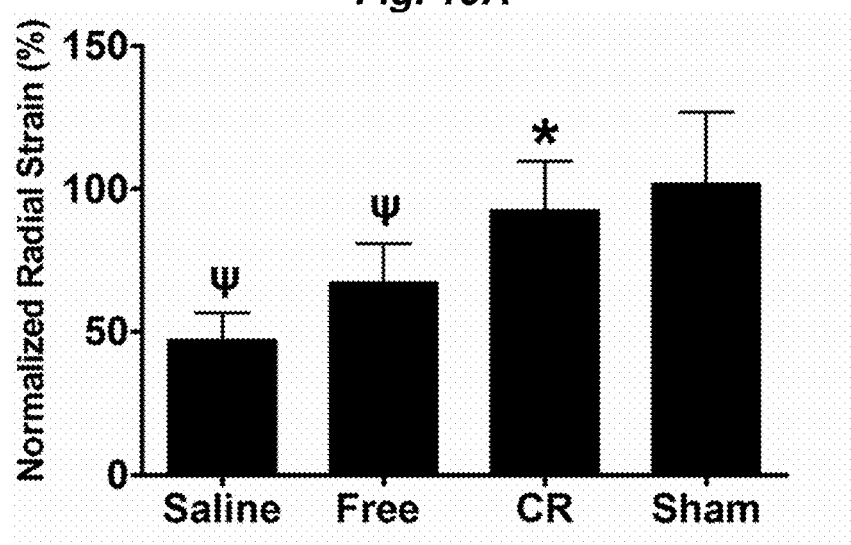

Preserved myocardial elasticity: Myocardial strain analysis at eight weeks post-MI to evaluate the changes in the radial strain levels of the myocardium with respect to the various treatments by normalizing the peak strain of the infarcted region to the average peak strain in four non-infarct regions (FIG. 10A). The radial strain, defined as the percent change in myocardial wall thickness, was measured. The CR group exhibited a radial myocardial strain similar to that of sham control (p>0.05), and was significantly higher than the saline group (p<0.01) (FIG. 10B). The free proteins group is similar to saline (p>0.05) and significantly less than sham (p<0.05)(FIG. 10B). This result suggests that controlled delivery of TIMP-3, FGF-2, and SDF-1α protects myocardial elasticity after MI. The prevention of ventricular wall stiffening helps to maintain the heart's ability to contract and dilate properly.

Figure 11:
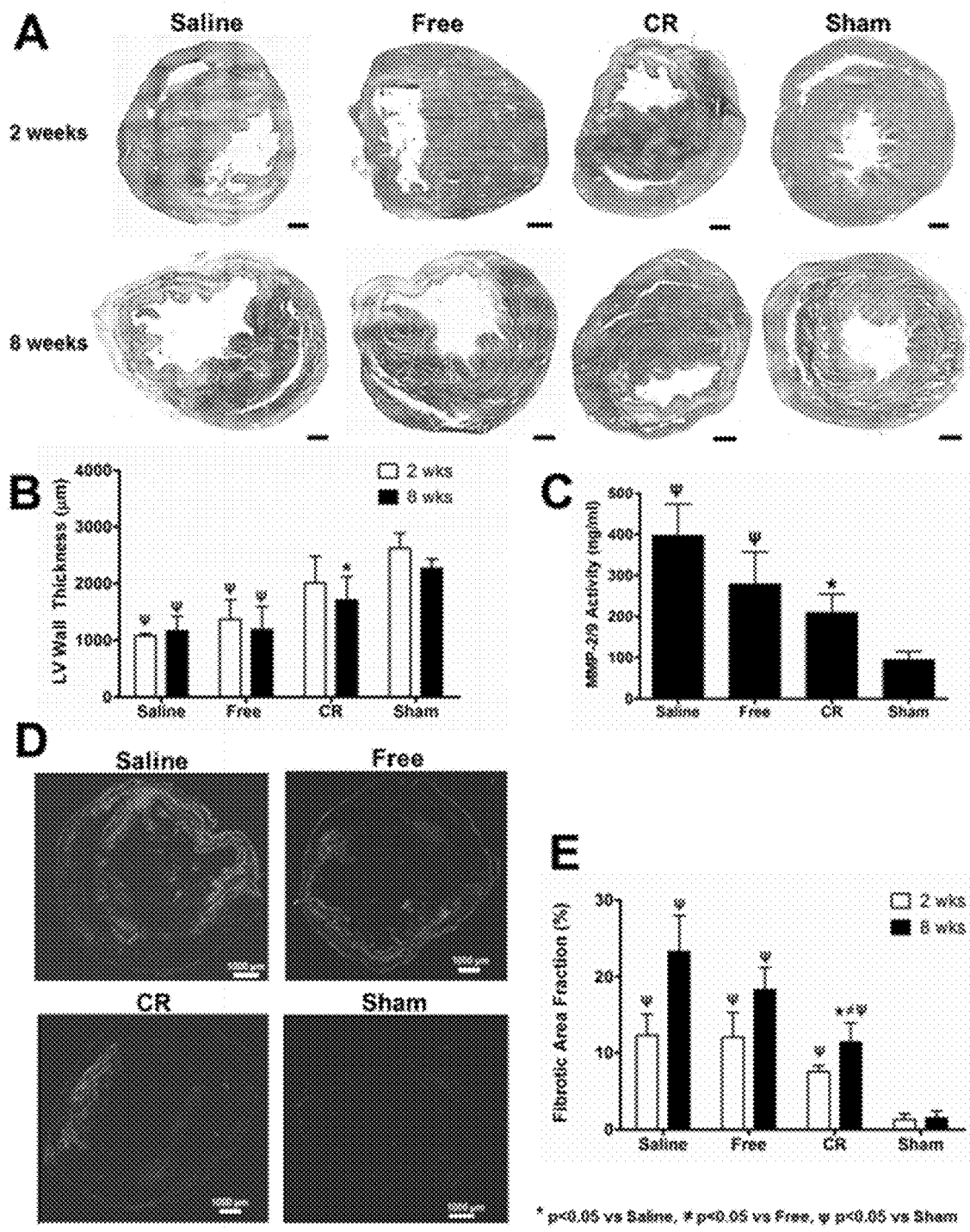
FIG. 11. Effect of controlled protein release on left ventricle wall thinning, MMP activity, and fibrosis. (A) Representative H&E images showed left ventricle (LV) wall thinning with damaged cardiac muscle surrounded by scar tissue in saline and free proteins groups at two and eight weeks. However, these damages were apparently alleviated in the CR group. Scale bar=1000 μm. (B) Quantitative analysis shows reduced ventricular wall thinning by CR at two and eight weeks over saline and free proteins groups. Data are presented as means±SD (n=3-4/group at two wks, n=4-6 at eight wks). (C) MMP-2/9 activity assay showed high levels of activity in infarct groups at eight weeks, but was significantly reduced in CR compared to saline. Data are presented as means±SD (n=3-4 per group). (D) Representative picrosirius red staining images (red in original) show the dense collagen deposition along the left ventricle wall and infarct zone in saline, followed by the free proteins group, whereas it was limited to the infarct region in CR at eight weeks. (E) Quantitative analysis shows that collagen deposition was not different in infarct groups at two weeks but was significantly less in CR compared to saline and free groups at eight weeks. Data are presented as means±SD (n=3-5/group at two wks, n=4-7 at eight wks). *p<0.05 vs saline, ≠p<0.05 vs free proteins, ψp<0.05 vs sham.

Reduced left ventricle wall thinning, MMP activity, and fibrosis: In order to understand tissue level changes that contributed to the functional improvement, ventricular wall thickness, MMP activity, and fibrosis were investigated at two and eight weeks. H&E stained hearts showed increased granulated scar tissue areas with thinner left ventricle walls in the infarct zone and borderzone that exacerbated with time in saline and free proteins groups but to a less extent in CR group (FIG. 11(A)). CR significantly prevented ventricular wall thinning at two weeks compared to saline (p<0.05) (FIG. 11(B)). In contrast, left ventricle wall thickness decreased considerably in saline and free proteins groups as early as two weeks. At eight weeks, there were no statistical differences in wall thickness between saline, free proteins, and CR; although CR clearly maintained a thicker wall average (FIG. 11(B)). CR wall thickness was not different from sham at both time points (p>0.05).

At eight weeks, we evaluated the activity of MMPs in the heart samples. MMP-2 and MMP-9 are important players implicated in many cardiovascular diseases and ECM degradation (T. Etoh, et al., Myocardial and interstitial matrix metalloproteinase activity after acute myocardial infarction in pigs. *American journal of physiology. Heart and circulatory physiology* 281, H987-994 (2001)). All infarct groups showed a high level of MMP-2/9 activity (FIG. 11(C)). However, CR showed significantly lower MMP activity compared to saline (p<0.01) and also lower activity than free proteins group but not to a significant level (p>0.05) (FIG. 11(C)). MMP activity in CR was not statistically different from sham (p>0.05). The enhanced reduction of MMP activity by the CR group is likely due to the controlled delivery of TIMP-3 within the fibrin gel-coacervate composite, where TIMP-3 can form tight complexes with MMP-2 and MMP-9 to prevent their activation, and thereby reducing ECM degradation and ventricular dilation and remodeling.

Figure 12:
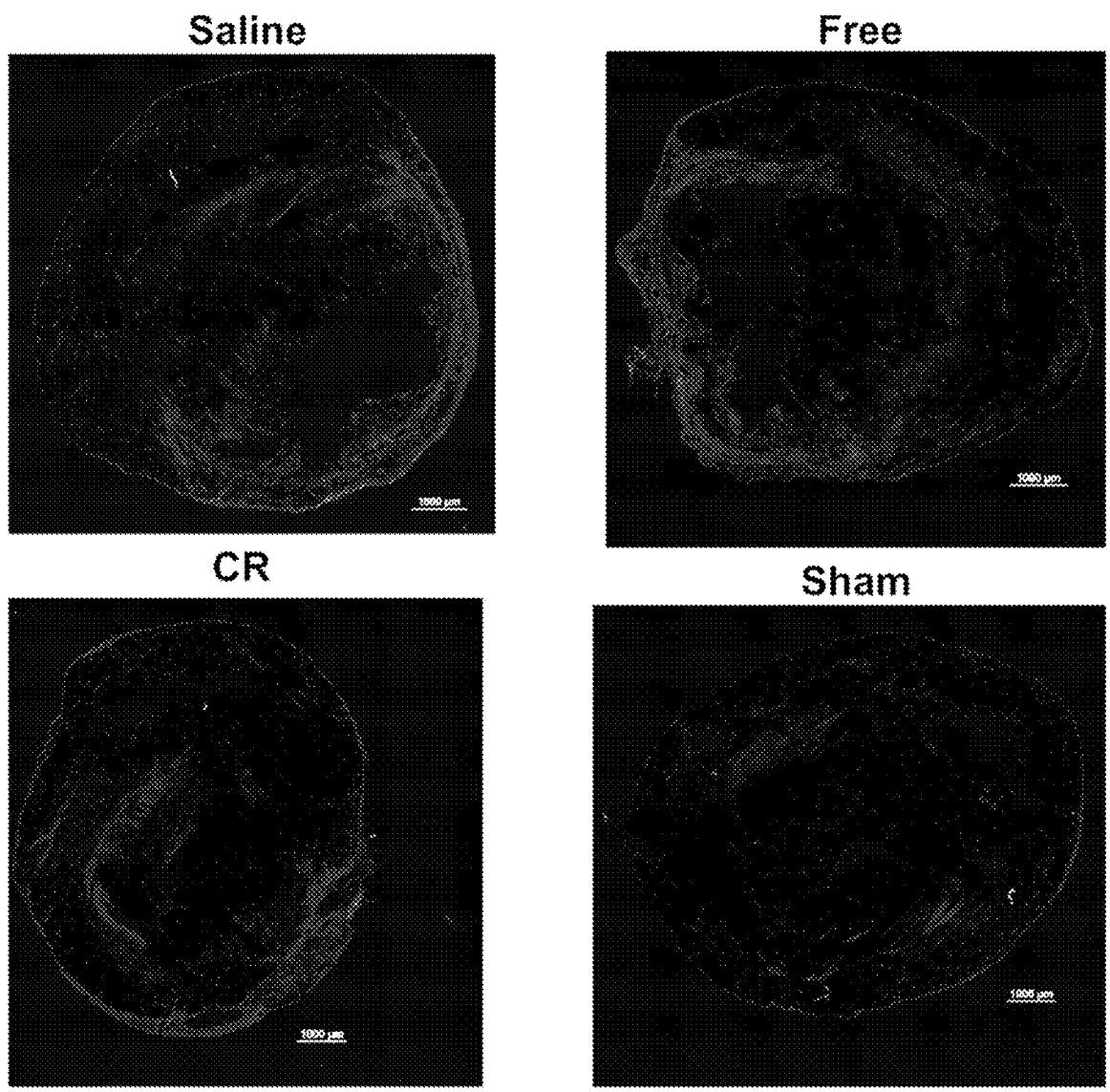
FIG. 12. Effect of spatiotemporal protein delivery on collagen deposition at 2 weeks. Representative picrosirius red staining images (red in original) show the extent of collagen deposition in the different groups at two weeks after MI.

Interstitial fibrosis develops at the infarct region and extends to non-infarct areas due to the excessive and uncontrollable collagen deposition that takes place in later stages after MI. This increased collagen deposition leads to increased stiffness in the myocardium, leading to contractile dysfunction. The extent of fibrosis was assessed using picrosirius red staining which stains collagen fibers (FIG. 11(D)). The saline group, and to a lesser degree the free proteins group, showed extensive amount of fibrosis that extended from the infarct to non-infarct regions, while CR showed far less fibrosis that seemed limited to the infarct area at two weeks (FIG. 12) and at eight weeks (FIG. 11(D)). Collagen deposition was quantified as a positive fraction of the heart area and no statistical differences were found between the infarct groups at two weeks despite a clear reduction in the CR group (p>0.05) (FIG. 11(E)). At eight weeks, collagen deposition increased in all infarct groups, but it was found to be significantly less in CR (11%) compared to both saline (23%) (p<0.01) and free proteins (18%) groups (p<0.01) (FIG. 11(E)). Sham had significantly less collagen than all groups at both time points.

Figure 13:
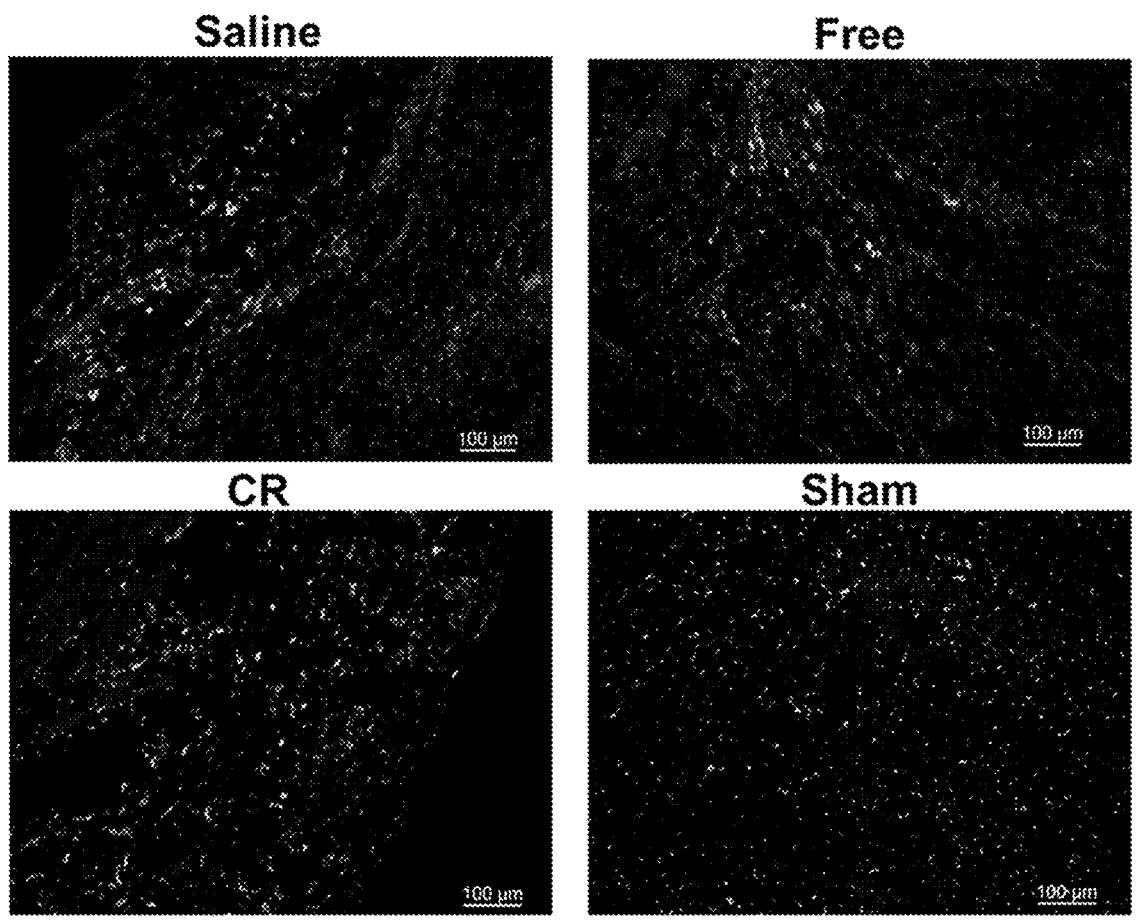
FIG. 13. Effect of controlled protein release on Inflammation. (A) Representative images of the different groups showing co-staining of F4/80 (red in original), a pan-macrophage marker, and CD163, an M2 macrophage marker (green in original) at two weeks. Co-localization of the two markers shows the color as yellow (in original). (B) The CR group shows a reduced number of non-M2 macrophages compared to saline and free proteins, but not statistically significant. (C) CR shows a significantly increased presence of M2 macrophages compared to saline. Data are presented as means±SD (n=3-4 per group at two wks). *p<0.05 vs saline, ψp<0.05 vs sham.
Figure 13:
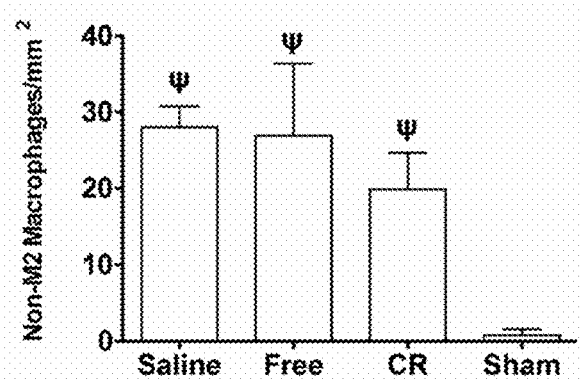
Figure 13:
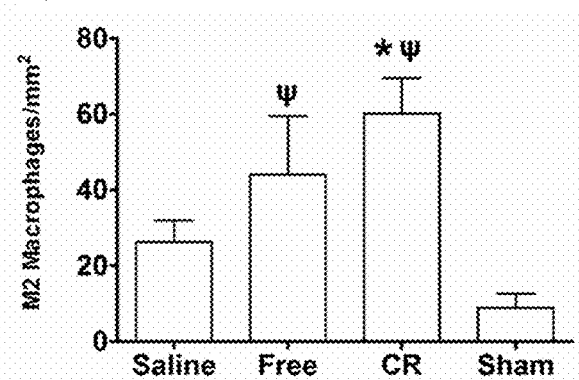

Reduced inflammation: Modulating the inflammatory response after MI in which certain harmful aspects of inflammation are prevented, can be very beneficial for the treatment of the infarcted myocardium. In this study, inflammation by co-staining for F4/80, a pan-macrophage cell surface marker, and CD163, an M2 macrophage marker (FIG. 13(A)) were assessed. Non-M2 macrophages, namely M1, promote inflammation, whereas M2 macrophages contribute to tissue repair and anti-inflammation J. M. Lambert, E. F. Lopez, M. L. Lindsey, Macrophage roles following myocardial infarction. *International journal of cardiology* 130, 147-158 (2008). At two weeks post-MI, CR showed a trend towards decreasing the presence of non-M2 macrophages, while they were present in high numbers in saline and free proteins groups (p>0.05) (FIG. 13(A,B)). On the other hand, CR significantly increased the presence of the beneficial M2 macrophages compared saline (p<0.01) (FIG. 13(A,B)). Saline and free proteins showed no statistical differences in their M2 macrophage numbers (p>0.05) (FIG. 13(A,B)). The sham control showed minimal presence of macrophages.

Figure 14:
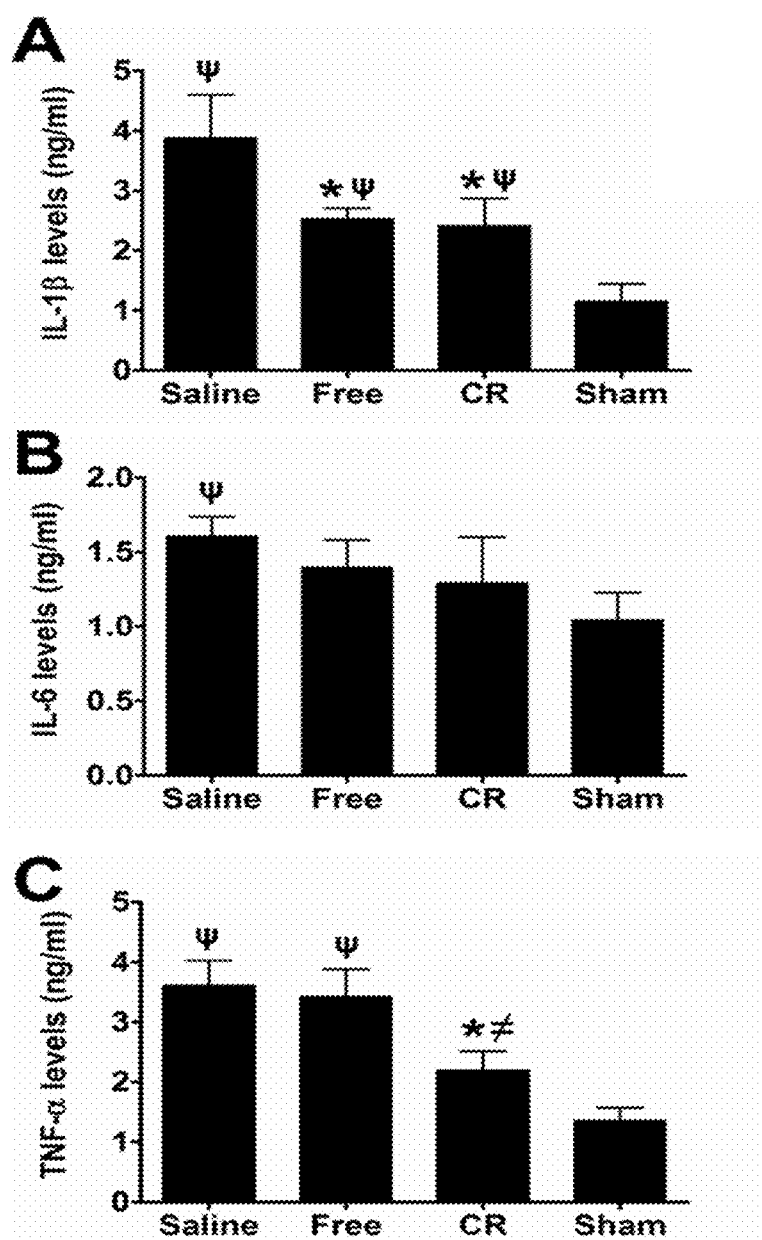
FIG. 14. Effect of spatiotemporal protein delivery on cytokine secretion levels at 8 weeks. Quantitative ELISA analysis shows (A) significant reduction in IL-1β levels in delivery and free proteins groups compared to saline, (B) no difference in IL-6 levels among the infarct groups, and (D) significant reduction in TNF-α level in delivery group compared to both saline and free proteins. Data are presented as means±SD (n=3-4/group at eight wks). *p<0.05 vs saline, ≠p<0.05 vs free proteins, ψp<0.05 vs sham.

The effect of the treatment on the secretion of pro-inflammatory cytokines was then investigated. Tissue lysates were tested at eight weeks for interleukin 1β (IL-1β), interleukin 6 (IL-6), and tissue necrosis factor α (TNF-α) (FIG. 14). Quantitative analysis by ELISA showed significantly lower levels of IL-1β in CR and free proteins groups (p<0.05) compared to saline (FIG. 14(A)). There was no statistical differences in the levels of IL-6 between the groups (p>0.05) (FIG. 14(B)). Finally, CR significantly reduced the levels of TNF-α compared to saline and free proteins (p<0.01), while the free proteins group was statistically indifferent to saline (p>0.05) (FIG. 14(C)). These results indicate the efficacy of the controlled release of TIMP-3, FGF-2, and SDF-1α at reducing the detrimental effects of an excessive inflammatory environment post-MI and at promoting tissue healing through polarization toward M2 macrophages.

Figure 15:
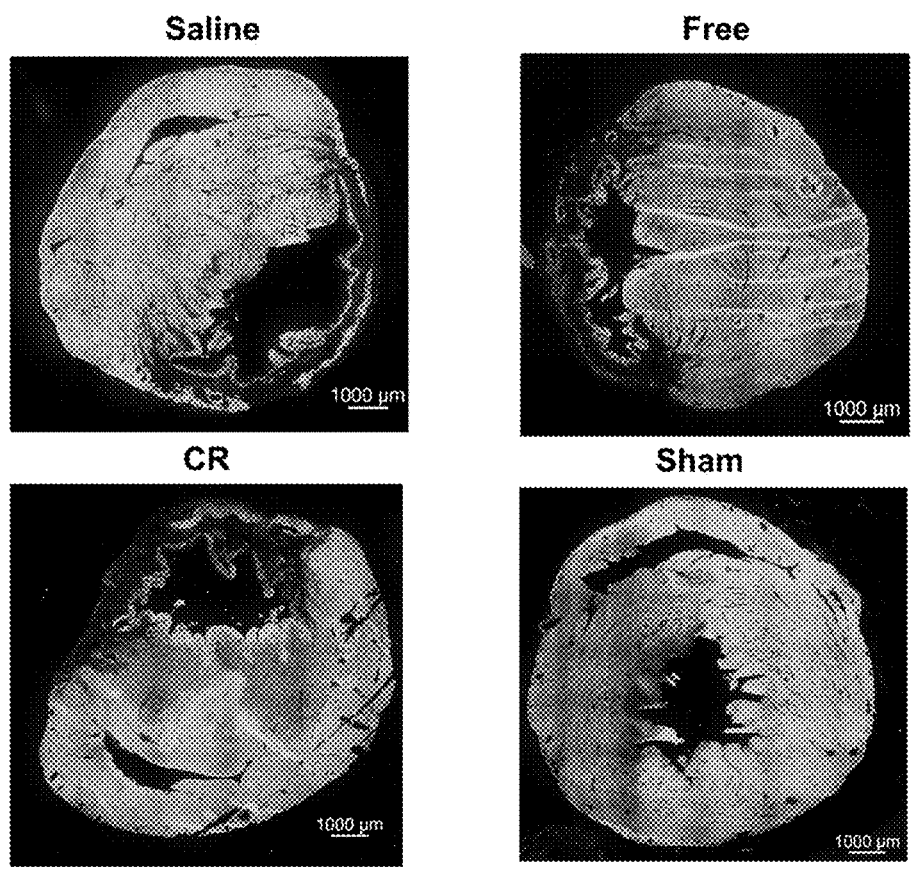
FIG. 15. Effect of spatiotemporal protein delivery on cardiac muscle viability at two weeks. Representative images of the different groups showing staining of viable cardiac muscle by cardiac troponin I (cTnI) (green in original) at two weeks after MI.
Figure 16:
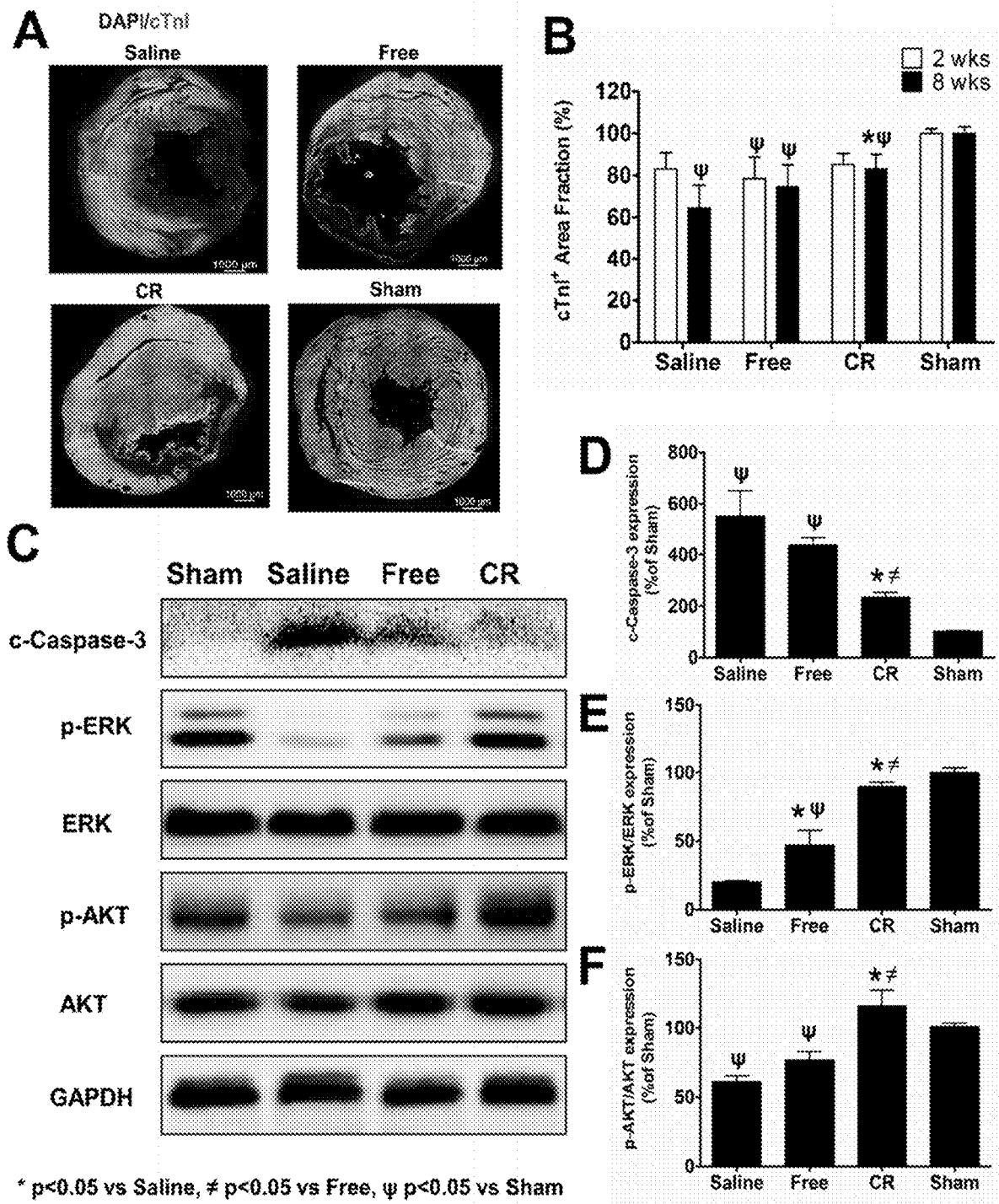
FIG. 16. Effect of controlled protein release on cardiomyocyte survival and apoptosis. (A) Representative images of the different groups showing staining of viable cardiac muscle by cardiac troponin I (cTnI) (green in original). Reduced viable muscle can be observed in all infarct groups, with better preservation of the muscle in the CR group at eight weeks. (B) Quantitative analysis shows no differences between infarct groups at two weeks, but demonstrates the CR group's significant preservation of cardiac muscle viability at eight weeks compared to saline. Data are presented as means±SD (n=3-5/group at two wks, n=5-6 at eight wks). (C) Representative western blot images of the expression levels of p-ERK, p-Akt and cleaved caspase-3 in study groups at eight weeks. (D) Intensity band analysis of cleaved caspase-3 shows significant reduction of expression level in CR compared to saline and free proteins groups. (E) Analysis of p-ERK1/2 shows significant increase of expression level in CR compared to saline and free proteins groups, with free showing significance over saline as well. (F) Analysis of p-Akt shows significant of expression level in CR compared to saline and free groups. Data are presented as means±SD (n=3/group at 8 wks). *p<0.05 vs saline, ≠p<0.05 vs free proteins, ψp<0.05 vs sham.

Increased cardiomyocyte survival and reduced apoptosis: The viability of the cardiac muscle is crucial for the proper function of the heart. Cardiomyocytes are responsible for imparting proper and synchronized contraction of the heart. As MI and the pathologies developed afterward trigger massive death of cardiomyocytes, it is beneficial to increase their survival, prevent their apoptosis, and trigger the regeneration of a viable myocardium. A major loss of viable myocardium was observed in the saline group, followed by the free proteins group, then by the CR group that apparently preserved the live cardiomyocytes to a larger extent at two weeks (FIG. 15) and at eight weeks (FIG. 16(A)). Quantitative analysis of the area fraction of the viable cardiac muscle demonstrated a reduction in the amount of survived cardiomyocytes in all infarct groups at two weeks, with no statistical differences between them (p>0.05) (FIG. 16(B)). At eight weeks, the viability of the cardiac muscle was reduced more in the saline group (64% viable muscle), followed by the free proteins group (75%) with no significant differences between them (p>0.05). In contrast, CR was able to maintain the survival of the cardiac muscle (83%) significantly better than saline at eightweeks (p<0.01) (FIG. 16(B)).

A number of molecular pathways play important roles in promoting survival or inducing apoptosis of cells. The activated (phosphorylated) MAPK/ERK and Akt pathways have been shown to be cardioprotective after ischemia and preventive of apoptosis (A. Kis, et al., Second window of protection following myocardial preconditioning: an essential role for PI3 kinase and p70S6 kinase. *Journal of molecular and cellular cardiology* 35, 1063-1071 (2003); A. Tsang, et al., Postconditioning: a form of "modified reperfusion" protects the myocardium by activating the phosphatidylinositol 3-kinase-Akt pathway. Circulation research 95, 230-232 (2004); and Y. Wang, Mitogen-activated protein kinases in heart development and diseases. Circulation 116, 1413-1423 (2007)). To analyze the effect of our treatment, we quantified the expression levels of cleaved caspase-3, a pro-apoptosis mediator, and pro-survival markers p-ERK1/2 and p-Akt at 8 weeks by western blotting (FIG. 16(C)). Among infarcted animals, the CR group had the lowest level of cleaved caspase-3 and the highest levels of p-ERK1/2 and p-Akt (FIG. 16(C)). The free proteins group displayed significantly higher p-ERK1/2 expression than saline (p<0.01) (FIG. 16(D)). However, CR significantly reduced the expression of cleaved caspase-3 and increased the expression of p-ERK1/2 and p-Akt compared to both saline (p<0.001) and free proteins (p<0.01) groups (FIG. 16 (D,E, F)). CR was statistically indifferent to sham in all three cases. Taken together, these results demonstrate the effectiveness of the approach described herein at supporting the long-term survival of cardiomyocytes, preventing their apoptosis, and providing overall cardioprotection after MI through activation of the Akt and ERK1/2 signaling pathways and the suppression of caspase-3 mediated apoptosis.

Figure 17:
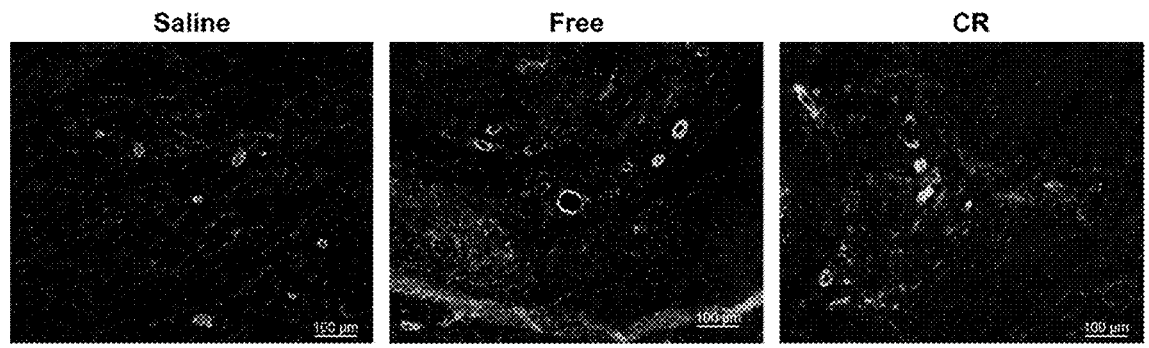
FIG. 17. Effect of spatiotemporal protein delivery on angiogenesis at two weeks. Representative images of the infarct groups showing co-staining of vWF (red in original), an endothelial marker, and α-SMA (green in original), a pericyte marker at two weeks after MI.

Enhanced angiogenesis: The revascularization of the ischemic myocardium is key to tissue regeneration and functional recovery. New blood vessel formation can help restore the blood, nutrient, and oxygen flow to the damaged myocardial regions, and thereby enhance the survival of cardiomyocytes, and reduce the risk of chronic heart failure. To investigate the process of angiogenesis, tissue slices were co-stained for vWF and α-SMA at two weeks (FIG. 17) and eight weeks (FIG. 18(A)). Angiogenesis was evaluated only in the infarct groups, and not in sham since angiogenesis happens after infarction and not in healthy hearts. A higher number of neovessels was observed in the CR group compared to saline and free proteins (FIG. 18(A)). Quantitative analysis of infarct groups showed significantly higher number of vWF-positive vessels in CR compared to saline at two weeks ($p<0.05$) (FIG. 18(B)). At eight weeks, CR showed a significantly higher number of vWF-positive vessels than both saline and free proteins groups ($p<0.01$) (FIG. 18(B)).

Figure 18:
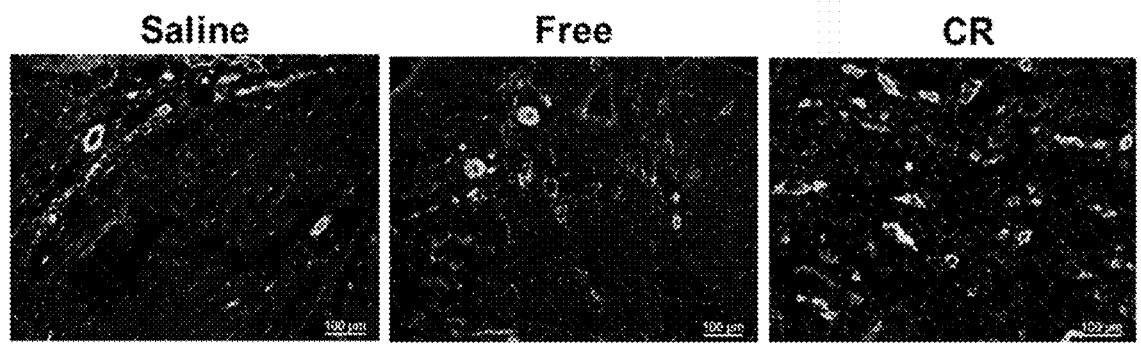
FIG. 18. Effect of controlled protein release on angiogenesis. (A) Representative images of the different groups showing co-staining of vWF (red in original), an endothelial marker, and α-SMA (green in original), a pericyte marker at eight weeks. (B) CR shows a significantly greater number of vWF+ vessels compared to saline at two weeks and compared to saline and free proteins at eight weeks. (C) CR shows a significantly greater number of vWF$^+$ α-SMA$^+$ vessels than saline and free proteins groups at eight weeks but not at two weeks. Data are presented as means±SD (n=3-4/group at two wks, n=5-6 at eight wks). *p<0.05 vs saline, ≠p<0.05 vs free proteins.
Figure 18:
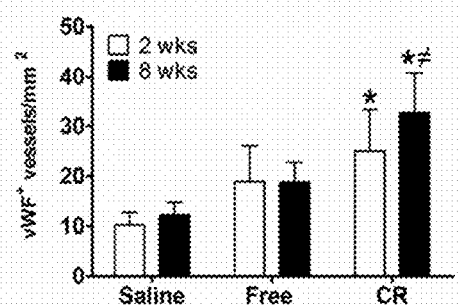
Figure 18:
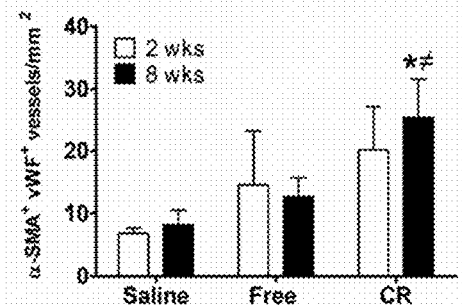

Co-localization of vWF and α-SMA was used as markers of mature neovessels, and no significant differences was found among the infarct groups at two weeks ($p>0.05$) (FIG. 18(C)). However, at eight weeks, CR showed significantly higher presence of mature neovessels than saline and free proteins groups ($p<0.001$) (FIG. 18(C)). Our results demonstrate the ability of our treatment to induce robust angiogenesis with stable and mature neovasculature. This enhanced revascularization in the CR group is likely due to the sustained presence of the potent angiogenic factor FGF-2 being provided by the heparin-based coacervate within our composite gel.

Figure 19A:
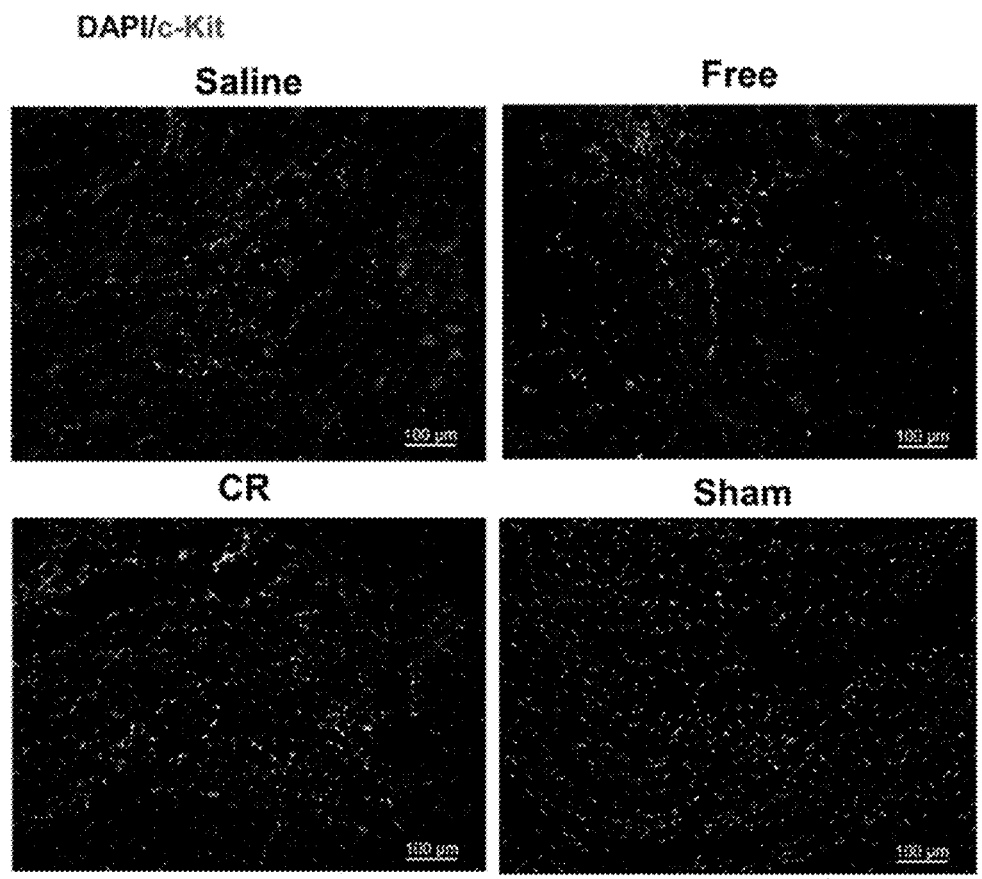
FIGS. 19A and 19B. Effect of controlled protein release on stem cell homing.
Figure 19B:
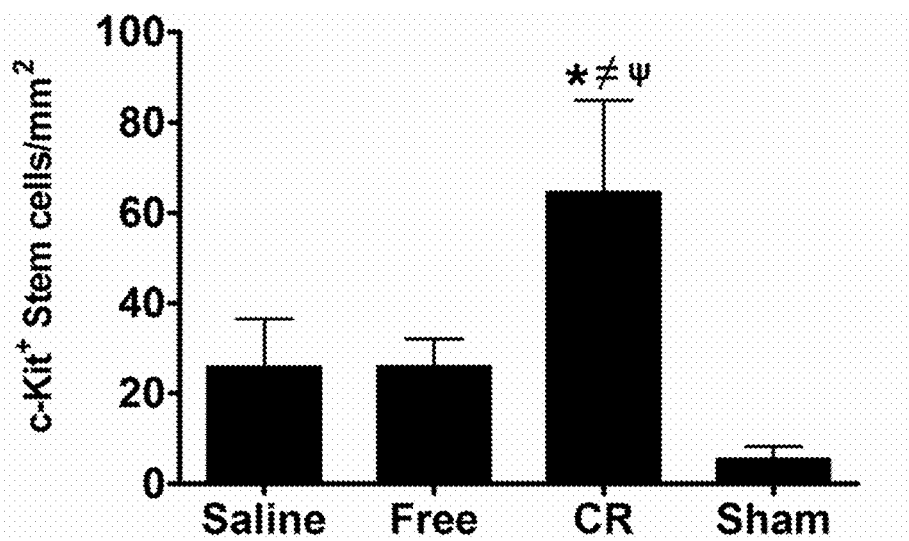

Greater stem cell homing to the myocardium: Stem cells recruited to the infarcted myocardium have the potential to differentiate into functional cells of cardiac lineages such as cardiomyocytes, vascular endothelial, and mural cells. Stem cells can also impart beneficial paracrine effects that activate repair and regeneration signaling (K. Malliaras, et al., Cardiomyocyte proliferation vs progenitor cells in myocardial regeneration: The debate continues. *Global cardiology science & practice* 2013, 303-315). To examine the homing of stem cells to the infarcted myocardium, c-Kit, a stem cell marker was stained for (FIG. 19A). At eight weeks after MI, saline and free proteins groups showed no significant differences in the number of c-Kit-positive cells present at the borderzone ($p>0.05$) (FIG. 19B). In contrast, the CR group showed a significantly greater presence of c-Kit-positive cells at the borderzone compared to both saline and free proteins groups ($p<0.01$) (FIG. 19B). The sham control showed very few stem cells in the area where an infarct would have been induced, suggesting their limited presence in absence of an MI injury. These results indicate the efficacy of the controlled release approach at recruiting stem cells to the infarct region to potentially contribute in the repair and regeneration of the myocardium. The enhanced and long-term presence of stem cells in the CR group is likely due to the sustained availability of the powerful chemoattractant SDF-1a within the composite gel.

Figure 20:
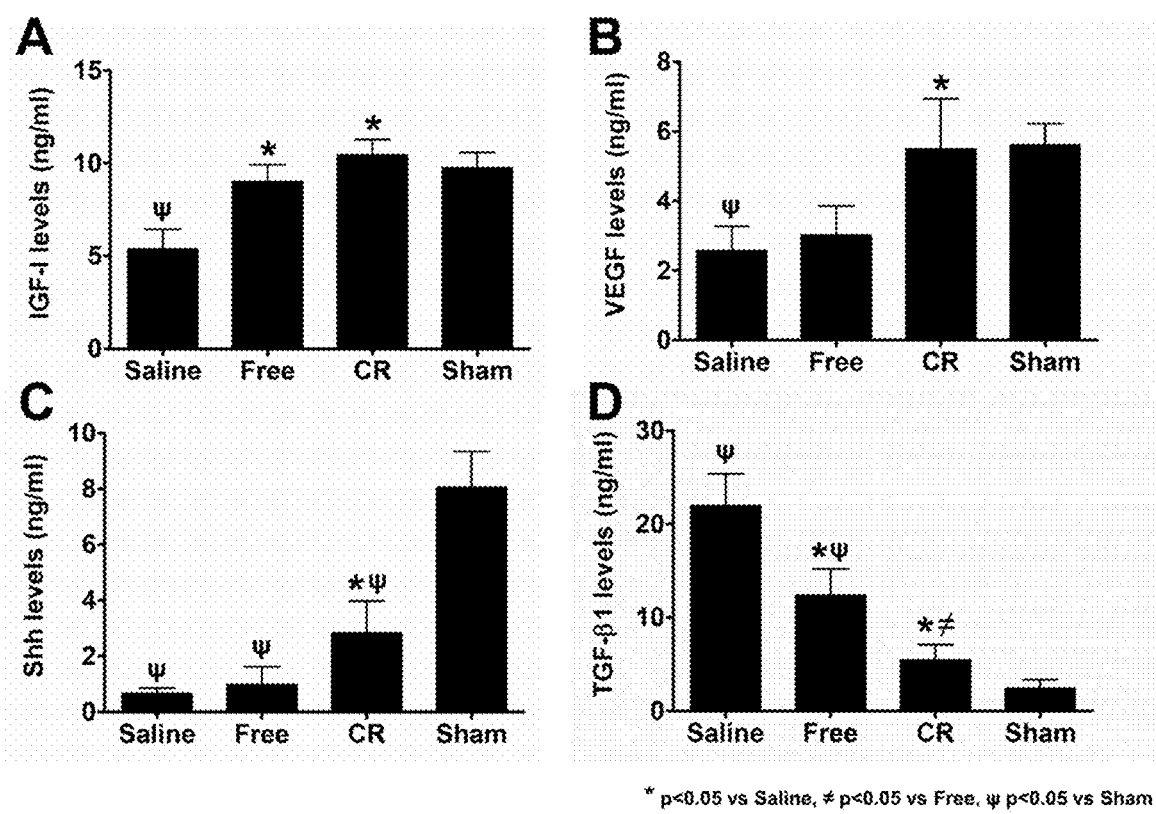
FIG. 20. Effect of spatiotemporal protein delivery on secretion levels of relevant proteins at eight weeks. Quantitative ELISA analysis shows that (A) Free proteins and CR groups significantly increased IGF-I levels, (B) CR significantly increased VEGF levels compared to saline, (C) CR significantly increased Shh levels compared to saline, and (D) Free proteins group significantly decreased TGF-β1 levels compared to saline, but delivery group significantly decreased TGF-β1 levels compared to both saline and free proteins. Data are presented as means±SD (n=3-4/group at eight wks). *p<0.05 vs saline, ≠p<0.05 vs free proteins, ψp<0.05 vs sham.

Secretion of key signaling proteins: Certain proteins are involved in triggering cardiac repair mechanisms and others are implicated in advancing pathological changes post infarction. Therefore, regulation of the secretion levels of such proteins represents an important aspect of effective therapies. The presence of proteins such as the ones in the complementary combination, TIMP-3, FGF-2, and SDF-1α, described herein likely affect the signaling and secretions levels of other proteins in the heart after MI. To investigate the effect of our treatment on the levels of relevant proteins, tissue lysates were tested for the levels of insulin-like growth factor-I (IGF-I), vascular endothelial growth factor (VEGF), sonic hedgehog (Shh), and transforming growth factor-β1 (TGF-β1) at eight weeks (FIG. 20). Quantitative analysis by ELISA showed significantly higher levels of IGF-I, an anti-apoptotic factor, in CR ($p<0.001$) and free proteins ($p<0.01$) groups compared to saline (FIG. 20(A)). Moreover, CR significantly increased the levels of VEGF, a potent angiogenic factor, and Shh, a master cardiac morphogen, over saline ($p<0.05$), while the free proteins group was statistically indifferent to saline ($p>0.05$) (FIG. 20 (B,C)). Lastly, CR significantly decreased the levels of TGF-β1, a pro-fibrotic factor, compared to saline ($p<0.001$) and free proteins ($p<0.05$) groups (FIG. 20(D)). The free proteins group also significantly decreased the levels of TGF-β($p<0.05$) (FIG. 20(D)).

MI results in multiple pathologies and maladaptive remodeling of the heart. Numerous efforts toward cardiac repair and regeneration are underway. Stem cell-related technology can provide new cardiomyocytes via direct reprogramming and paracrine signaling via cell injection. Proteins and nucleic acids can alter the composition of local signaling molecules and enhance repair and regeneration (H. B. Sager, et al., RNAi targeting multiple cell adhesion molecules reduces immune cell recruitment and vascular inflammation after myocardial infarction. *Science Translational Medicine* 8, 342ra380-342ra380 (2016). Tissue-engineered patches can combine cells, growth factors, and mechanical signal to provide comprehensive cues to restore structure and functions of the heart (B. M. Ogle, et al., Distilling complexity to advance cardiac tissue engineering. *Science Translational Medicine* 8, 342ps313-342ps313 (2016)). Proper spatial and temporal signals of proteins can benefit all 3 approaches (B. M. Ogle, et al., *Science Translational Medicine* 8, 342ps313-342ps313 (2016)). In the present example, the concept of sequential delivery of TIMP-3, FGF-2, and SDF-1α on countering the multitude of pathologies post-MI was explored in a rat model. These three proteins impart significant benefit on cardiac function after MI. The results, presented herein, demonstrate the ability of the fibrin gel-coacervate composite to provide early release of TIMP-3 by one week, followed by a sustained release of FGF-2 and SDF-1α that lasted at least six weeks.

The efficacy of spatiotemporal release of TIMP-3, FGF-2, and SDF-1α from the fibrin gel-coacervate composite was tested in a rat MI model and was compared to sham, saline, and free proteins groups. The CR group's significant potential to improve cardiac function and trigger repair mechanisms after infarction was demonstrated bringing it close to the normal case of the sham control in many evaluations. In most cases, CR showed significant differences compared to saline group, and to free proteins group in many cases. The free-proteins group, although showing some potential and trends of improvement in different evaluations, was not able to induce significant repair as CR did compared to saline. This was indicative of the importance of controlled and timed release of TIMP-3, FGF-2, and SDF-1α. Many protein therapies fail to prove long-term efficacy for MI treatment because of the shortcomings of proteins applied in free form, including very short-half lives, low retention at the target site, high doses required, and lack of spatiotemporal cues (P. Tayalia, et al., Controlled growth factor delivery for tissue engineering. *Advanced materials* 21, 3269-3285 (2009)). A recent study concluded that bolus injections of a cocktail of four important proteins: FGF-2, SDF-1α, IGF-I, and hepatocyte growth factor (HGF), did not improve cardiac function, reduce infarct size, or promote stable microvasculature (H. Hwang, et al., The combined administration of multiple soluble factors in the repair of chronically infarcted rat myocardium. *Journal of cardiovascular phar-*

*macology* 57, 282-286 (2011)). The study's results might be attributed to the absence of controlled release because without properly protecting the therapeutic proteins and delivering them spatiotemporally, a therapy might prove ineffective at cardiac repair. The delivery approach provided herein offers a solution to these challenges, by protecting the proteins within the fibrin gel-coacervate composite, localizing their presence at target tissue, and releasing them spatiotemporally.

The CR group significantly improved the heart contractile function as early as one week after MI and lasted up to eight weeks in comparison to saline and free proteins groups, which had the cardiac function continuously drop over the period tested, measured by echocardiography and further confirmed by cardiac MRI at eight weeks. A cardiac function improvement of 60-75% above non-treated infarcted hearts is reported. This effectively reduced the risk of MI progressing to heart failure. Significant reductions in ventricular dilation, ventricular wall thinning, myocardial stiffness, and MMP activity. These assessments are interrelated and linked to adverse remodeling and early ECM degradation. The reductions we show in these evaluations might be attributed to the vital role of early TIMP-3 release from the delivery system. TIMP-3 is an ECM-bound enzyme that forms tight non-covalent and stable complexes with the non-activated latent form of MMPs (pro-MMP), blocking the MMP's catalytic domain and preventing its access to substrates (R. Visse, et al., Matrix metalloproteinases and tissue inhibitors of metalloproteinases: structure, function, and biochemistry. *Circulation research* 92, 827-839 (2003); M. D. Sternlicht, et al., How matrix metalloproteinases regulate cell behavior. *Annual review of cell and developmental biology* 17, 463-516 (2001); and H. Yu, et al., TIMP-3 binds to sulfated glycosaminoglycans of the extracellular matrix. The Journal of biological chemistry 275, 31226-31232 (2000)). This effectively inhibits activation of MMPs, responsible for cleaving and hydrolyzing many components of the ECM including elastin, fibronectin, collagen, and proteoglycans (R. Visse, et al., *Circulation research* 92, 827-839 (2003); M. D. Sternlicht, et al., *Annual review of cell and developmental biology* 17, 463-516 (2001); and T. H. Vu, et al. Matrix metalloproteinases: effectors of development and normal physiology. *Genes & development* 14, 2123-2133 (2000)).

This feature of TIMP-3, being able to reduce ECM degradation, likely contributed to mitigating LV adverse remodeling, wall thinning, and dilation; thereby reducing the risk of cardiac rupture and contractile dysfunction. Other studies have shown the importance of TIMP-3 in cardiac diseases. Deficiency in TIMP-3 has been reported to lead to cardiac dilation, dysfunction, rupture, and mortality. Cell-based TIMP-3 gene delivery improved heart function and reduced cardiac expression and activity of MMP-2 and -9 (H. Tian, et al. Inhibiting matrix metalloproteinase by cell-based timp-3 gene transfer effectively treats acute and chronic ischemic cardiomyopathy. *Cell transplantation* 21, 1039-1053 (2012)). TIMP-3 delivered by collagen or hyaluronic gels was able to improve ejection fraction and reduce ventricular dilation and infarct size in rat and pig models (S. R. Eckhouse, et al., Local hydrogel release of recombinant TIMP-3 attenuates adverse left ventricular remodeling after experimental myocardial infarction. *Science translational medicine* 6, 223ra221 (2014) and A. Uchinaka, et al., Tissue inhibitor of metalloproteinase-1 and -3 improves cardiac function in an ischemic cardiomyopathy model rat. *Tissue engineering. Part A* 20, 3073-3084 (2014)).

The unregulated and excessive collagen deposition in the infarct, and later non-infarct regions, leads to interstitial fibrosis that increases myocardial stiffness and risk of contractile dysfunction. Fibrosis arises as a result of an imbalance in ECM structure and increased production of collagen by different cells, mainly myofibroblasts. Myofibroblasts contribute to adverse remodeling and are heavily influenced by the signaling of pro-fibrotic factors such as TGF-$\beta$. In the present example, it is demonstrated that the spatiotemporal delivery of TIMP-3, FGF-2, and SDF-1$\alpha$ prevented the development of interstitial fibrosis and the expansion of scar and granulation tissue to a large extent. Our CR group proved very effective at decreasing the levels of TGF-$\beta$1, a main promoter of fibrosis post-infarction. Therapies that aimed to antagonize TGF-$\beta$ and reduce fibrosis proved beneficial for the heart recovery (K. E. Porter, et al., Simvastatin reduces human atrial myofibroblast proliferation independently of cholesterol lowering via inhibition of RhoA. *Cardiovascular research* 61, 745-755 (2004); Y. Sun, et al., Angiotensin II, transforming growth factor-beta1 and repair in the infarcted heart. *Journal of molecular and cellular cardiology* 30, 1559-1569 (1998); N. A. Turner, et al., Chronic beta2-adrenergic receptor stimulation increases proliferation of human cardiac fibroblasts via an autocrine mechanism. *Cardiovascular research* 57, 784-792 (2003); C. M. Yu, et al., Effects of combination of angiotensin-converting enzyme inhibitor and angiotensin receptor antagonist on inflammatory cellular infiltration and myocardial interstitial fibrosis after acute myocardial infarction. *Journal of the American College of Cardiology* 38, 1207-1215 (2001)). These results likely helped in the preservation of myocardial elasticity as witnessed in the CR group. Therefore, the efficacy of the spatiotemporal delivery approach at preventing the excessive deposition of fibrillary collagen reduced the risk of stiffening the ventricular wall, its loss of contractile ability, and progression to heart failure. An excessive inflammatory response can have detrimental effects after MI. Large amounts of reactive oxygen species (ROS) produced by inflammatory cells invading the infarcted myocardium can cause massive cell death. The spatiotemporal delivery approach employed herein proved effective at reducing inflammation and promoting tissue repair. The results revealed the CR's reduction of non-M2 macrophages, which contain M1 macrophages that exacerbate inflammation and ECM degradation. An increase in M2 macrophages, which contribute to reconstruction of the ECM and anti-inflammatory effects is also reported herein. TIMP-3, provided by this delivery approach, can exert anti-inflammatory effects by inhibiting TNF-$\alpha$-converting enzyme (TACE), the enzyme activator of TNF-$\alpha$. TNF-$\alpha$ is a pro-inflammatory factor which increases in heart failure and is involved in inducing inflammatory cell invasion of the infarcted myocardium, MMP production, and cell apoptosis. It is demonstrated that the CR groups helps reduce the levels of pro-inflammatory cytokines IL-1$\beta$, IL-6, and TNF-$\alpha$. The strategy reduced the potentially deleterious impact of excessive inflammation by preventing the infiltration of harmful macrophages into the infarcted myocardium or possibly forcing a change in the phenotype of present ones to become of M2 phenotype involved in tissue repair.

As MI causes the death of millions of cardiomyocytes and puts millions more at risk, it is an indispensable task to support the survival of cardiomyocytes after MI and prevent their apoptosis. CR showed remarkable ability to preserve the viability of the cardiac muscle, activate pro-survival molecular pathways ERK1/2 and Akt, inhibit apoptosis mediated by caspase-3, and increase expression of anti-apoptotic factor IGF-I. Studies have proved the important role of activating the PI3K/Akt and Ras-Raf-MEK-ERK pathways to inhibit apoptosis and provide cardioprotection (A. Kis, et al., Second window of protection following myocardial preconditioning: an essential role for PI3 kinase and p70S6 kinase. *Journal of molecular and cellular cardiology* 35, 1063-1071 (2003); A. Tsang, et al., Postconditioning: a form of "modified reperfusion" protects the myocardium by activating the phosphatidylinositol 3-kinase-Akt pathway. *Circulation research* 95, 230-232 (2004); Y. Wang, Mitogen-activated protein kinases in heart development and diseases. Circulation 116, 1413-1423 (2007)). The complementary proteins in the system described herein, TIMP-3, FGF-2, and SDF-1α have all been reported to prevent cardiomyocyte apoptosis. Moreover, CR induced higher secretions levels of IGF-I and Shh. IGF-I is a well-studied potent cardioprotective and anti-apoptotic factor that activates the PI3K/Akt pathway and prevents cardiomyocyte apoptosis. Shh also reduces cardiomyocyte apoptosis through increased expression of pro-survival markers and reduced expression of apoptotic markers, as we and other groups have shown.

In addition, the CR group improved revascularization of the infarcted myocardium, triggering a robust angiogenesis process that led to the formation of mature neovessels with potential of participating in blood flow and perfusion. The triggers behind the formation of mature neovasculature in the borderzones of the infarct region can be linked mainly to FGF-2 and, to a lesser degree SDF-1α, present in the described protein combination and delivered in a sustained manner by the coacervate. As a strong angiogenic factor, FGF-2 induces endothelial cell proliferation and sprouting leading to the formation of tube-like structures that evolve into neovessels with lumens. Protein signaling results shows that the delivery group upregulates VEGF expression, which is an endothelial-specific factor that is important for angiogenesis and vasodilation All these indications support our finding that spatiotemporal delivery of TIMP-3, FGF-2, and SDF-1α leads to the formation of new, mature, and stable blood vessels, necessary to the repair of MI injury.

Stem cell recruitment to the infarct region is another important aspect of an effective therapy because of the potential of stem cells to ultimately differentiate into cardiac and vascular cells and/or support the repair by paracrine signaling, thereby supporting the survival of remaining cardiomyocytes and regeneration of a viable myocardium that replaces the lost damaged one. Our CR group showed significant ability at homing stem cells to the borderzones of the infarct. This is likely due to the sustained bioavailability of SDF-1α provided by the coacervate within our composite. SDF-1α is a powerful chemoattractant that can mobilize different types of progenitor cells such as endothelial progenitor cells (EPCs), hematopoietic stem cells (HSC), mesenchymal stem cells (MSCs), and cardiac stem cells (CSCs) to the infarcted myocardium There are some limitations to this study. Although an ischemia-reperfusion model would have been more clinically-relevant, a permanent ligation MI model was used in the rats of this study in order to induce more severe damages to the myocardium, thus enabling the detection of bigger differences between comparison groups due to different treatments. Due to limited number of animals at the two-week time point, only histology experiments were performed. Important assessments such as MMP activity, although performed at eight weeks, would be evaluated at earlier time points in future experiments. Small animal models as the one employed in this study provide significant insight in protein therapy. However, a large animal model such as a pig MI model is the logical next step because adult pigs present similar anatomy, response to ischemic insult, and expansion of an infarct to humans. Another area of improvement is to achieve catheter delivery to reduce surgical invasiveness. Viscosity and gelation parameters need to be optimized so that gelation doesn't occur while the injectable material is still in the catheter, or too late after injection where the therapeutic cargo would diffuse away from the target site.

Materials and Methods

Rationale and study design. The approach here was to inject a fibrin-coacervate composite gel loaded with TIMP-3, FGF-2, and SDF-1α for spatiotemporal release in the infarcted hearts of rats. The effects of this therapeutic approach on cardiac function, dilation, and myocardial strain levels were assessed at different time points after MI by multimodality imaging (echocardiography, MRI). Tissue-level changes were evaluated at two and/or eight weeks using histology, immunohistochemistry, western blot, and ELISA.

Power analysis. In a recent study, MRI was for assessment of cardiac function in a rat MI model at four weeks (6). From the results of this cardiac assessment, we had a standard deviation (SD) of σ=3%. Based on this value, a power analysis calculation carried out with Minitab statistical software estimates that in order to be able to detect an effect size of 6% (~2 SD) between EF % of treatment and sham, with a significance value of 5% and a power of 80%, at least n=6 animals per group were required.

The treatment assignments were randomized at the time of surgery. A total of 56 rats were used in this study for four groups: Sham, saline, free proteins, and CR with evaluations performed at two weeks (n=17 rats; 4-5 per group) and eight weeks (n=39; 9-10 per group). Sample sizes for each experimental measurement are provided in the figure legend or text, as appropriate.

Release assay of complementary proteins: PEAD was synthesized as previously described (H. Chu, et al., Design, synthesis, and biocompatibility of an arginine-based polyester. *Biotechnology progress* 28, 257-264 (2012)). The release assay was performed as previously described and further detailed herein (H. K. Awada, et al. Sequential delivery of angiogenic growth factors improves revascularization and heart function after myocardial infarction. *Journal of controlled release: official journal of the Controlled Release Society* 207, 7-17 (2015)).

Rat acute MI model: The induction of MI was performed as previously described (H. K. Awada, et al., Factorial Design of Experiments to Optimize Multiple Protein Delivery for Cardiac Repair. *ACS Biomaterials Science & Engineering* 2, 879-886 (2016); H. K. Awada, et al. *Journal of controlled release: official journal of the Controlled Release Society* 207, 7-17 (2015)) and further detailed herein. Four groups (n=56 rats) were evaluated: sham, saline, free proteins, and CR. Empty vehicle (empty fibrin gel-coacervate composite) was not tested as a control in this study as it has shown no difference to saline in our previous work (H. K. Awada, et al. *Journal of controlled release: official journal of the Controlled Release Society* 207, 7-17 (2015)).

Echocardiography and cardiac MRI Echocardiography and cardiac MRI were performed to compute ESA, EDA, FAC, ESV, EDV, and EF as previously described (6, 19) and further detailed in Supplementary Methods.

Myocardial strain level measurements. The B-mode frames of LV short-axis view acquired at eight weeks post-MI were analyzed (n=5 rats per group) using a strain analysis algorithm (VevoStrain™, Vevo2100). Five regions of interest (ROI) were selected along the LV mid-wall including one ROI in the anterior lateral (infarcted area) and four ROIs in the anterior medial, septal, posterior, posterior lateral (unaffected areas) walls of the LV. The peak strain in the infarcted area was normalized to the average peak strains of the four ROIs in unaffected LV walls during full cardiac cycles. The radial strain, defined as the percent change in myocardial wall thickness, was computed.

Histology: At two weeks (n=4-5 per group) and eight weeks (n=5-7 per group) post-infarction, rats were sacrificed by injecting 2 ml of saturated potassium chloride (KCl) solution (Sigma Aldrich, St. Louis, MO) in the LV to arrest the heart in diastole. Hearts were harvested, fixed in 2% paraformaldehyde (fisher Scientific, Fair Lawn, NJ) for 1-2 hours, deposited in 30% sucrose solution (w/v) overnight, frozen in O.C.T compound (Fisher Healthcare, Houston, TX), and stored at −20° C. Specimens were cryosectioned at 8 µm thickness from apex to the ligation level with 500 µm intervals.

Hematoxylin and eosin (H&E) staining was performed for general evaluation. H&E stained slides were selected and the ventricular wall thickness in the infarct zone (n=3-4 per group at two wks, n=4-6 at eight wks) was measured near the mid-section level of the infarct tissue using NIS Elements AR imaging software (Nikon Instruments, Melville, NY).

For assessment of interstitial fibrosis, picrosirius red staining was used to stain collagen fibers and image under polarized light. The fraction area of collagen deposition in the cross-sectional area of the whole heart was measured by NIS software near the mid-section level of the infarct tissue (n=3-5 per group at two wks, n=4-7 at eight wks). An object count tool was used to include RGB pixels specific to the stained collagen fibers in the heart area by defining a proper threshold value.

Immunohistochemistry: For evaluation of inflammation, a rabbit polyclonal antibody F4/80 (1:100, Santa Cruz Biotechnology, Dallas, TX), a pan-macrophage surface marker, was used followed by an Alexa fluor 594 goat anti-rabbit antibody (1:200, Invitrogen, Carlsbad, CA). Slides were also co-stained by a mouse anti-rat CD163 (1:150, Bio-Rad Laboratories, Hercules, CA), an M2 macrophage phenotype marker, followed by an Alexa fluor 488 goat anti-mouse antibody (1:200, Invitrogen, Carlsbad, CA). Slides were last counterstained with 4',6-diamidino-2-phenylindole (DAPI) (Invitrogen, Carlsbad, CA). For quantification near the mid-section level of the infarct tissue, F4/80-positive and CD163-positive cells were counted in two opposite regions of the infarct border zone, averaged, and reported per mm$^2$ areas (n=3-4 rats per group at two wks).

For evaluation of cardiac muscle viability, a rabbit polyclonal cardiac troponin I (cTnI) antibody (1:200, US Abcam, Cambridge, MA) was used followed by an Alexa fluor 488 goat anti-rabbit antibody (1:200, Invitrogen, Carlsbad, CA). Slides were counterstained with DAPI. The fraction area of viable cardiac muscle in the cross-sectional area of the whole heart was measured by NIS Elements AR software near the mid-section level of the infarct tissue (n=3-5 per group at two wks, n=5-6 at eight wks). An object count tool was used to include RGB pixels specific to the stained viable cardiac muscle in the heart area by defining a proper threshold value.

For evaluation of angiogenesis, endothelial cells (ECs) were detected by a rabbit polyclonal von Willebrand factor (vWF) antibody (1:200, US Abcam, Cambridge, MA) followed by an Alexa fluor 594 goat anti-rabbit antibody (1:200). Mural cells were detected by a FITC-conjugated anti-α-smooth muscle actin (α-SMA) monoclonal antibody (1:500, Sigma Aldrich, St. Louis, MO). Slides were last counterstained with DAPI. For quantification near the mid-section level of the infarct tissue, vWF-positive vessels (defined as those with lumen) and α-SMA-positive vessels were counted in two opposite regions of the infarct border zone, averaged, and reported per mm$^2$ areas (n=3-4 rats per group at two wks, n=5-6 per group at eight wks).

For evaluation of stem cell homing, stem/progenitor cells were detected by a rabbit polyclonal c-Kit antibody (1:100, Santa Cruz Biotechnology, Dallas, TX) followed by an Alexa fluor 488 goat anti-rabbit antibody (1:200). Slides were counterstained with DAPI. For quantification near the mid-section level of the infarct tissue, c-Kit-positive cells were counted in two opposite regions of the infarct border zone, averaged, and reported per mm$^2$ areas (n=5 rats per group at eight wks).

Molecular markers expression by western blot: Rat hearts (n=15) were harvested and rapidly stored at −80° C. for western blotting. For protein extraction, myocardial specimens weighing approximately 100 mg were excised from the LV generating a composite material comprising a spectrum between normal, infarct, and borderzone tissue. The tissues were then homogenized at 0.2 µg/ml in a modified lysis RIPA buffer (50 mM Tris-HCl, 1% NP-40, 20 mM DTT, 150 mM NaCl, pH=7.4) with protease and phosphatase inhibitors. The complex was then centrifuged at 12,100 g for 10 min, and the supernatant was collected and stored at −80° C. until use.

For total protein content, the extracts above were quantified with Pierce 660 nm Protein Assay (Thermo Fisher Scientific, Waltham, MA). The equivalent of 100 µg protein was separated using 11.5% gel and then transferred onto a PVDF membrane (Bio-Rad Laboratories, Hercules, CA). The membrane was blocked with 5% BSA in TBS with 0.05% TWEEN® 20 (polysorbate 20) for 1 h, then incubated with following antibody solutions: AKT, p-AKT, ERK1/2, p-ERK1/2 (all at 1:300, Santa Cruz Biotechnology, Dallas, TX), cleaved caspase-3 (1:1,000, Cell Signaling Technology, Boston, MA), and GAPDH (1:5000, US Abcam, Cambridge, MA). The membranes were washed with TBS three times and incubated with secondary antibodies for 2 h at room temperature. Signals were visualized using the ChemiDic™ XRS+Imaging System (Bio-Rad Laboratories, Hercules, CA), and band densities were quantified using NIH ImageJ (n=3 per group).

Myocardial protein secretion levels by ELISA: The tissue lysates acquired in the western blot section (n=3-4 rats per group) were used for detecting the levels of insulin-like growth factor-I (IGF-I), vascular endothelial growth factor (VEGF), sonic hedgehog (Shh), transforming growth factor-β1 (TGF-β1), interleukin 1β (IL-1β), IL-6, and tissue necrosis factor-α (TNF-α) in the LV myocardium. Sandwich ELISA kits (PeproTech, Rocky Hill, NJ) were used per the manufacturer's instructions with lysate dilutions for VEGF (1:20), IGF-I (1:50), IL-1β(1:15), IL-6 (1:15), and TNF-α (1:15). For Shh and TGF-β1, indirect ELISAs were run using rabbit polyclonal antibodies against Shh and TGF-β1 (both at 1:30, Santa Cruz Biotechnology, Dallas, TX) followed by a secondary biotinylated goat anti-rabbit IgG (1:100, Santa Cruz Biotechnology, Dallas, TX). Lysates were diluted 1:15 for Shh and 1:25 for TGF-01. The absorbance at 450/540 nm was measured by a SynergyMX plate reader. Results were corrected to account for differences in total protein content of samples.

MMP-2/9 activity assay: The tissue lysates acquired in the western blot section (n=3-4 rats per group) were used for detecting the activity of MMP-2/9 in the LV myocardium. The Calbiochem InnoZyme™ Gelatinase activity assay fluorogenic kit (EMD Millipore, Billerica, MA) was followed per the manufacturer's instructions. Briefly, lysate samples (diluted 1:2 in activation buffer) were incubated with a fluorogenic substrate solution that is highly selective for MMP-2 and MMP-9. Gelatinases in the sample lysates of the myocardium cleave the substrate, resulting in an increase in fluorescent signal measured at an excitation wavelength of 320 nm and an emission wavelength of 405 nm by a SynergyMX plate reader. The gelatinase control, activated similarly, was used at serial dilutions to create a standard curve for converting the fluorescence values of MMP activity to concentrations (ng/ml).

Statistical analysis: Results are presented as means±standard deviations (SD). GraphPad Prism 5.0 software (La Jolla, CA) was used for statistical analysis. Statistical differences between groups were analyzed by one-way ANOVA (multiple groups) or two-way repeated ANOVA (repeated echocardiographic measurements) with 95% confidence interval. Bonferroni multiple comparison test was performed for ANOVA post-hoc analysis. Statistical significance was set at $p<0.05$.

Release assay of complementary proteins: The release assay was performed using 100 ng of each of TIMP-3 (R&D Systems, Minneapolis, MN), FGF-2, and SDF-1α (PeproTech, Rocky Hill, NJ). All solutions were prepared in 0.9% sterile saline. FGF-2 and SDF-1α coacervates were made and mixed with a fibrinogen solution containing TIMP-3, followed by thrombin (Sigma-Aldrich, St. Louis, MO) to induce gelation, resulting in a 100 μl fibrin gel-coacervate composite. FGF-2 and SDF-1α coacervates were made by mixing 1 μl of 100 ng/μl for each of FGF-2 and SDF-1α with 2 μl of 5 mg/ml heparin first (Scientific Protein Labs, Waunakee, WI), then with 2 μl of 25 mg/ml of PEAD at PEAD:heparin:protein mass ratio of 250:50:1. This formed 6 μl of FGF-2/SDF-1α coacervates. Fibrin gel-coacervate composite was made by mixing 824l of 20 mg/ml fibrinogen (Sigma-Aldrich, St. Louis, MO), 1 μl of 5 mg/ml heparin, 1 μl of 100 ng/μl of TIMP-3; then the 6 μl FGF-2/SDF-1α coacervates were added, followed by 5 μl of 1 mg/ml aprotonin (Sigma-Aldrich, St. Louis, MO). Lastly, 5 μl of 1 mg/ml thrombin (Sigma-Aldrich, St. Louis, MO) was added to induce gelation, resulting in a 100 μl fibrin gel-coacervate composite.

A 100p1 of 0.9% saline was deposited on top of the gel composite to be collected at 1 h, 16 h, 1, 4, 7, 14, 28, and 42 days. The samples (n=3) were incubated at 37° C. After centrifugation at 12,100 g for 10 min, supernatant was collected and stored at −80° C. to detect amount of released proteins by sandwich enzyme-linked immunosorbent assay (ELISA) kits (PeproTech, Rocky Hill, NJ) (R&D Systems, Minneapolis, MN). The absorbance at 450/540 nm was measured by a SynergyMX plate reader (Biotek, Winooski, VT). Standard solutions (n=3) that contained 100 ng of each of the proteins in free form in 100p1 of 0.9% saline were prepared to create standard curves and determine total release.

Detailed method of rat MI model: Six to seven week old (175-225 g) male Sprague-Dawley rats (Charles River Labs, Wilmington, MA) were anesthetized first then maintained with 2% isoflurane at 0.3 L/min (Butler Schein, Dublin, OH), intubated, and connected to a mechanical ventilator to support breathing during surgery. The body temperature was maintained at 37° C. by a hot pad. The ventral side was shaved and a small incision was made through the skin. Forceps, scissors, and q-tips were used to dissect through the skin, muscles, and ribs. Once the heart was visible, the pericardium was torn. MI was induced by permanent ligation of the left anterior descending (LAD) coronary artery using a 6-0 polypropylene suture (Ethicon, Bridgewater, NJ). Infarct was confirmed by macroscopic observation of a change in color from bright red to light pink in the area below the ligation suture. Five minutes after the induction of MI, different treatment and control solutions were injected intramyocardially at three equidistant points around the infarct zone using a 31-gauge needle (BD, Franklin Lakes, NJ). Four groups (n=56 rats) were evaluated: sham, saline, free proteins, and delivered proteins. Empty vehicle (empty fibrin gel-coacervate composite) was not tested as a control in this study as it has shown no difference to saline in our previous work.

The sham group (n=13) underwent the surgery in which the heart was exposed and pericardium was torn, then chest was closed and rat recovered. The saline group (n=14) underwent the surgery in which MI was induced and 100 μl of 0.9% sterile saline was injected around the infarct region. The free proteins group (n=14) underwent the surgery in which MI was induced and 100 μl of 0.9% sterile saline containing 3 μg each of free TIMP-3, FGF-2, and SDF-1α was injected around the infarct region. The delivered proteins group (n=15) underwent the surgery in which MI was induced and 100 μl of fibrin gel-coacervate composite was injected around the infarct region. The fibrin gel-coacervate composite was prepared briefly as follows: 18 μl coacervate solution containing 3 μg each of FGF-2 and SDF-1α, 67p1 of 20 mg/ml fibrinogen, 6 μl of solution containing heparin and 3 μg of TIMP-3, 5 μl of 1 mg/ml aprotonin (Sigma-Aldrich, St. Louis, MO). Lastly, 4 μl of 1.5 mg/ml thrombin (Sigma-Aldrich, St. Louis, MO) was added and the total solution was injected shortly before gelation occurred, approximately 40 seconds after mixing. All solutions were prepared in 0.9% sterile saline. The chest was closed and the rat was allowed to recover. At multiple time points, rats were imaged using echocardiography. At eight weeks, a subset was imaged using cardiac MRI. After 2 (n=17) or 8 weeks (n=39), animals were sacrificed and hearts were harvested for histological, immunohistochemical, and western blot evaluations.

Echocardiography: At pre-MI, one, two, five and eight weeks post-MI, rats (n=9-10 per group) were anesthetized then maintained with 1-1.5% isoflurane gas throughout the echocardiographic study. Rats were placed in the supine position, immobilized on a heated stage equipped with echocardiography, and the hair in the abdomen was removed. The body temperature was maintained at 37° C. Short-axis videos of the LV by B-mode were obtained using a high-resolution in small animal imaging system (Vevo 2100, Visual Sonics, Ontario, Canada) equipped with a high-frequency linear probe (MS400, 30 MHz) (FUJIFILM VisualSonics, Canada). End-systolic (ESA) and end-diastolic (EDA) areas were measured using NIH ImageJ and fractional area change (FAC) was calculated as: [(EDA-ESA)/EDA]×100%. Percent improvements of one group over another were calculated as the difference between the % drops in FAC values of the first and second groups divided by the higher % drop of the two groups.

Cardiac MRI: Cardiac MRI was used to measure LV volumes and ejection fraction (EF) from infarcted rat hearts at eight weeks (n=5-8 per group). MRI was preformed using a Bruker Biospec 4.7-Tesla 40-cm scanner equipped with a 12-cm shielded gradient set, a 72 mm transmit RF coil (Bruker Biospin, Billerica MA), and a four-channel rat cardiac receive array (Rapid MR International, Columbus, OH). Rats were induced with isoflurane, intubated, and ventilated at 1 mL/100 g of body weight and maintained at 2% isoflurane in 2:1 $O_2:N_2O$ gas mixture at 60 BPM. During the MRI procedure rats were continually monitored and rectal temperature was maintained at 37° C. with warm air (SA Instruments, Stony Brook, NY). Following pilot scans, rats were imaged using a self-gated cine FLASH sequence (IntraGate) with the following parameters: TR/TE=9.0/3.0 ms, 40×40 mm FOV, 256×256 matrix, FA=10°, and 200 repetitions. 10-12 slices were collected to cover the area between the heart apex to the mitral valves with 1.5 mm slice thickness with common navigator slice. End-systolic and end-diastolic phases were identified for each subject and the LV cavity manually traced using NIH ImageJ to determine LV end-systolic (ESV) and end-diastolic (EDV) volumes. These volumes were used to compute ejection fraction as EF %=[(EDV−ESV)/EDV]×100%. Percent improvements of one group over another were calculated as the difference between the % drops in EF values of the first and second groups divided by the higher % drop of the two groups.

The following numbered clauses provide illustrative examples of various aspects of the invention.

1. A composition comprising a coacervate of a polycationic polymer, a polyanionic polymer, and platelet-rich plasma and/or serum, or a fraction or concentrate thereof.
2. The composition of clause 1, comprising platelet-rich plasma and wherein platelets of the platelet-rich plasma are activated to produce a fibrin clot, and the fibrin clot is optionally removed from the platelet-rich plasma.
3. The composition of clause 1, comprising pure platelet-rich fibrin (P-PRF) or leukocyte-rich PRF, with or without the fibrin clot removed.
4. The composition of clause 2 or 3, wherein the fibrin clot is removed and the protein content of the PRP is concentrated (for example, as compared to the solution phase of activated PRP, in which the fibrin is removed, but prior to concentration, e.g., by use of a centrifugal filter unit).
5. A composition comprising a coacervate of a polycationic polymer, a polyanionic polymer, and a composition obtained from an organism or cultured cells, tissues or organs and containing a (complex, e.g.) mixture of proteins and/or growth factors produced by the organism or cultured cells, tissues or organs (that is, the composition is obtained from a living source, and though it may proceed through one or more fractionation and/or purification steps not limited to activation or fractionation, e.g., precipitation, chromatography, and/or affinity separation, as in the case of activated PRP as decribed herein in which the platelets of the PRP are activated, and optionally, the resultant clot is removed and the composition is optionally concentrated, it is not an isolated or purified single constituent, but includes costituents, such as, for example, a plurality (at least two, e.g., three or more or four or more) of proteins and/or growth factors, essentially in relative amounts and/or a ratio found in, or produced by the cells or organism).
6. The composition of clause 5, wherein the composition containing a complex mixture of proteins and/or growth factors is prepared from a bodily fluid of an organism, a cell or tissue lysate, or conditioned media in which cells or a tissue is grown. 7. The composition of clause 5, wherein the cells, tissues, or organism are genetically-modified.
8. A composition comprising:
   a. a hydrogel comprising TIMP-3; and
   b. a complex or coacervate of a polycationic polymer, a polyanionic polymer, FGF-2 and SDF-1α embedded in the hydrogel.

9. The composition of any one of clauses 1-8, wherein the polyanionic polymer is a sulfated or sulfamated polysaccharide.
10. The composition of any one of clauses 1-8, wherein the polyanionic is a heparin or heparan sulfate.
11. The composition of any one of clauses 1-10, wherein the polycationic polymer is a polymer composition comprising at least one moiety selected from the following:
   (a) [—OC(O)—CH(NHY)—CH$_2$—C(O)O—CH$_2$—CH(O—R1)-CH$_2$—O—CH$_2$—CH$_2$—O—CH$_2$—CH(O—R2)-CH$_2$-]$_n$,
   (b) [—OC(O)—CH$_2$—CH(NHY)-C(O)O—CH$_2$—CH(O—R1)-CH$_2$—O—CH$_2$—CH$_2$—O—CH$_2$—CH(O—R2)-CH$_2$-]$_n$,
   (c) [—OC(O)—CH(NHY)—CH$_2$—CH$_2$—C(O)O—CH2-CH(O—R1)-CH$_2$—O—CH$_2$—CH$_2$—O—CH$_2$—CH(O—R2)-CH$_2$-]$_n$, and/or
   (d) [—OC(O)—CH$_2$—CH$_2$—CH(NHY)-C(O)O—CH2-CH(O—R1)-CH$_2$—O—CH$_2$—CH$_2$—O—CH$_2$—CH(O—R2)-CH$_2$-]$_n$,
wherein Y is —C(O)—CH(NH$_3^+$)—(CH$_2$)$_3$—NH—C(NH$_2$)$_2^+$ or —C(O)—CH(NH$_3^+$)—(CH$_2$)$_4$—(NH$_3$)$^+$, and R1 and R2 are the same or different and are independently selected from the group consisting of hydrogen, a carboxy-containing group, a C$_{1-6}$ alkyl group, an amine-containing group, a quaternary ammonium containing group, and a peptide.
12. The composition of clause 11, wherein the polycationic polymer has a polydispersity index of less than 3.0.
13. The composition of clause 11, wherien R1 and R2 are selected from the group consisting of Ile-Lys-Val-Ala-Val (IKVAV) (SEQ ID NO: 4), Arg-Gly-Asp (RGD), Arg-Gly-Asp-Ser (RGDS) (SEQ ID NO: 5), Ala-Gly-Asp (AGD), Lys-Gln-Ala-Gly-Asp-Val (KQAGDV) (SEQ ID NO: 6), Val-Ala-Pro-Gly-Val-Gly (VAPGVG) (SEQ ID NO: 7), APGVGV (SEQ ID NO: 8), PGVGVA (SEQ ID NO: 9), VAP, GVGVA (SEQ ID NO: 10), VAPG (SEQ ID NO: 11), VGVAPG (SEQ ID NO: 12), VGVA (SEQ ID NO: 13), VAPGV (SEQ ID NO: 14) and GVAPGV (SEQ ID NO: 15).
14. The composition of clause 11, wherein Y is —C(O)—CH(NH$_3$+)—(CH$_2$)$_4$—(NH$_3$)+.
15. The composition of clause 11, wherein Y is —C(O)—CH(NH$_3$+)—(CH$_2$)$_3$—NH—C(NH$_2$)$_2$+.
16. The composition of any one of clauses 1-15, wherein the ratio of the polycationic polymer to the polyanionic polymer in the composition results in a neutral, negative, or positive charge in the coacervate.
17. The composition of clause 8, wherein the hydrogel comprises fibrin.
18. The composition of any one of clauses 8-17, wherein the amounts of TIMP-3, FGF-2 and/or SDF-1α in the compositions are amounts effective to treat a myocardial infarct in a patient (that is, an amount effective to improve one or more clinically-relevant measures of the myocardial infarct in the patient.
19. A method of treating a patient having a myocardial infarct, comprising administering the composition of any one of clauses 8-18 to a patient at or near a site of a myocardial infarct in the patient, in an amount effective to treat a myocardial infarct in a patient.
20. A method of treating a wound in a patient, comprising administering a composition according to any one of clauses 1-7 at or adjacent to a wound in the patient, in an amount effective to treat a wound in a patient.
21. The method of clause 20, wherein the composition is administered to the patient more than once.
22. A method of preparing a therapeutic composition for use in treating a wound in a patient, comprising:

a. mixing a polyanionic polymer with platelet-rich plasma, serum, a fraction thereof, a concentrate thereof, or platelet-rich plasma (PRP) in which the platelets have been activated to produce a fibrin clot; and
b. mixing the PRP and polyanionic polymer mixture with a polycationic polymer.

23. The method of clause 22, wherein the polyanionic polymer is a sulfated or sulamated polysaccharide, such as heparin or heparan sulfate.

24. The method of clause 22 or 23, wherein the polycationic polymer is a polymer composition comprising at least one moiety selected from the following:
(a) [—OC(O)—CH(NHY)—CH$_2$—C(O)O—CH$_2$—CH(O—R1)-CH$_2$—O—CH$_2$—CH$_2$—O—CH$_2$—CH(O—R2)-CH$_2$-]$_n$,
(b) [—OC(O)—CH$_2$—CH(NHY)-C(O)O—CH$_2$—CH(O—R1)-CH$_2$—O—CH$_2$—CH$_2$—O—CH$_2$—CH(O—R2)-CH$_2$-]$_n$,
(c) [—OC(O)—CH(NHY)—CH$_2$—CH$_2$—C(O)O—CH2-CH(O—R1)-CH$_2$—O—CH$_2$—CH$_2$—O—CH$_2$—CH(O—R2)-CH$_2$-]$_n$, and/or
(d) [—OC(O)—CH$_2$—CH$_2$—CH(NHY)-C(O)O—CH2-CH(O—R1)-CH$_2$—O—CH$_2$—CH$_2$—O—CH$_2$—CH(O—R2)-CH$_2$-]$_n$,
wherein Y is —C(O)—CH(NH$_3^+$)—(CH$_2$)$_3$—NH—C(NH$_2$)$_2^+$ or —C(O)—CH(NH$_3^+$)—(CH$_2$)$_4$—(NH$_3$)$^+$, and R1 and R2 are the same or different and are independently selected from the group consisting of hydrogen, a carboxy-containing group, a C$_{1-6}$ alkyl group, an amine-containing group, a quaternary ammonium containing group, and a peptide.

25. The method of clause 24, wherein the polycationic polymer has a polydispersity index of less than 3.0.

26. The method of clause 24, wherein R1 and R2 are selected from the group consisting of Ile-Lys-Val-Ala-Val (IKVAV) (SEQ ID NO: 4), Arg-Gly-Asp (RGD), Arg-Gly-Asp-Ser (RGDS) (SEQ ID NO: 5), Ala-Gly-Asp (AGD), Lys-Gln-Ala-Gly-Asp-Val (KQAGDV) (SEQ ID NO: 6), Val-Ala-Pro-Gly-Val-Gly (VAPGVG) (SEQ ID NO: 7), APGVGV (SEQ ID NO: 8), PGVGVA (SEQ ID NO: 9), VAP, GVGVA (SEQ ID NO: 10), VAPG (SEQ ID NO: 11), VGVAPG (SEQ ID NO: 12), VGVA (SEQ ID NO: 13), VAPGV (SEQ ID NO: 14) and GVAPGV (SEQ ID NO: 15).

27. The method of clause 24, wherein Y is —C(O)—CH(NH$_3$+)—(CH$_2$)$_4$—(NH$_3$)+.

28. The method of clause 24, wherein Y is —C(O)—CH(NH$_3$+)—(CH$_2$)$_3$—NH—C(NH$_2$)$_{2+}$.

29. The method of any one of clauses 22-28, wherein the ratio of the polycationic polymer to the polyanionic polymer in the composition results in a neutral, negative, or positive charge in the coacervate.

30. The method of any one of clauses 22-29, wherein the platelet-rich plasma, serum, a fraction thereof, a concentrate thereof, or platelet-rich plasma (PRP) in which the platelets have been activated to produce a fibrin clot is autologous to a patient to be treated.

31. The method of any one of clauses 22-30, wherein the platelet-rich plasma, serum, a fraction thereof, a concentrate thereof, or PRP in which the platelets have been activated to produce a fibrin clot PRP in which the platelets have been activated is PRP in which the platelets have been activated to produce a fibrin clot PRP in which the platelets have been activated that is further processed to remove the fibrin clot from the PRP prior to mixing with the polyanionic polymer.

32. The method of clause 31, further comprising concentrating the proteins in the PRP.

33. The method of any one of clauses 22-32, further comprising applying the therapeutic composition to a medical device or wound dressing.

34. The method of clause 33, wherein the medical device or wound dressing is a bandage, suture, surgical mesh, limb or joint prosthesis, or a non-woven material.

35. A medical device or wound dressing comprising a composition according to any one of clauses 1-7.

36. The medical device or wound dressing of clause 35, wherein the medical device or wound dressing is a bandage, suture, surgical mesh, limb or joint prosthesis, or a non-woven material.

While the present invention is described with reference to several distinct embodiments, those skilled in the art may make modifications and alterations without departing from the scope and spirit. Accordingly, the above detailed description is intended to be illustrative rather than restrictive.

---

We claim:

1. A composition comprising:
   a) a hydrogel comprising tissue inhibitor of metalloproteinases 3 (TIMP-3); and
   b) a complex or coacervate of a polycationic polymer, a polyanionic polymer, fibroblast growth factor 2 (FGF-2), and stromal cell-derived factor 1 alpha (SDF-1α) embedded in the hydrogel.

2. The composition of claim 1, wherein the polyanionic polymer is heparin or heparan sulfate.

3. The composition of claim 1, wherein the polycationic polymer is a copolymer comprising a polyester backbone comprising a copolymer of ethylene glycol diglyceride and either aspartic acid or glutamic acid, and pendant arginine groups.

4. The composition of claim 3, wherein the polycationic polymer has a polydispersity index of less than 3.0.

5. The composition of claim 3, wherein the copolymer comprises a peptide are selected from the group consisting of Ile-Lys-Val-Ala-Val (IKVAV) (SEQ ID NO: 4), Arg-Gly-Asp (RGD), Arg-Gly-Asp-Ser (RGDS) (SEQ ID NO: 5), Ala-Gly-Asp (AGD), Lys-Gln-Ala-Gly-Asp-Val (KQAGDV) (SEQ ID NO: 9), VAP, GVGVA (SEQ ID NO: 10), VAPG (SEQ ID NO: 11), VGVAPG (SEQ ID NO: 12), VGVA (SEQ ID NO: 13), VAPGV (SEQ ID NO: 14) and GVAPGV (SEQ ID NO: 15).

6. The composition of claim 1, wherein the ratio of polycationic polymer to the polyanionic polymer in the compositions results in a neutral charge in the coacervate.

7. The composition of claim 1, wherein the hydrogel comprises fibrin.

8. The composition of claim 1, wherein the amount of TIMP-3, FGF-2 and/or SDF-1α in the composition is an amount effective to treat a myocardial infarct in a patient.

9. The composition of claim 1, wherein the polycationic polymer is a copolymer comprising a polyester backbone comprising a copolymer of ethylene glycol diglyceride and either aspartic acid or glutamic acid, and pendant lysine groups.

10. The composition of claim 1, wherein the polycationic polymer is poly(ethylene arginylaspartate diglyceride).

11. The composition of claim 1, wherein the polycationic polymer is poly(ethylene lysinlyaspartate diglyceride).

12. A method of preparing a therapeutic composition for use in treating a wound in a patient, comprising:
    forming a complex or coacervate of a polycationic polymer, a polyionic polymer, FGF-2, and SDF-1α; and
    embedding the complex or coacervate within a hydrogel comprising TIMP-3.

13. The method of claim 12, wherein the polyanionic polymer heparin or heparan sulfate.

14. The method of claim 12, wherein the polycationic polymer is a copolymer comprising a polyester backbone comprising a copolymer of ethylene glycol diglyceride and either aspartic acid or glutamic acid, and pendant arginine groups.

15. The method of claim 12, wherein the polycationic polymer has a polydispersity index of less than 3.0.

16. The method of claim 12, wherein the copolymer comprises a peptide selected from the group consisting of Ile-Lys-Val-Ala-Val (IKVAV)(SEQ ID NO:4), Arg-Gly-Asp (RGD), Arg-Gly-Asp-Ser (RGDS) (SEQ ID NO: 5), Ala-Gly-Asp (AGD), Lys-Gln-Ala-Gly-Asp-Val (KQAGDV) (SEQ ID NO: 9), VAP, GVGVA (SEQ ID NO: 10), VAPG (SEQ ID NO: 11), VGVAPG (SEQ ID NO: 12), VGVA (SEQ ID NO: 13), VAPGV (SEQ ID NO: 14) and GVAPGV (SEQ ID NO: 15).

17. The method of claim 12, wherein the ratio of polycationic polymer to the polyanionic polymer in the compositions results in a neutral charge in the coacervate.

18. The method of claim 12, wherein the hydrogel comprises fibrin.

19. The method of claim 12, wherein the amounts of TIMP-3, FGF-2 and/or SDF-1α in the compositions are amounts effective to treat a myocardial infarct in a patient.

20. A method of treating a patient having a myocardial infarct, comprising administering the composition of claim 1 to a patient in need thereof at or near a site of a myocardial infarct in the patient, in an amount effective to treat a myocardial infarct in a patient.

* * * * *

SEQUENCE LISTING

```
<160> NUMBER OF SEQ ID NOS: 15

<210> SEQ ID NO 1
<211> LENGTH: 288
<212> TYPE: PRT
<213> ORGANISM: Homo sapiens

<400> SEQUENCE: 1

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95
```

-continued

```
Gly Arg Gly Arg Ala Pro Glu Arg Val Gly Arg Gly Arg
            100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
        130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 2
<211> LENGTH: 93
<212> TYPE: PRT
<213> ORGANISM: Homo sapiens

<400> SEQUENCE: 2

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 3
<211> LENGTH: 211
<212> TYPE: PRT
<213> ORGANISM: Homo sapiens

<400> SEQUENCE: 3

Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
        35                  40                  45
```

```
Lys Lys Leu Val Lys Glu Gly Pro Phe Gly Thr Leu Val Tyr Thr Ile
     50                  55                  60

Lys Gln Met Lys Met Tyr Arg Gly Phe Thr Lys Met Pro His Val Gln
 65              70                  75                      80

Tyr Ile His Thr Glu Ala Ser Glu Ser Leu Cys Gly Leu Lys Leu Glu
                 85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
            115                 120                 125

Leu Ser Gln Arg Lys Gly Leu Asn Tyr Arg Tyr His Leu Gly Cys Asn
        130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 4
<211> LENGTH: 5
<212> TYPE: PRT
<213> ORGANISM: Artificial Sequence
<220> FEATURE:
<223> OTHER INFORMATION: Functional Group

<400> SEQUENCE: 4

Ile Lys Val Ala Val
1               5

<210> SEQ ID NO 5
<211> LENGTH: 4
<212> TYPE: PRT
<213> ORGANISM: Artificial Sequence
<220> FEATURE:
<223> OTHER INFORMATION: Functional Group

<400> SEQUENCE: 5

Arg Gly Asp Ser
1

<210> SEQ ID NO 6
<211> LENGTH: 6
<212> TYPE: PRT
<213> ORGANISM: Artificial Sequence
<220> FEATURE:
<223> OTHER INFORMATION: Functional Group

<400> SEQUENCE: 6

Lys Gln Ala Gly Asp Val
1               5

<210> SEQ ID NO 7
<211> LENGTH: 7
<212> TYPE: PRT
<213> ORGANISM: Artificial Sequence
<220> FEATURE:
```

```
<223> OTHER INFORMATION: Functional Group

<400> SEQUENCE: 7

Val Ala Val Pro Gly Val Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Functional Group

<400> SEQUENCE: 8

Ala Pro Gly Val Gly Val
1               5

<210> SEQ ID NO 9
<211> LENGTH: 6
<212> TYPE: PRT
<213> ORGANISM: Artificial Sequence
<220> FEATURE:
<223> OTHER INFORMATION: Functional Group

<400> SEQUENCE: 9

Pro Gly Val Gly Val Ala
1               5

<210> SEQ ID NO 10
<211> LENGTH: 5
<212> TYPE: PRT
<213> ORGANISM: Artificial Sequence
<220> FEATURE:
<223> OTHER INFORMATION: Functional Group

<400> SEQUENCE: 10

Gly Val Gly Val Ala
1               5

<210> SEQ ID NO 11
<211> LENGTH: 4
<212> TYPE: PRT
<213> ORGANISM: Artificial Sequence
<220> FEATURE:
<223> OTHER INFORMATION: Functional Group

<400> SEQUENCE: 11

Val Ala Pro Gly
1

<210> SEQ ID NO 12
<211> LENGTH: 6
<212> TYPE: PRT
<213> ORGANISM: Artificial Sequence
<220> FEATURE:
<223> OTHER INFORMATION: Functional Group

<400> SEQUENCE: 12

Val Gly Val Ala Pro Gly
1               5

<210> SEQ ID NO 13
<211> LENGTH: 4
<212> TYPE: PRT
<213> ORGANISM: Artificial Sequence
<220> FEATURE:
<223> OTHER INFORMATION: Functional Group
```

```
<400> SEQUENCE: 13

Val Gly Val Ala
1

<210> SEQ ID NO 14
<211> LENGTH: 5
<212> TYPE: PRT
<213> ORGANISM: Artificial Sequence
<220> FEATURE:
<223> OTHER INFORMATION: Functional Group

<400> SEQUENCE: 14

Val Ala Pro Gly Val
1               5

<210> SEQ ID NO 15
<211> LENGTH: 6
<212> TYPE: PRT
<213> ORGANISM: Artificial Sequence
<220> FEATURE:
<223> OTHER INFORMATION: Functional Group

<400> SEQUENCE: 15

Gly Val Ala Pro Gly Val
1               5
```